(12) United States Patent
Johnson et al.

(10) Patent No.: US 12,199,239 B2
(45) Date of Patent: Jan. 14, 2025

(54) SULFONIMIDE SALTS FOR BATTERY APPLICATIONS

(71) Applicants: Massachusetts Institute of Technology, Cambridge, MA (US); Samsung Electronics Co., Ltd., Suwon-si (KR)

(72) Inventors: Jeremiah Allen Johnson, Boston, MA (US); Yang Shao-Horn, Newton, MA (US); Robinson Anandakathir, Westford, MA (US); Mao Chen, Austin, TX (US); Shuting Feng, Cambridge, MA (US); Livia Giordano, Auburndale, MA (US); Mingjun Huang, Everett, MA (US); Wenxu Zhang, Cambridge, MA (US)

(73) Assignees: Massachusetts Institute of Technology, Cambridge, MA (US); Samsung Electronics Co., Ltd., Suwon-si (KR)

( * ) Notice: Subject to any disclaimer, the term of this patent is extended or adjusted under 35 U.S.C. 154(b) by 0 days.

(21) Appl. No.: 18/159,825

(22) Filed: Jan. 26, 2023

(65) Prior Publication Data

US 2024/0021874 A1  Jan. 18, 2024

Related U.S. Application Data

(60) Continuation of application No. 17/118,359, filed on Dec. 10, 2020, now Pat. No. 11,605,834, which is a
(Continued)

(51) Int. Cl.
 H01M 10/0565 (2010.01)
 C07C 311/13 (2006.01)
(Continued)

(52) U.S. Cl.
 CPC ....... H01M 10/0565 (2013.01); C07C 311/13 (2013.01); C07C 311/48 (2013.01);
(Continued)

(58) Field of Classification Search
 CPC .... C07C 311/13; C07C 311/15; C07C 311/48
 See application file for complete search history.

(56) References Cited

U.S. PATENT DOCUMENTS

2011/0111308 A1* 5/2011 Halalay ............. H01M 10/0525
429/344

FOREIGN PATENT DOCUMENTS

JP  2017016011 A * 1/2017

OTHER PUBLICATIONS

Morizur et al, Novel lithium and sodium salts of sulfonamides and bis(sulfonyl)imides: synthesis and electrical conductivity, Royal Society of Chemistry, New Journal of Chemistry, 38, 6193-6197 (2014) (Year: 2014).*
(Continued)

*Primary Examiner* — Amanda C. Walke
(74) *Attorney, Agent, or Firm* — Foley Hoag LLP; Dana M. Gordon; Alexander J. Chatterley

(57) ABSTRACT

A class of sulfonimide salts for solid-state electrolytes can be synthesized based on successive $S_NAr$ reactions of fluorinated phenyl sulfonimides: Fluorinated Aryl Sulfonimide Tags (FAST). The chemical and electrochemical oxidative stability of these FAST salts as well as other properties like solubility, Lewis basicity, and conductivity can be tuned by introducing different numbers and types of nucleophilic functional groups to the FAST salt scaffold.

12 Claims, 46 Drawing Sheets

Related U.S. Application Data division of application No. 15/875,201, filed on Jan. 19, 2018, now Pat. No. 10,892,520.

(60) Provisional application No. 62/519,683, filed on Jun. 14, 2017, provisional application No. 62/448,593, filed on Jan. 20, 2017.

(51) Int. Cl.
*C07C 311/48* (2006.01)
*H01M 10/052* (2010.01)
*H01M 10/0568* (2010.01)
*C07C 311/15* (2006.01)

(52) U.S. Cl.
CPC ..... *H01M 10/052* (2013.01); *H01M 10/0568* (2013.01); *C07C 311/15* (2013.01); *H01M 2300/0025* (2013.01); *H01M 2300/0082* (2013.01)

(56) References Cited

OTHER PUBLICATIONS

Herath et al, Ionic conduction in polyether-based lithium arylfluorosulfonimide ionic melt electrolytes, Eletrochimica Arts, 54, 5877-5883 (2009) (Year: 2009).*

* cited by examiner

SULFONIMIDE SALTS FOR BATTERY APPLICATIONS

CLAIM OF PRIORITY

This application is a continuation of U.S. application Ser. No. 17/118,359, filed on Dec. 10, 2020, which is a divisional application of U.S. application Ser. No. 15/875,201, filed on Jan. 19, 2018, which claims the benefit of U.S. Provisional Application No. 62/448,593 filed on Jan. 20, 2017, and U.S. Provisional Application No. 62/519,683 filed on Jun. 14, 2017, each of which is incorporated by reference in its entirety.

TECHNICAL FIELD

This invention relates to materials for energy storage devices.

BACKGROUND

The increasing demands of modern electronics necessitate the development of energy storage devices that feature greater power and energy densities without compromising affordability and safety. With the advantages of broad electrochemical stability window, high thermal stability, and low vulnerability towards moisture hydrolysis, lithium bis(trifluoromethanesulfonyl)imide (LiTFSI) is widely used as a lithium source in new battery chemistries with higher theoretical energy densities beyond lithium-ion battery, such as lithium-air and lithium-sulfur batteries. Moreover, LiTFSI is also the most studied lithium salt especially in solid-state polymer electrolytes, due to its desirable solubility and excellent stability. However, chemically inert LiTFSI cannot be easily modified to optimize its properties or for conjugation to other molecules, polymers, or substrates to prepare single-ion conducting polymer electrolytes.

SUMMARY

In one aspect, a composition can include:

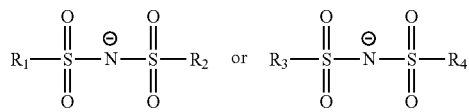

wherein $R_1$ is —$CF_3$ or a fluorinated phenyl and $R_2$ is a fluorinated phenyl or $R_3$ is —$CF_3$ or a fluorinated phenyl and $R_4$ is a fluorinated phenyl, wherein at least one of $R_3$ and $R_4$ is substituted by a nucleophile.

In certain circumstances, $R_1$ can be —$CF_3$.

In certain circumstances, $R_1$ can be a fluorinated phenyl. The fluorinated phenyl can have at least two fluorine groups. For example, the fluorinated phenyl can have a formula

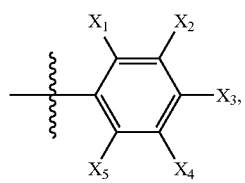

wherein each of $X_1$, $X_2$, $X_3$, $X_4$, and $X_5$, independently, is F or $CF_3$.

In another example, the fluorinated phenyl can have a formula

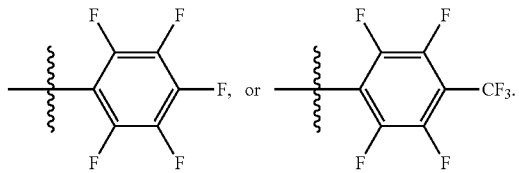 [SMILES: *c1c(F)c(F)c(F)c(F)c1F ; *c1c(F)c(F)c(C(F)(F)F)c(F)c1F]

In certain circumstances, $R_3$ can be —$CF_3$ or a fluorinated phenyl and $R_4$ can be a fluorinated phenyl, wherein at least one of $R_3$ and $R_4$ is substituted by a nucleophile.

In certain circumstances, the fluorinated phenyl can have a formula

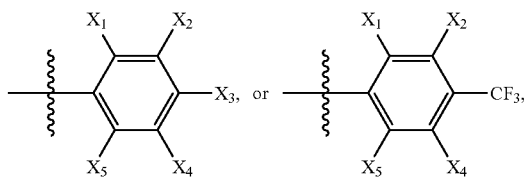

wherein each of $X_1$, $X_2$, $X_3$, $X_4$, and $X_5$, independently, is F, $OR_a$, or $NR_cR_d$, wherein $R_a$ is C1-C6 alkyl, benzalkyl, or substituted or unsubstituted phenyl, $R_b$ is C1-C6 alkyl, benzalkyl, or phenyl, $R_c$ is C1-C6 alkyl, benzalkyl, or phenyl, or $R_b$ and $R_c$ together form a three to eight membered ring.

In certain circumstances, the fluorinated phenyl can have a formula

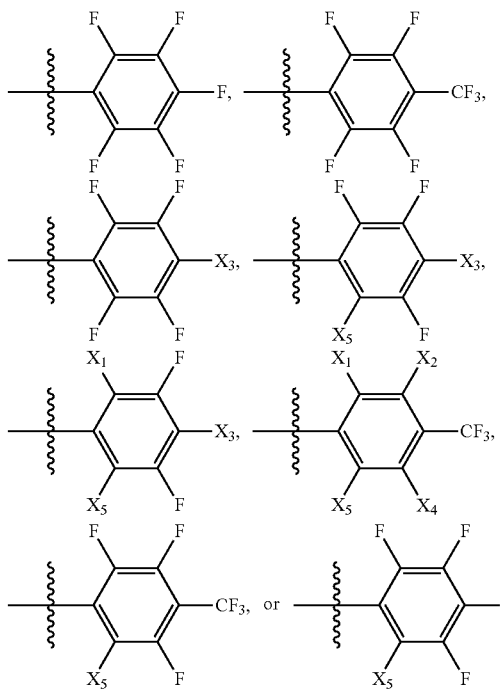

For example, each of $X_1$, $X_3$, and $X_5$, independently, can be methoxy, ethoxy, propoxy, butoxy, pentoxy, phenoxy, piperidinyl, or cyclooctenamino.

In certain circumstances, the compound can have formula (I) or formula (II)

$$P\text{-}Pip_xOR_yF_z \quad (I)$$

$$P\text{-}Pip_xOPh_wF_z \quad (II)$$

wherein P is a perfluoroarylsulfonimide anion, Pip is a piperidine, OR is an alkoxide, F is a fluorine substituent, OPh is phenoxide, and each of x, y, z and w, independently, is 0, 1, 2 or 3, wherein the sum of x, y, and z or x, z and w is 0, 1, 2 or 3.

In certain circumstances OR is methoxy, ethoxy, isopropoxy or neopentoxy.

In another aspect, an energy storage device comprising an electrolyte including the composition including:

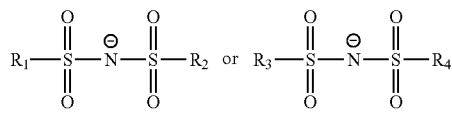

wherein $R_1$ is —$CF_3$ or a fluorinated phenyl and $R_2$ is a fluorinated phenyl or $R_3$ is —$CF_3$ or a fluorinated phenyl and $R_4$ is a fluorinated phenyl, wherein at least one of $R_3$ and $R_4$ is substituted by a nucleophile.

In another aspect, a method of making a sulfonamide comprising combining a sulfonamide and a sufonyl chloride according to equation (1)

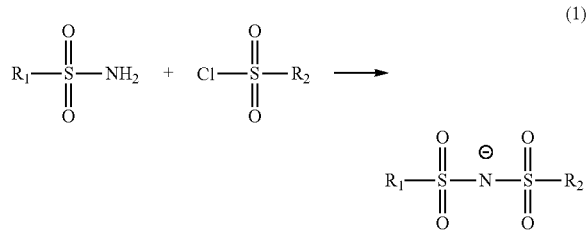

to form a first sulfonamide, wherein $R_1$ is —$CF_3$ or a fluorinated phenyl and $R_2$ is a fluorinated phenyl. In certain circumstances, the method can include exposing the first sulfonamide to a nucleophile according to equation (2)

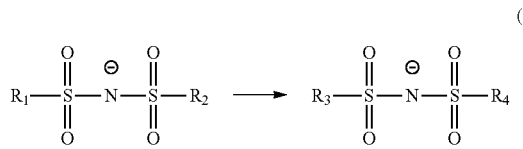

wherein $R_3$ is —$CF_3$ or a fluorinated phenyl and $R_4$ is a fluorinated phenyl, wherein at least one of $R_3$ and $R_4$ is substituted by the nucleophile.

Other aspects, embodiments, and features will be apparent from the following description, the drawings, and the claims.

BRIEF DESCRIPTION OF THE DRAWINGS

FIG. 6A shows the current response of A-OR$_y$F$_z$ as functions of time show very low current up to 4.5 Vi. FIG. 6B shows the current response of different types of alkoxide substitutions in A-OR$_3$F$_2$ compared. FIG. 6C shows the cumulative charge and estimated oxidized percentage of A-OR$_y$F$_z$ and A-OR$_3$F$_2$ calculated. FIGS. 6D and 6E respectively show the current response of salts with different numbers of piperidine type substitutions, A-Pip$_x$OR$_y$F$_z$, and those in the A-PipOR$_2$F$_2$ series recorded. FIG. 6F shows their cumulative charge and estimated oxidized percentage.

DETAILED DESCRIPTION

Figure 1:
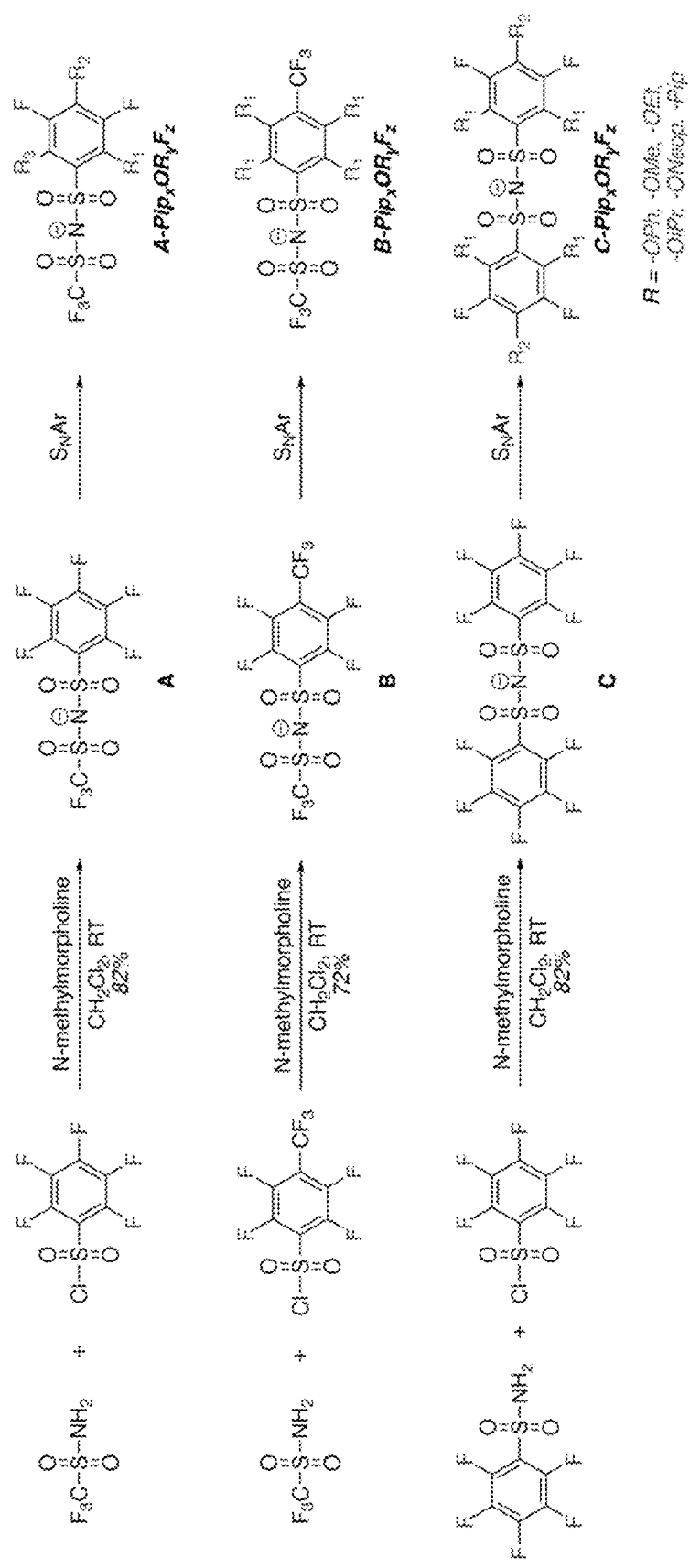
FIG. 1 shows synthesis of perfluoroarylsulfonimide anions A, B, and C and their subsequent functionalization via $S_NAr$ reactions to generate FAST anions of the general formula $P\text{-}Pip_xOR_yF_z$.

Solid-state electrolytes are attracting great interest for their applications in potentially safe and stable high-capacity energy storage technologies. Lithium bis(trifluoromethanesulfonyl)imide (LiTFSI) is widely used as a lithium source, especially in solid-state polymer electrolytes, due to its solubility and excellent chemical and electrochemical stability. Unfortunately, chemically inert LiTFSI cannot be easily modified to optimize its properties or allow for conjugation to other molecules, polymers, or substrates to prepare single-ion conducting polymer electrolytes. Chemical modifications of TFSI often erode its advantageous properties.

Disclosed herein is a class of modular TFSI analogs, Fluorinated Aryl Sulfonamide Tags (FAST), that are derived from successive nucleophilic aromatic substitution (S$_N$Ar) reactions of perfluoroarylsulfonimides and the synthesis, chemical and electrochemical stability and conductivity study of FAST. The tunable chemical and oxidative stability as well as Lewis basicity of FAST salts opens up new opportunities for the design and applications of polymer-FAST conjugates and single-ion conductors in solid-state electrolytes for safe and stable high-energy storage technologies.

Experimental studies and density functional theory calculations were used to assess the electrochemical oxidative stability, chemical stability, and degree of ion dissociation of FAST salts as a function of their structure. FAST salts offer a platform for accessing functional sulfonimides without sacrificing the advantageous properties of TFSI.

The high energy density, reliability, and low cost of rechargeable lithium-ion batteries (LIBs) have revolutionized the consumer market for portable electronic devices. See J. M. Tarascon and M. Armand, *Nature*, 2001, 414, 359-367, and S. Adv MaterAngewandte Chemie-International Edition in EnglishChem Soc RevChu and A. Majumdar, *Nature*, 2012, 488, 294-303, each of which is incorporated by reference in its entirety. However, the increasing demands of modern electronics necessitate the development of energy storage devices that feature greater power and energy densities without compromising affordability and safety. See O. Schmidt, A. Hawkes, A. Gambhir and I. Staffell, *Nat. Energy*, 2017, 6, 17110, A. Manthiram, X. Yu and S. Wang, *Nat. Rev. Mater.*, 2017, 2, 16103, and N. Nitta, F. Wu, J. T. Lee and G. Yushin, *Mater. Today*, 2015, 18, 252-264, each of which is incorporated by reference in its entirety. As LIBs approach the theoretical specific energies of cathode/anode materials, extensive studies have focused on finding new battery chemistries beyond LIBs. See D. Larcher and J. M. Tarascon, *Nat. Chem.*, 2015, 7, 19-29, which is incorporated by reference in its entirety. Two tantalizing options are lithium-air (Li-air) batteries and lithium-sulfur (Li—S) batteries. See A. C. Luntz and B. D. McCloskey, *Chem. Rev.*, 2014, 114, 11721-11750, Y.-C. Lu, B. M. Gallant, D. G. Kwabi, J. R. Harding, R. R. Mitchell, M. S. Whittingham and Y. Shao-Horn, *Energy Environ. Sci.*, 2013, 6, 750-768, D. Aurbach, B. D. McCloskey, L. F. Nazar and P. G. Bruce, *Nat. Energy,* 2016, 1, 16128, Q. Pang, X. Liang, C. Y. Kwok and L. F. Nazar, *Nat. Energy,* 2016, 1, 16132, Y. X. Yin, S. Xin, Y. G. Guo and L. J. Wan, *Angew. Chem. Int. Ed.*, 2013, 52, 13186-13200, and A. Manthiram, S. H. Chung and C. Zu, *Adv. Mater.*, 2015, 27, 1980-2006, each of which is incorporated by reference in its entirety. While the gravimetric theoretical energy densities of these battery technologies are several times higher than conventional LIBs, both face numerous challenges that must be addressed before commercialization. See A. C. Luntz and B. D. McCloskey, *Chem. Rev.*, 2014, 114, 11721-11750, Q. Pang, X. Liang, C. Y. Kwok and L. F. Nazar, *Nat. Energy,* 2016, 1, 16132, Y. X. Yin, S. Xin, Y. G. Guo and L. J. Wan, *Angew. Chem. Int. Ed.*, 2013, 52, 13186-13200, A. Manthiram, S. H. Chung and C. Zu, *Adv. Mater.*, 2015, 27, 1980-2006, J. Yi, S. Guo, P. He and H. Zhou, *Energy Environ. Sci.*, 2017, 10, 860-884, S. Zhang, K. Ueno, K. Dokko and M. Watanabe, *Adv. Energy Mater.*, 2015, 5, 1500117, and D. G. Kwabi, N. Ortiz-Vitoriano, S. A. Freunberger, Y. Chen, N. Imanishi, P. G. Bruce and Y. Shao-Horn, *MRS Bull,* 2014, 39, 443-452, each of which is incorporated by reference in its entirety. For example, new Li-air and Li—S batteries electrolytes with high conductivity ($>10^{-4}$ S/cm at room temperature), stability, and safety are needed. See A. C. Luntz and B. D. McCloskey, *Chem. Rev.*, 2014, 114, 11721-11750, J. Yi, S. Guo, P. He and H. Zhou, *Energy Environ. Sci.*, 2017, 10, 860-884, S. Zhang, K. Ueno, K. Dokko and M. Watanabe, *Adv. Energy Mater.*, 2015, 5, 1500117, and K. Xu, *Chem. Rev.*, 2014, 114, 11503-11618, each of which is incorporated by reference in its entirety. Most electrolyte materials that have been studied to date rely on mixtures of the salts lithium bis(trifluoromethanesulfonyl)imide (LiTFSI) or lithium hexafluorophosphate (LiPF$_6$) and a suitable solvent and/or polymer. See K. Xu, *Chem. Rev.*, 2014, 114, 11503-11618, and K. Xu, *Chem. Rev.*, 2004, 104, 4303-4418, each of which is incorporated by reference in its entirety. Comparing LiTFSI and LiPF$_6$, LiTFSI offers a broad electrochemical stability window, greater thermal stability, and higher resistance to hydrolysis, which lead it to be preferred in Li-air and Li—S batteries. See M. Ue, M. Takeda, M. Takehara and S. Mori, *J. Electrochem. Soc.*, 1997, 144, 2684-2688, and R. Younesi, G. M. Veith, P. Johansson, K. Edstrom and T. Vegge, *Energy Environ. Sci.*, 2015, 8, 1905-1922, each of which is incorporated by reference in its entirety. Additionally, due to its high solubility in water (>21 M) and ability to form a passivation layer (mainly LiF), LiTFSI has been used in "water-in-salt" electrolytes enabling high-voltage aqueous lithium-ion batteries. See L. Suo, F. Han, X. Fan, H. Liu, K. Xu and C. Wang, *J. Mater. Chem. A,* 2016, 4, 6639-6644, and L. Suo, O. Borodin, T. Gao, M. Olguin, J. Ho, X. Fan, C. Luo, C. Wang and K. Xu, *Science,* 2015, 350, 938-943, each of which is incorporated by reference in its entirety. Moreover, encouraging results have been reported on utilizing TFSI salts in sodium-air batteries and multivalent energy storage systems such as magnesium batteries. See M. He, K. C. Lau, X. Ren, N. Xiao, W. D. McCulloch, L. A. Curtiss and Y. Wu, *Angew. Chem. Int. Ed.*, 2016, 55, 15310-15314, and X. Qu, Y. Zhang, N. N. Rajput, A. Jain, E. Maginn and K. A. Persson, *J. Phys. Chem. C,* 2017, 121, 16126-16136, each of which is incorporated by reference in its entirety.

Though great progress has been made on the development of solid polymer electrolytes wherein LiTFSI is dissolved in an aprotic polymer matrix of poly(ethylene oxide) (PEO), the transference number of Li$^+$ in such materials is typically as low as 0.2, which leads to polarization at the battery electrodes and deleterious effects such as dendrite growth and limited power delivery. See K. Timachova, H. Watanabe and N. P. Balsara, *Macromolecules,* 2015, 48, 7882-7888, R. Bouchet, S. Maria, R. Meziane, A. Aboulaich, L. Lienafa, J.-P. Bonnet, T. N. T. Phan, D. Bertin, D. Gigmes, D. Devaux, R. Denoyel and M. Armand, *Nat. Mater.*, 2013, 12, 452-457, E. Quartarone and P. Mustarelli, Chem. Soc. Rev., 2011, 40, 2525-2540, Z. Xue, D. He and X. Xie, *J. Mater. Chem. A,* 2015, 3, 19218-19253, W. H. Meyer, *Adv. Mater.*, 1998, 10, 439-448, and A. Manthiram, X. Yu and S. Wang, *Nat. Rev. Mater.*, 2017, 2, 16103, each of which is incorporated by reference in its entirety. One strategy to improve the Li$^+$ (or Na$^+$ in sodium batteries) transference number involves anchoring the anions to a polymeric backbone, making the cation the only mobile ion (i.e., single-ion conducting polymer electrolytes). See K. M. Diederichsen, E. J. McShane and B. D. McCloskey, *ACS Energy Lett.,* 2017, 2, 2563-2575, which is incorporated by reference in its entirety. Unfortunately, the TFSI anion is not readily chemically modifiable, and attempts to attach sulfonimides to polymers via replacement of one or both of the electron withdrawing trifluoromethyl groups of TFSI with phenyl or alkyl groups often lead to materials with inferior properties compared to TFSI. See R. Bouchet, S. Maria, R. Meziane, A. Aboulaich, L. Lienafa, J.-P. Bonnet, T. N. T. Phan, D. Bertin, D. Gigmes, D. Devaux, R. Denoyel and M. Armand, *Nat. Mater.*, 2013, 12, 452-457, H. T. Ho, A. Tintaru, M. Rollet, D. Gigmes and T. N. T. Phan, *Polym. Chem.,* 2017, 8, 5660-5665, L. Porcarelli, A. S. Shaplov, F. Bella, J. R. Nair, D. Mecerreyes and C. Gerbaldi, *ACS Energy Lett.,* 2016, 1, 678-682, Q. Ma, H. Zhang, C. Zhou, L. Zheng, P. Cheng, J. Nie, W. Feng, Y. S. Hu, H. Li, X. Huang, L. Chen, M. Armand and Z. Zhou, *Angew. Chem. Int. Ed.*, 2016, 55, 2521-2525, and P. Murmann, P. Niehoff, R. Schmitz, S. Nowak, H. Gores, N. Ignatiev, P. Sartori, M. Winter and R. Schmitz, *Electrochim. Acta,* 2013, 114, 658-666, each of which is incorporated by reference in its entirety. Indeed, replacement of a trifluoromethyl group from TFSI with an electron rich group would be expected to decrease the electrochemical oxidative stability of the resulting salt, increase Li$^+$-anion association, and potentially reduce ion conductivity. See S. Ladouceur, S. Paillet, A. Vijh, A. Guerfi, M. Dontigny and K. Zaghib, *J. Power Sources,* 2015, 293, 78-88, V. Morizur, S. Olivero, J. R. Desmurs, P. Knauth and E. Duñach, *New J. Chem.,* 2014, 38, 6193-6197, and V. Morizur, M. Braglia, S. Olivero, J.-R. Desmurs, P. Knauth and E. Duñach, *New J. Chem.,* 2016, 40, 7840-7845, each of which is incorporated by reference in its entirety.

In certain embodiments, TFSI derivatives where one or both trifluoromethyl groups can be replaced with functional yet still electron withdrawing substituents, such that the beneficial properties of TFSI are not compromised. Perfluoroarylsulfonimides A, B, and C (FIG. 1) can be starting points to achieve this goal. Note that the cations used in this study, Na$^+$ and Li$^+$, are not shown in FIG. 1. The installation of perfluoroaryl substituents in these compounds can maintain the electron deficient nature of the anion and open the possibility of chemical modification via nucleophilic aromatic substitution (S$_N$Ar) reactions. Thereby a class of sulfonimides, which is called "Fluorinated Aryl Sulfonimide Tags" (FAST), can be synthesized. Successive S$_N$Ar reactions between A, B, or C and oxygen- and/or nitrogen-base nucleophiles enabled rational tuning of the electron density, electrochemical oxidative stability, chemical stability toward superoxide and peroxide anions, and Lewis basicity of FAST salts as assessed by both experimental studies and density functional theory (DFT) calculations. This design led to several FAST salts that display electrochemical oxidative stability at 4.0 VU, negligible chemical degradation, and reasonable ion conductivity in 1,2-dimethoxyethane (DME). FAST salts offer a synthetically tunable platform for the identification of optimal anion structures that could replace TFSI in a variety of applications.

In general, a composition can include:

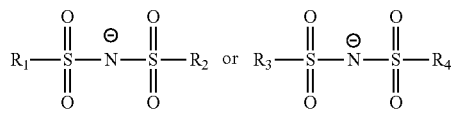

wherein $R_1$ is —$CF_3$ or a fluorinated phenyl and $R_2$ is a fluorinated phenyl or $R_3$ is —$CF_3$ or a fluorinated phenyl and $R_4$ is a fluorinated phenyl, wherein at least one of $R_3$ and $R_4$ is substituted by a nucleophile.

In certain embodiments, $R_1$ can be —$CF_3$.

In other embodiments, $R_1$ can be a fluorinated phenyl.

In certain embodiments, the fluorinated phenyl can have at least two fluorine groups, for example, the fluorinated phenyl can have a formula

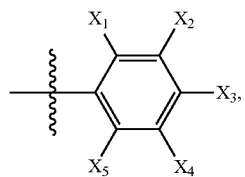

wherein each of $X_1$, $X_2$, $X_3$, $X_4$, and $X_5$, independently, is F or $CF_3$.

In other embodiments, the fluorinated phenyl can have a formula

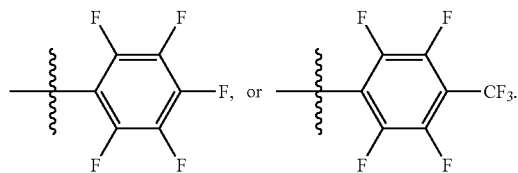

In certain embodiments, the compound has the formula

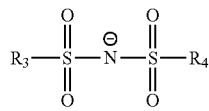

wherein $R_3$ can be —$CF_3$ or a fluorinated phenyl and $R_4$ can be a fluorinated phenyl, wherein at least one of $R_3$ and $R_4$ can be substituted by a nucleophile.

The nucleophile can be an amine, alkoxy, aryloxy, alkylthio, alkyl or similar nucleophilic moiety. For example, the nucleophile can be —$OR_a$ or —$NR_cR_d$, wherein $R_a$ is C1-C6 alkyl, benzalkyl, or substituted or unsubstituted phenyl, $R_b$ is C1-C6 alkyl, benzalkyl, or phenyl, $R_c$ is C1-C6 alkyl, benzalkyl, or phenyl, or $R_b$ and $R_c$ together form a three to eight membered ring.

In other embodiments, the fluorinated phenyl can have a formula

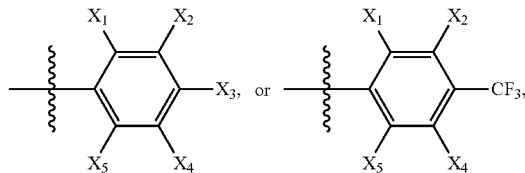

wherein each of $X_1$, $X_2$, $X_3$, $X_4$, and $X_5$, independently, is F, $OR_a$, or $NR_eR_d$, wherein $R_a$ is C1-C6 alkyl, benzalkyl, or substituted or unsubstituted phenyl, $R_b$ is C1-C6 alkyl, benzalkyl, or phenyl, $R_c$ is C1-C6 alkyl, benzalkyl, or phenyl, or $R_b$ and $R_c$ together form a three to eight membered ring.

In other embodiments, the fluorinated phenyl can have a formula

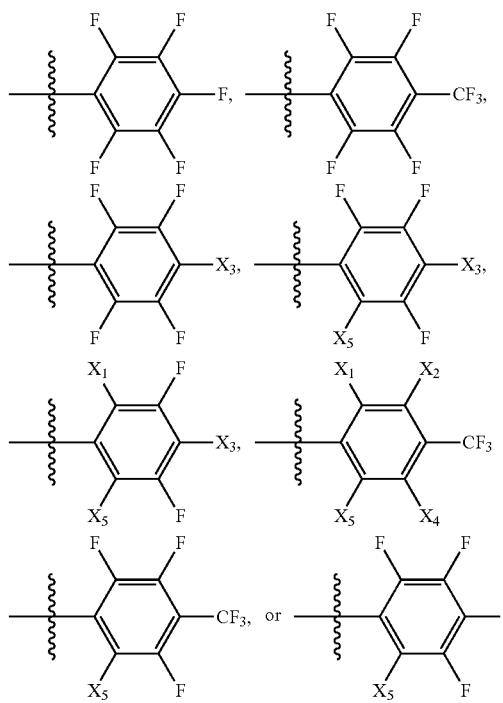

In certain examples, each of $X_1$, $X_3$, and $X_5$, independently, can be methoxy, ethoxy, propoxy, butoxy, pentoxy, phenoxy, piperidinyl, or cyclooctenamino.

The composition can be made by a number of methods. For example, a method of making a sulfonamide can include combining a sulfonamide and a sufonyl chloride according to equation (1)

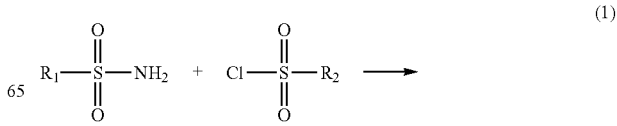

(1)

-continued

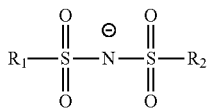

to form a first sulfonamide, wherein $R_1$ is —$CF_3$ or a fluorinated phenyl and $R_2$ is a fluorinated phenyl.

The method can include exposing the first sulfonamide to a nucleophile according to equation (2)

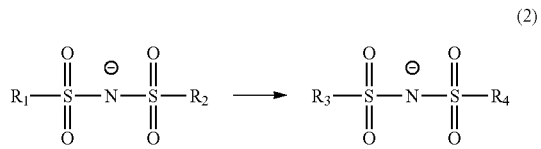 (2)

wherein $R_3$ is —$CF_3$ or a fluorinated phenyl and $R_4$ is a fluorinated phenyl, wherein at least one of $R_3$ and $R_4$ is substituted by the nucleophile.

In other aspects, an energy storage device can include an electrolyte including the composition disclosed herein.

An energy storage device can include a voltage source electrically connected to a first electrode and a second electrode; and an electrolyte in contact with the first electrode and the second electrode; wherein the electrolyte includes a composition of formula (I) or formula (II):

 (I)

 (II)

wherein P is a perfluoroarylsulfonimide anion, Pip is a piperidine, R is an alkoxide, F is a fluorine substituent, Ph is phenoxide, and x, y, z and w are the numbers of piperidine, alkoxide, fluorine and phenoxide substituents, respectively.

Where a system is described as involving a first electrode and/or a second electrode (one or both of which can include a catalytic material), with production of oxygen gas via water electrolysis at the first electrode and/or production of hydrogen gas at the second electrode, it is to be understood that the first electrode can facilitate oxidation of water or another species to produce oxygen gas or another oxidized product. Examples of reactants that can be oxidized in this context can include methanol, formic acid, ammonia, etc. Examples of oxidized products can include $CO_2$, $N_2$, etc. At the second electrode, a reaction can be facilitated in which water (or hydrogen ions) is reduced to make hydrogen gas, but it is to be understood that a variety of reactants not limited to water (e.g., metal oxides or ions, acetic acid, phosphoric acid, etc.) can be reduced to form hydrogen gas and/or metals and/or other products of the reduction reaction (e.g., metal hydroxides, acetate, phosphate, etc.). This reaction at the second electrode can be run in reverse, in "fuel cell" operation, such that hydrogen gas (and/or other exemplary products noted above) is oxidized to form water (and/or other exemplary reactants noted above). In some cases, the compositions, electrodes, methods, and/or systems may be used for reducing hydrogen gas. In some cases, the compositions, electrodes, methods, and/or systems may be used in connection with a photoelectrochemical cell.

Electrolytic devices, fuel cells, metal-ion batteries (e.g. lithium-ion batteries) and metal-air batteries (e.g. lithium-air batteries) are non-limiting examples of energy storage devices provided herein. Energy can be supplied to electrolytic devices by photovoltaic cells, wind power generators, or other energy sources.

An energy storage device may be combined with additional energy storage device to form a larger device or system. This may take the form of a stack of devices or subsystems (e.g., fuel cell and/or electrolytic device and/or metal-air battery) to form a larger device or system. Various components of a device, such as the electrodes, power source, electrolyte, separator, container, circuitry, insulating material, gate electrode, etc. can be fabricated by those of ordinary skill in the art from any of a variety of components, as well as those described in any of those patent applications described herein. Components may be molded, machined, extruded, pressed, isopressed, infiltrated, coated, in green or fired states, or formed by any other suitable technique.

Those of ordinary skill in the art are readily aware of techniques for forming components of devices herein.

Generally speaking, an energy storage device includes two electrodes (i.e., an anode and a cathode) in contact with an electrolyte. The electrodes are electrically connected to one another; the electrical connection can, depending on the intended use of the system, include a power source (when the desired electrochemical reactions require electrical energy) or an electrical load (when the desired electrochemical reactions produce electrical energy). An energy storage device can be used for producing, storing, or converting chemical and/or electrical energy.

Figure 45:
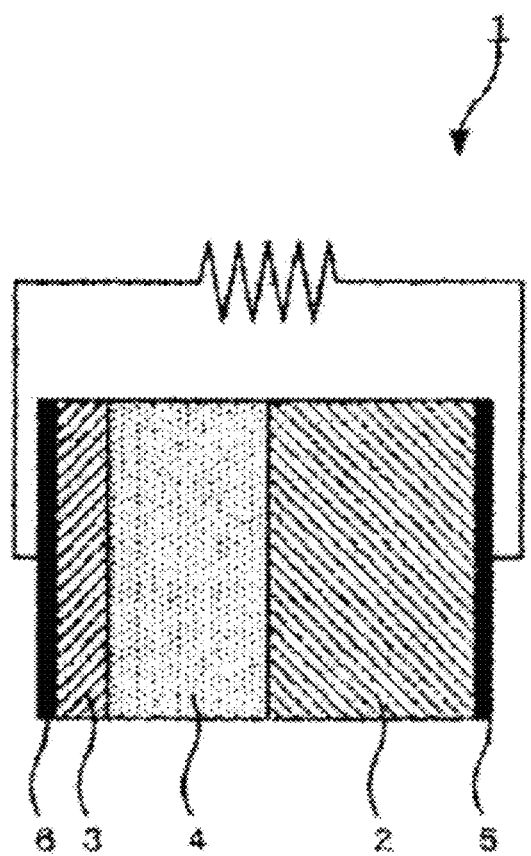
FIG. 45 shows schematic illustration of an energy storage device.

FIG. 45 schematically illustrates energy storage device 1, which includes anode 2, cathode 3, electrolyte 4, anode collector 5, and cathode collector 6. The battery can include a housing including an electrolyte (not shown). The battery can be a lithium battery, for example, a lithium ion battery.

Examples

Figure 2:
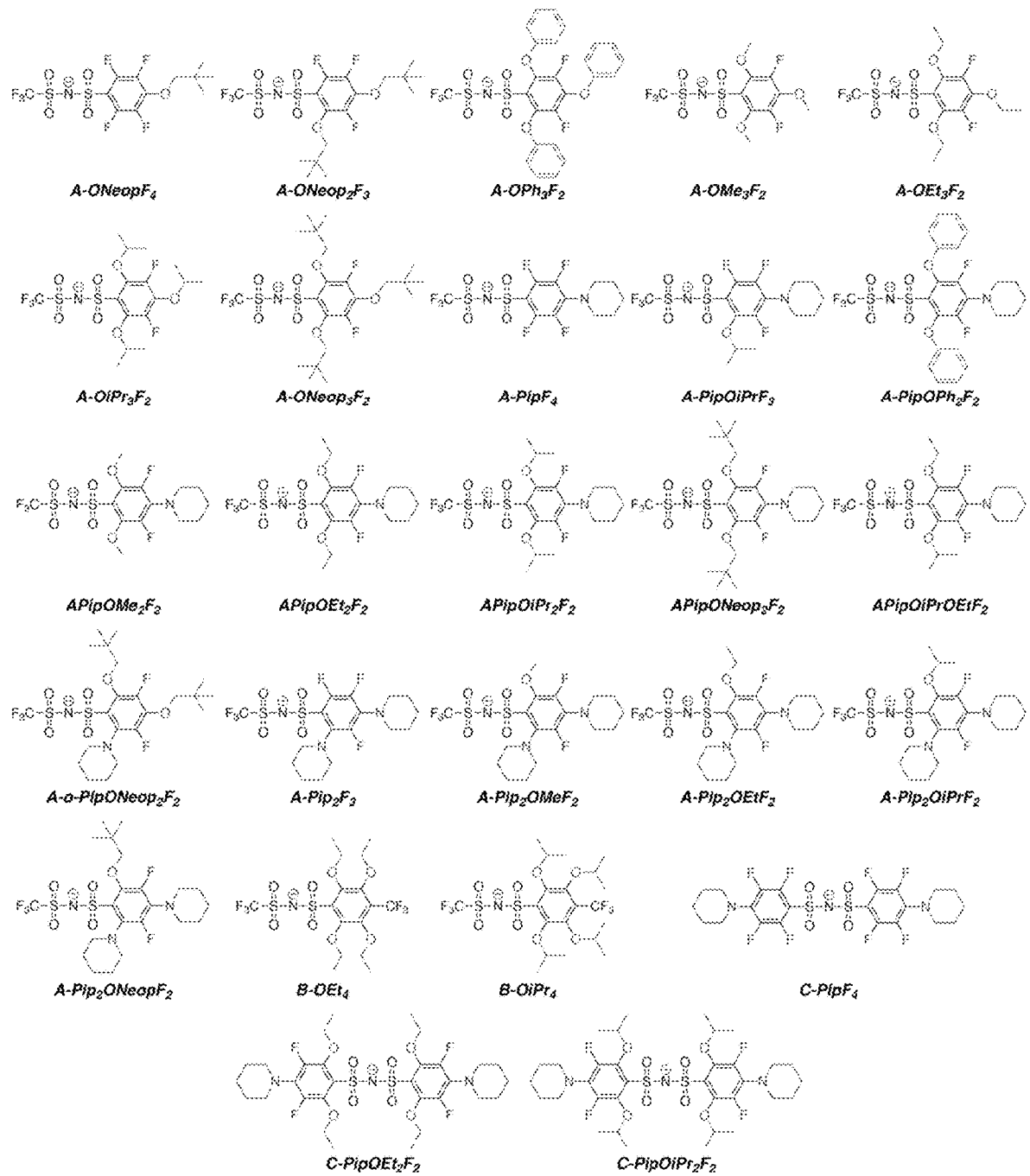
FIG. 2 shows chemical structures of FAST anions synthesized in this work via $S_NAr$ reactions between various nucleophiles and parent salts A, B, or C.

The perfluoroarylsulfonimide sodium salts A and C were prepared starting from pentafluorobenzene sulfonyl chloride in good yield (>82%), whereas salt B was prepared via condensation of 4-trifluoromethyl-2,3,5,6-tetrafluorobenzenesulfonyl bromide (see V. E. Platonov, A. M. Roman A. Bredikhin and V. V. K. Maksimov, *J. Fluorine Chem.*, 2010, 131, 13-16, which is incorporated by reference in its entirety) and trifluoromethanesulfonamide in 72% yield. With these compounds in hand, the synthesis of a library of FAST salts (FIG. 2) were started via $S_NAr$ reactions between A, B, or C and a variety of nucleophiles selected to assess the impact of steric bulk and electronics on the properties of FAST salts: phenoxide (OPh), alkoxides (OR: OMe, OEt, OiPr, and ONeop), and piperidine (Pip). Throughout this work, the general notation P-Pip$_x$OR$_y$F$_z$ represents each FAST salt, where P is the parent salt (A, B, or C), and x, y, and z are the numbers of piperidine, alkoxide, and fluorine substituents, respectively. All FAST sodium salts were characterized by $^1H$, $^{13}C$, $^{19}F$ NMR, MS, and in some cases, single crystal X-ray crystallography.

Figure 3A:
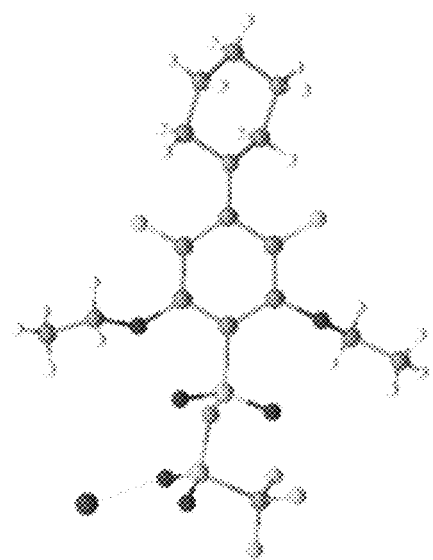
FIGS. 3A-3C show crystal structures of FAST-Na salts A-PipOPh$_2$F$_2$(FIG. 3A), A-PipOMe$_2$F$_2$(FIG. 3B) and A-PipOEt$_2$F$_2$(FIG. 3C). Atom color code: grey—carbon, white—hydrogen, red—oxygen, green—fluorine, yellow—sulfur, purple—nitrogen, and magenta—sodium.
Figure 3B:
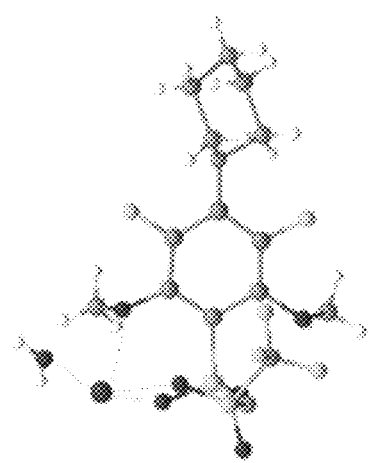
Figure 3C:
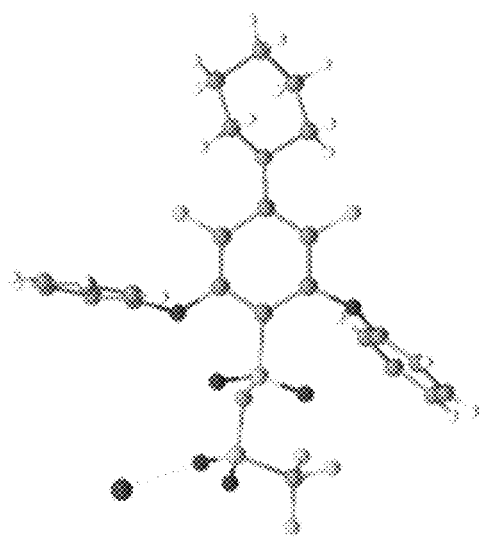
Figure 10:
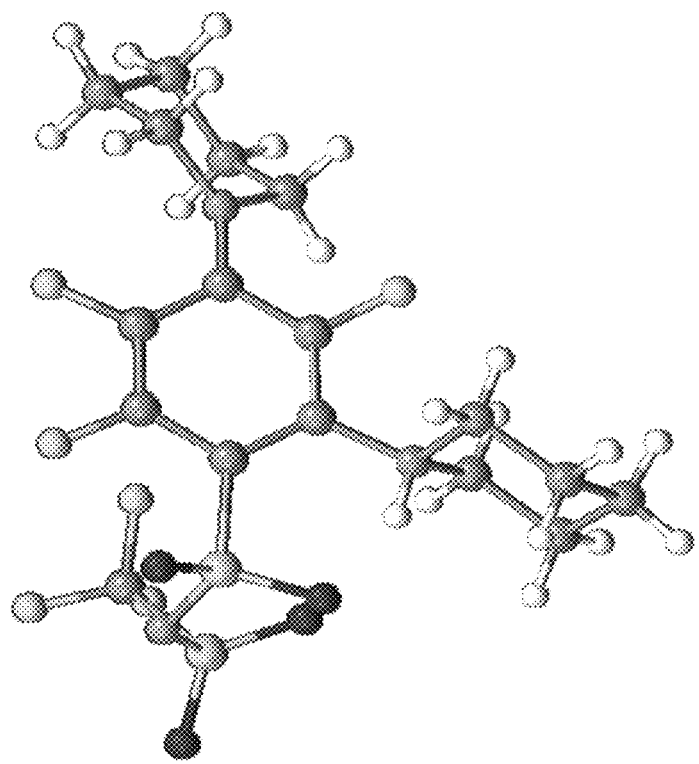
FIG. 10 shows crystal structures of A-Pip$_2$F$_3$●H$^+$.

Differences in the reactivity of the various nucleophiles in this system were exploited to control the substituent patterns in the resulting FAST salts. For example, selective $S_NAr$ of the para fluorine atom of A with Pip could be achieved to provide A-PipF$_4$; subsequent $S_NAr$ of the remaining ortho fluorine atoms with OPh, OMe, or OEt groups provided A-PipOPh$_2$F$_2$, A-PipOMe$_2$F$_2$ and A-PipOEt$_2$F$_2$, respectively. The structures of the sodium salts of these compounds were confirmed by X-ray crystallography (FIG. 3). Notably, though these newly introduced N and O substituents are electron donating, this substitution pattern maintains the two electron-withdrawing meta fluorine substituents (Hammett parameters for fluorine: $\sigma_{meta}$=0.34 versus $\sigma_{para}$=0.06). As seen in FIG. 3, the sulfonimides in these structures are present as their free base; the sodium cations are not coordinated to the nitrogen but instead coordinate to the oxygen atoms from the sulfonimide groups, alkoxide groups, and/or adventitious water (FIG. 3B). When two piperidine groups are introduced onto the A scaffold the resulting FAST salts (e.g., A-Pip$_2$F$_3$ and its derivatives A-Pip$_2$ORF$_2$) are much less acidic (they are protonated during aqueous washing); the crystal structure of A-Pip$_2$F$_3$●H$^+$ (FIG. 10) reveals that the proton is coordinated by the nitrogen atom of the ortho-Pip. Therefore, FAST salts containing two Pip substituents were deprotonated with sodium hydroxide prior to further investigations.

Figure 4:
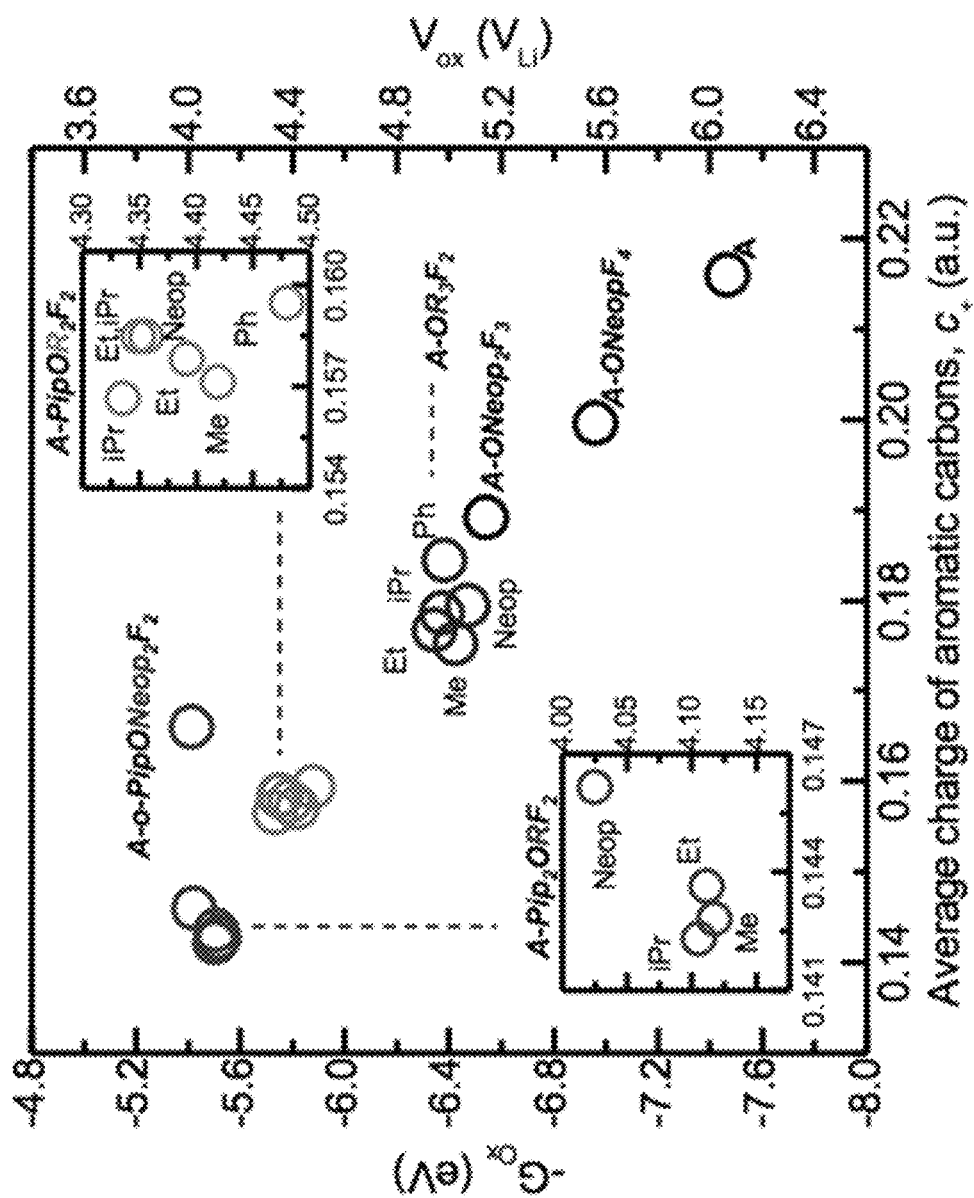
FIG. 4 shows electrochemical oxidative potentials of select FAST salts computed using B3LYP/6-311++G(d,p) with geometries fully optimized at the B3YLP/6-31G(d,p) level of theory in implicit DMSO solvent are plotted against the arithmetic average of the NPA partial charges of aromatic carbons obtained at the optimized geometries.

The electrochemical oxidative stability and average partial charge of aromatic carbons, $c_+$, obtained using Natural Population Analysis (NPA) (see J. P. Foster and F. Weinhold, *J. Am. Chem. Soc.*, 1980, 102, 7211-7218, and A. E. Reed, R. B. Weinstock and F. Weinhold, *J. Chem. Phys.*, 1985, 83, 735-746, each of which is incorporated by reference in its entirety) of select tri-substituted FAST salts as well as A, A-NeopF$_4$, and A-Neop$_2$F$_3$ depicted in FIG. 2 were evaluated using DFT calculations (FIG. 4) following the BANE framework developed recently. See S. Feng, M. Chen, L. Giordano, M. Huang, W. Zhang, C. V. Amanchukwu, R. Anandakathir, Y. Shao-Horn and J. A. Johnson, *J. Mater. Chem. A*, 2017, 5, 23987-23998, which is incorporated by reference in its entirety. In FIG. 4, the electrochemical oxidation potentials in experimentally measured scale versus Li/Li$^+$, plotted on the right axis, were converted from the computed -G$_{ox}$ in eV by the subtraction of 1.4 V. See S. Trasatti, *Pure Appl. Chem.*, 1986, 58, 955-966, and L. Xing, O. Borodin, G. D. Smith and W. Li, *J. Phys. Chem. A*, 2011, 115, 13896-13905, each of which is incorporated by reference in its entirety.

Higher computed electrochemical oxidation potential correlated well with higher average aromatic carbon charge, $c_+$. More specifically, FAST salts with the greatest number of electron donating Pip groups (e.g., A-Pip$_2$ORF$_2$) exhibit the lowest $c_+$ and electrochemical oxidative stability. FAST derivatives with one Pip group (e.g., A-PipOR$_2$F$_2$) showed higher $c_+$ and electrochemical oxidative stability than A-Pip$_2$ORF$_2$. As expected, the trialkoxide derivatives A-OR$_3$F$_2$, in turn, exhibited higher $c_+$ and electrochemical oxidative stability than A-PipOR$_2$F$_2$. Finally, in the order of A-Neop$_2$F$_3$, A-NeopF$_4$, and A, as the number of electron withdrawing F atoms increases, the computed $c_+$ and electrochemical oxidative stability increase almost linearly.

Figure 5:
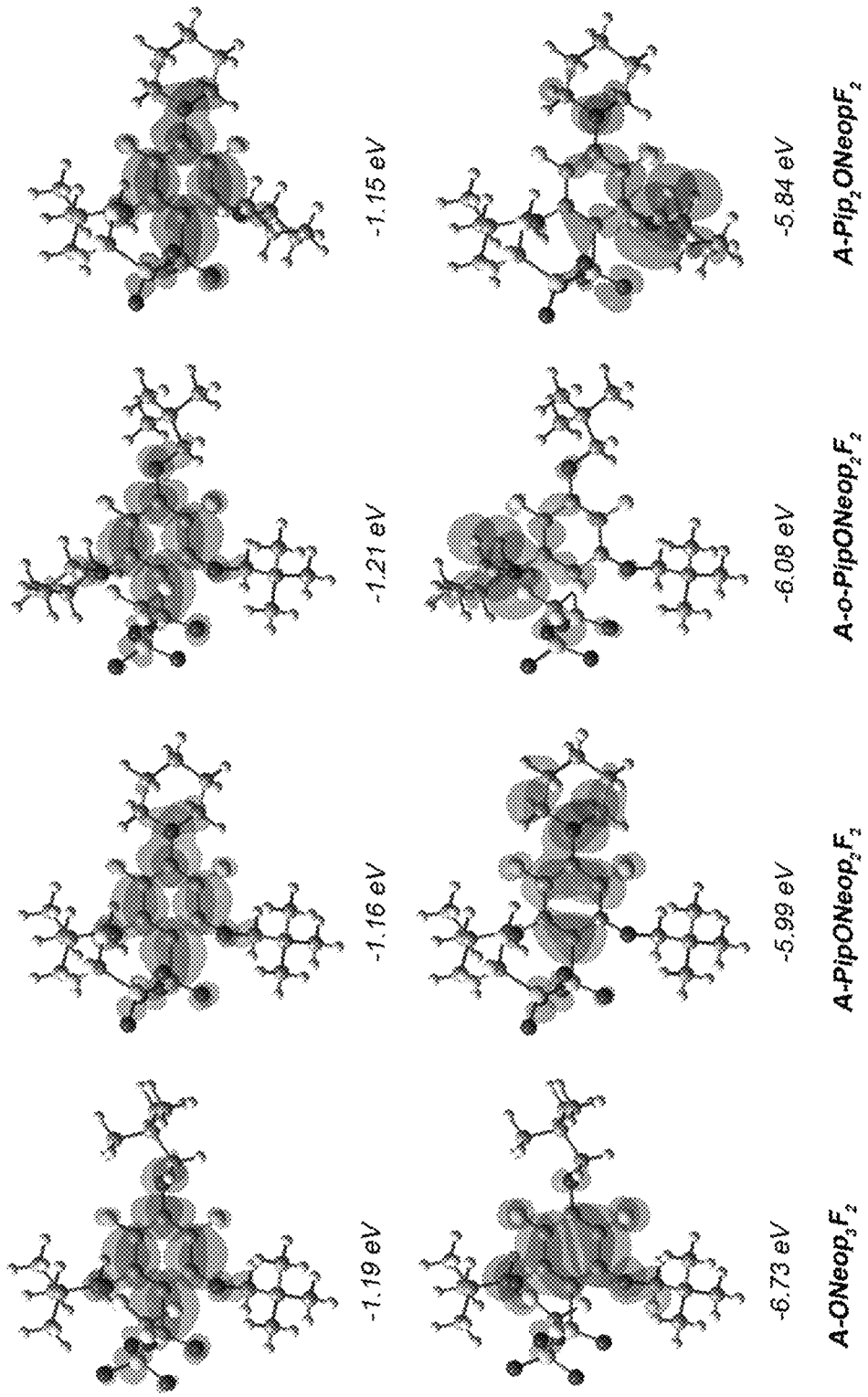
FIG. 5 shows computed LUMOs (top row) and HOMOs (bottom row) of four representative FAST anions.

To further understand the electrochemical oxidative stability of the FAST salts, HOMO and LUMO maps for four representative salts, A-ONeop$_3$F$_2$, A-PipONeop$_2$F$_2$, A-o-PipONeop$_2$F$_2$, and A-Pip$_2$ONeopF$_2$ were compared (FIG. 5). The HOMO/LUMO maps were generated using the optimized geometries obtained at B3LYP/6-31G(d,p). The HOMO/LUMO energy in eV were obtained at B3LYP/6-311++G(d,p) level of theory with geometries optimized using B3LYP/6-31G(d,p). Atom color code: grey—carbon, white—hydrogen, red—oxygen, aqua—fluorine, yellow—sulfur, and blue—nitrogen.

These salts show similar LUMOs but significantly different HOMOs: the HOMO of A-ONeop$_3$F$_2$ is uniformly distributed on the aromatic ring with little density on the oxygen atoms of the alkoxide substituents. FAST salts with a Pip group featured HOMOs that were heavily localized on the Pip nitrogen atom. Surprisingly, the HOMO maps of A-PipONeop$_2$F$_2$ and A-o-PipONeop$_2$F$_2$ are drastically different. The HOMO of A-Pip$_2$ONeopF$_2$ is distributed on both the benzene ring and the Pip nitrogen atom, while nearly all the HOMO is concentrated on the Pip nitrogen atom in the ortho position in both A-o-PipONeop$_2$F$_2$ and A-Pip$_2$ONeopF$_2$. These observations may explain the observed basicity of A-o-PipONeop$_2$F$_2$ and A-Pip$_2$ONeopF$_2$ that was not observed for other salts.

Experimental measurements were carried out to evaluate the electrochemical oxidative stability of several of these FAST salts under an oxygenated environment for comparison to the DFT computed trends obtained in implicit DMSO solvent. The electrochemical oxidative stability of the FAST salts was determined using potentiostatic measurements in an electrochemical cell (glass fiber separator impregnated with 0.02 M sulfonimide dissolved in propylene carbonate (PC) solution sandwiched between Li metal foil and stainless steel mesh current collector), which was pressurized with oxygen and held at potentials from 3.0 to 4.5 $V_{Li}$ for 3 h each. PC was chosen as the solvent due to its superior electrochemical stability (see K. Xu, *Chem. Rev.*, 2004, 104, 4303-4418, and M. Ue, M. Takeda, M. Takehara and S. Mori, *J. Electrochem. Soc.*, 1997, 144, 2684-2688, each of which is incorporated by reference in its entirety), although it should be noted that its vulnerability against nucleophilic substitution makes it unsuitable as electrolyte solvent for Li—O$_2$ battery. See D. Aurbach, M. Daroux, P. Faguy and E. Yeager, *J. Electroanal. Chem.*, 1991, 297, 225-244, and S. A. Freunberger, Y. Chen, Z. Peng, J. M. Griffin, L. J. Hardwick, F. Barde, P. Novak and P. G. Bruce, *J. Am. Chem. Soc.*, 2011, 133, 8040-8047, each of which is incorporated by reference in its entirety. A relatively low concentration, 0.02 M, was employed to accommodate the low solubility of several FAST salts such as A-Pip$_2$OEtF$_2$ in PC. The current response, cumulative charge, and estimated percentage of salt oxidation at each potential step from 3.6 $V_{Li}$ to 4.5 $V_{Li}$ for select salts are shown in FIG. 6. Measurements were performed using an electrochemical cell pressurized with oxygen and consisting of a stainless steel mesh current collector, 90 μL 0.02 M FAST-PC solution, one glass fiber separator, and Li metal.

Figure 6C:
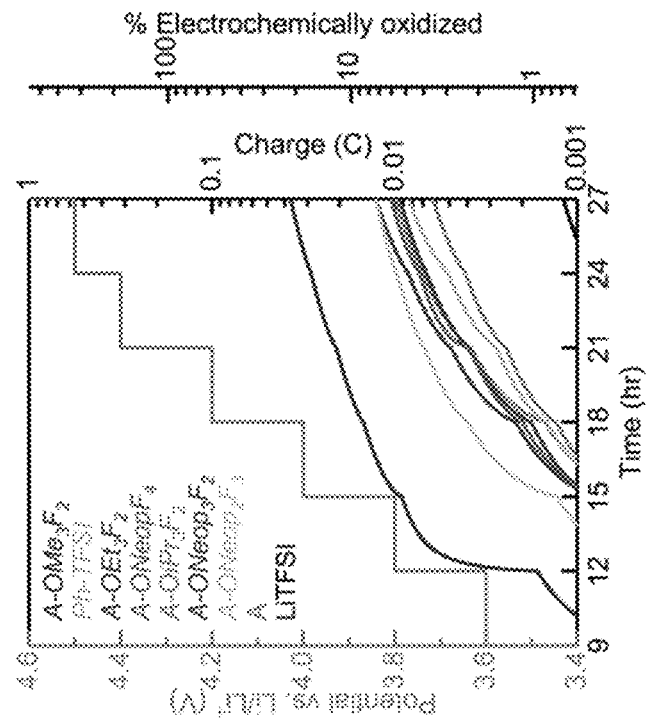
FIGS. 6A-6F show the influence of $S_NAr$ substitutions on the electrochemical oxidative stability of representative FAST salts in potentiostatic tests.
Figure 6B:
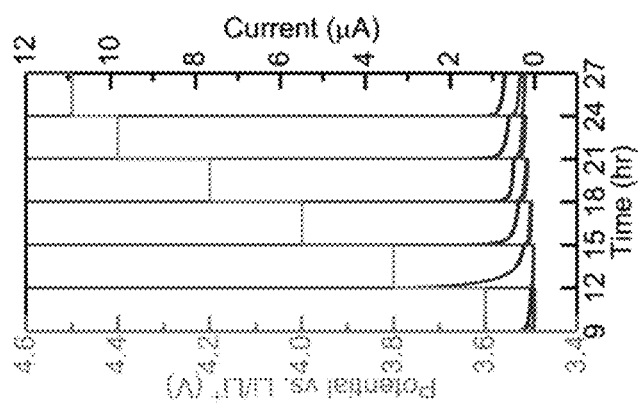
Figure 6A:
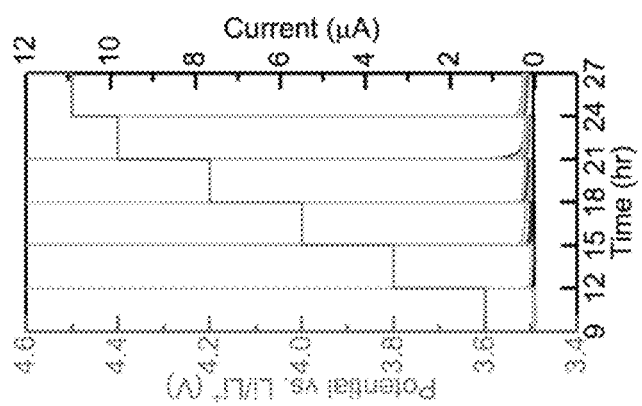
Figure 6F:
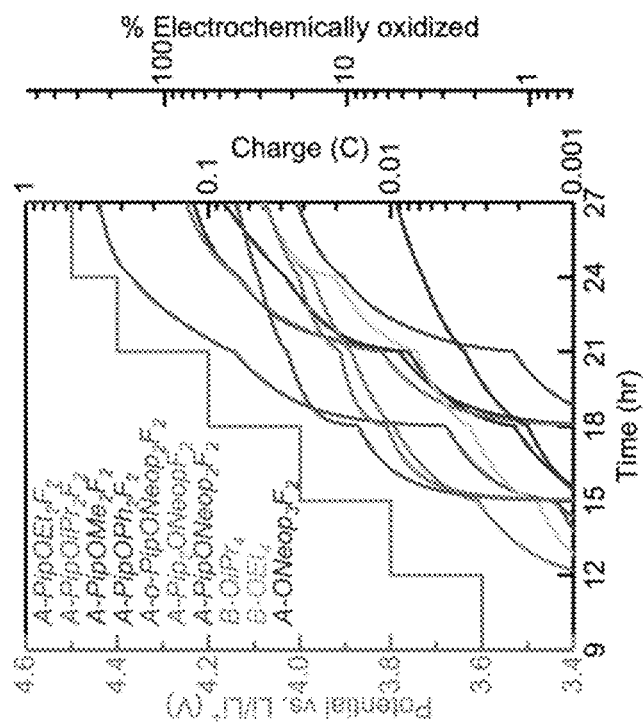
Figure 6E:
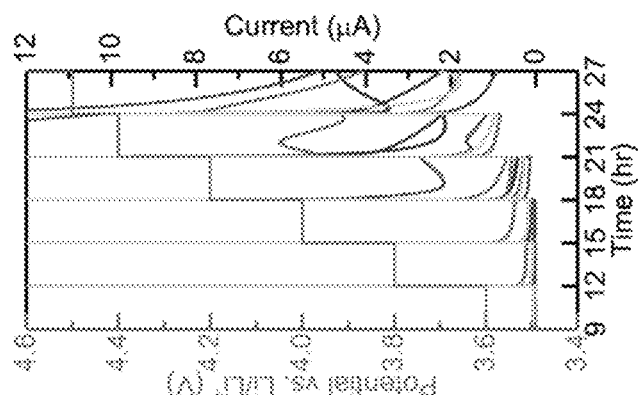
Figure 6D:
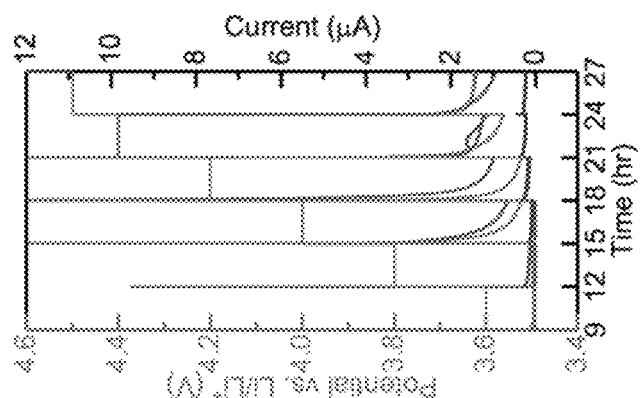

The percentage of electrochemically oxidized salt was calculated based on the assumption that the oxidation of one FAST salt molecule produces one electron. Deviation from this assumption and the presence of impurities can lead to overestimation of the electrochemical oxidation percentage, which can explain why several salts showed electrochemical oxidation percentages that are close to or even greater than 100%. In FIGS. 6A and 6C, the series of A, A-ONeopF$_4$, A-ONeop$_2$F$_3$, A-ONeop$_3$F$_2$ are compared. All four salts in this series, which feature 2 to 5 fluorine atoms and 0 to 3 ONeop substituents on the aromatic ring, were very stable towards oxidation with approximately 2% and 6% oxidized upon charging to 4.2 V and 4.5 $V_{Li}$, respectively (FIG. 6C). Upon charging to 4.5 V, TFSI exhibited electrochemical oxidation roughly an order of magnitude lower than the four salts in this series. However, these fours salts are more stable than (phenylsulfonyl)(trifluoromethyl)sulfonimide (Ph-TFSI), a widely used TFSI alternative in battery applications. See R. Bouchet, S. Maria, R. Meziane, A. Aboulaich, L. Lienafa, J.-P. Bonnet, T. N. T. Phan, D. Bertin, D. Gigmes, D. Devaux, R. Denoyel and M. Armand, *Nat. Mater.*, 2013, 12, 452-457, and A. A. Rojas, K. Thakker, K. D. McEntush, S. Inceoglu, G. M. Stone and N. P. Balsara, *Macromolecules*, 2017, 50, 8765-8776, each of which is incorporated by reference in its entirety. Next, the influence of the substitution pattern on the oxidative stability of triply substituted salts A-OR$_3$F$_2$ was measured (FIGS. 6B and 6C). These salts showed excellent oxidative stability at voltages <4.0 $V_{Li}$ with the exception of A-OMe$_3$F$_2$, which exhibited significant oxidative current at 3.8 $V_{Li}$. Generally, the FAST salts with bulkier alkoxide groups (e.g., OiPr and ONeop) exhibited superior stability than those with smaller substituents such as OMe and OEt at high voltage (>4.0 $V_{Li}$). The influence of Pip on the electrochemical stability was investigated by comparing A-ONeop$_3$F$_2$, A-PipONeop$_2$F$_2$, A-o-PipONeop$_2$F$_2$, and A-Pip$_2$ONeopF$_2$ (FIGS. 6D and 6F). It is observed that while A-ONeop$_3$F$_2$ is very stable at 4.2 $V_{Li}$ (~2% electrochemical oxidation), A-Pip$_2$ONeopF$_2$ and A-o-PipONeop$_2$F$_2$ experienced 11% and 21% oxidation upon charging to 4.2 $V_{Li}$, respectively. This stability trend matches the DFT calculations presented in FIG. 4 (A-ONeop$_3$F$_2$>A-PipONeop$_2$F$_2$>A-o-PipONeop$_2$F$_2$≈A-Pip$_2$ONeopF$_2$). Finally, several A type FAST salts with one piperidine group A-PipOR$_2$F$_2$ and B type FAST salts B—OR$_4$ were tested and compared in FIGS. 6E and 6F. As shown by the cumulative charge and estimated oxidized percentage in FIG. 6F, A-PipOR$_2$F$_2$ and B—OR$_4$ generally have higher charge accumulation and worse electrochemical oxidative stability than A-OR$_3$F$_2$ at >4.0 $V_{Li}$. Overall, most of the salts in FIG. 3 show electrochemical oxidative stability at 4.0 $V_{Li}$ and thus are promising candidates in diverse battery chemistries. Notably, A-ONeop$_3$F$_2$ was extremely stable to electrochemical oxidation (up to 4.5 $V_{Li}$ with oxidative current less than 0.25 μA and oxidation percentage is less than 6%).

Figure 7:
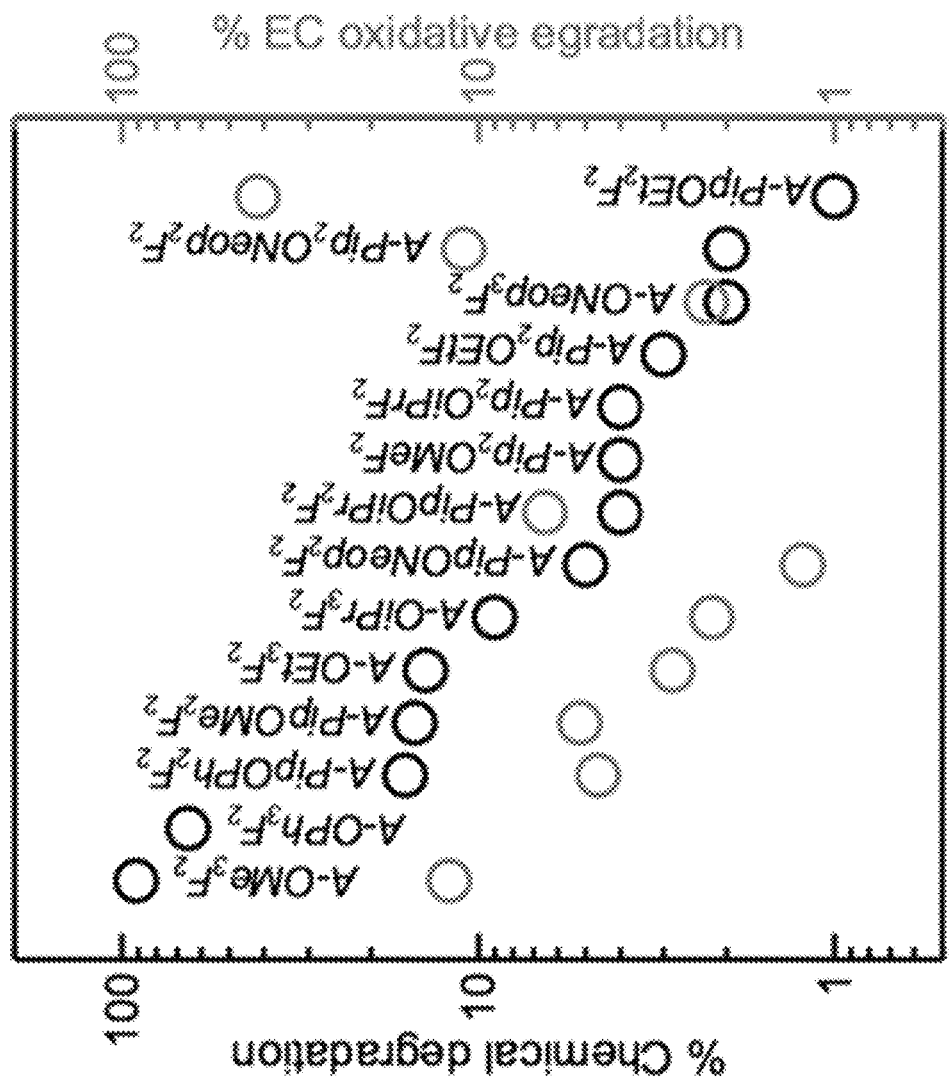
FIG. 7 shows chemical and electrochemical oxidative stability test results for FAST salts. The black circles indicate the degradation percentages of the sulfonimide salts after incubation with 10 equiv. Li$_2$O$_2$ and KO$_2$ in DMF for three days at 80° C.

Next, the chemical stability of various FAST salts was investigated under solution conditions designed to mimic the oxygen electrode of a typical aprotic Li-air battery. See S. Feng, M. Chen, L. Giordano, M. Huang, W. Zhang, C. V. Amanchukwu, R. Anandakathir, Y. Shao-Horn and J. A. Johnson, *J. Mater. Chem. A*, 2017, 5, 23987-23998, J. R. Harding, C. V. Amanchukwu, P. T. Hammond and Y Shao-Horn, *J. Phys. Chem. C*, 2015, 119, 6947-6955, and C. V. Amanchukwu, J. R. Harding, Y Shao-Horn and P. T. Hammond, *Chem. Mater.*, 2015, 27, 550-561, each of which is incorporated by reference in its entirety. In FIG. 7, Percent degradation was quantified by $^1$H NMR using 4-methoxybiphenyl as a reference standard. The electrochemical oxidation percentages of the corresponding FAST salts in the potentiostatic tests at the end of the 4.2-V step are shown by the blue circles.

Figure 11:
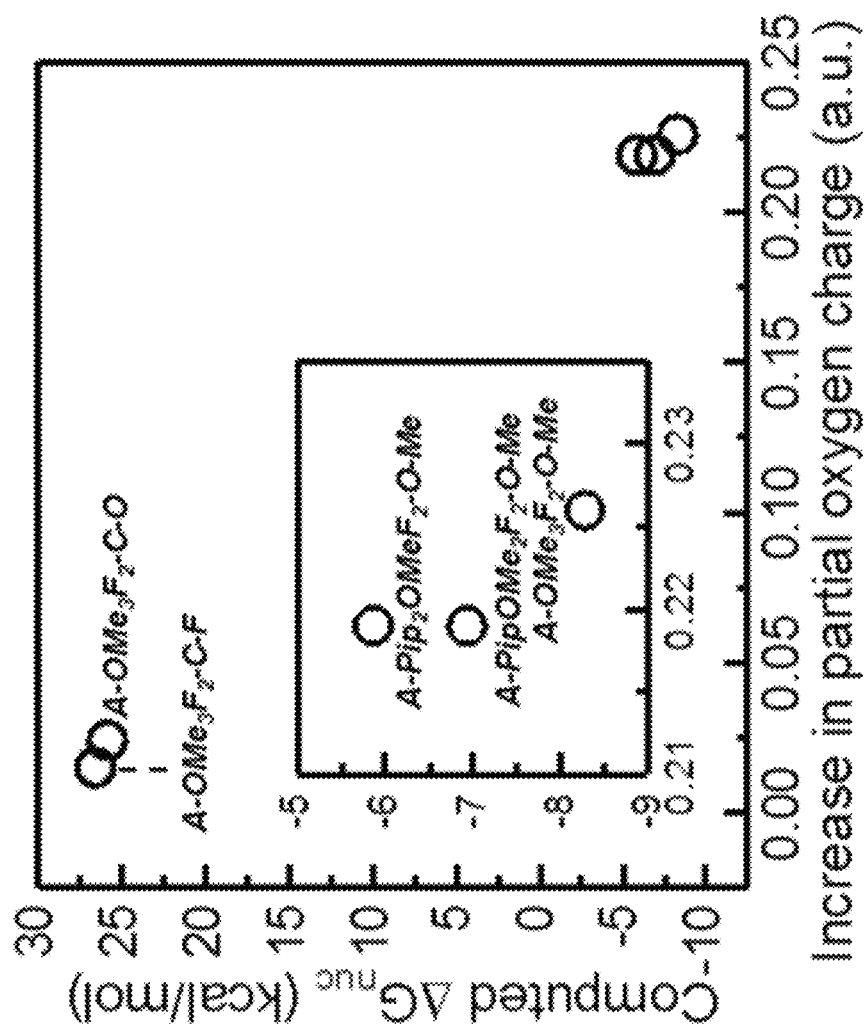
FIG. 11 shows the computed Gibbs free energy for nucleophilic substitution by superoxide, $\Delta G_{nuc}$, at select carbon sites in A-OMe$_3$F$_2$, A-PipOMe$_2$F$_2$, and A-Pip$_2$OMeF$_2$ plotted against the increase in NPA partial charge of the attacking oxygen in superoxide (partial charge of oxygen after the substitution reaction minus its charge before the reaction).

Each FAST salt was dissolved in DMF (20 mg/mL) and mixed with 10 equivalent Li$_2$O$_2$, KO$_2$, and 1 equivalent 4-methoxybiphenyl as internal standard (for quantitative NMR analysis); the mixture was stirred at 80° C. for 3 days. The supernatant of the mixture was characterized by $^1$H, $^{19}$F-NMR, and liquid chromatography-mass spectrometry (LC-MS). Generally, FAST salts with a greater number of aryl fluoride groups displayed lower chemical stability: for salts derived from A and C, only those with two meta fluorine atoms have negligible degradation, whereas in salts derived from B no aryl fluorides were tolerated due to the strong electron withdrawing effect of —CF$_3$ group ($\sigma_{para}$=0.54). For tri-substituted salts derived from A (FIGS. 1 and 2), the chemical stability was strongly affected by the identity and pattern of the substituents. FIG. 5 provides a comparison of the percentage of degradation (obtained by quantitative $^1$H NMR) of each salt. For salts derived from A, it was observed that bulkier —OR substituents improved the stability against chemical degradation. A-OMe$_3$F$_2$ was observed to degrade almost completely (91%) while no degradation was detected for A-ONeop$_3$F$_2$. FAST salts with Pip groups exhibited greater chemical stability than those with —OR substitutions: the degraded percentage decreased from 65% in A-OPh$_3$F$_2$ and 91% in A-OMe$_3$F$_2$ to 16% in A-PipOPh$_2$F$_2$ and 15% in A-PipOMe$_2$F$_2$. When two Pip groups were introduced (A-Pip$_2$ORF$_2$), less than 4% degradation was observed regardless of the identity of R. These experimental results for chemical stability are inversely correlated with the calculated average carbon atomic charges on the aromatic ring: A-Pip$_2$ORF$_2$>A-PipOR$_2$F$_2$>A-OR$_3$F$_2$, which supports the expectation that more electron rich FAST salts should be less susceptible to nucleophilic attack. Furthermore, the Gibbs free energy was computed for nucleophilic substitution by superoxide, $\Delta G_{nuc}$, at select carbon sites (i.e., O—CH$_3$) in A-OMe$_3$F$_2$, A-PipOMe$_2$F$_2$, and A-Pip$_2$OMeF$_2$ (FIG. 11); the computed trend of $\Delta G_{nuc}$ (A-OMe$_3$F$_2$<A-PipOMe$_2$F$_2$<A-Pip$_2$OMeF$_2$) follows the trend in the chemical stability of these salts determined experimentally. Finally, the computed $\Delta G_{nuc}$ was plotted against the increase in the NPA partial charge of the attacking oxygen in superoxide (partial charge of the oxygen after the substitution reaction minus its partial charge before the reaction; FIG. 11). It is observed that a larger increase in the oxygen partial charge corresponds to a more favourable $\Delta G_{nuc}$ in these salts; this correlation was also observed in the recent study on the nucleophilic substitution of small organic molecules such as carbonates and ethers by superoxide. See S. Feng, M. Chen, L. Giordano, M. Huang, W. Zhang, C. V. Amanchukwu, R. Anandakathir, Y. Shao-Horn and J. A. Johnson, *J. Mater. Chem. A*, 2017, 5, 23987-23998, which is incorporated by reference in its entirety. This trend suggests that a larger increase in the attacking oxygen partial charge indicates stronger electron-donating strength of superoxide at the carbon site, which gives rise to more favourable $\Delta G_{nuc}$.

Figure 8B:
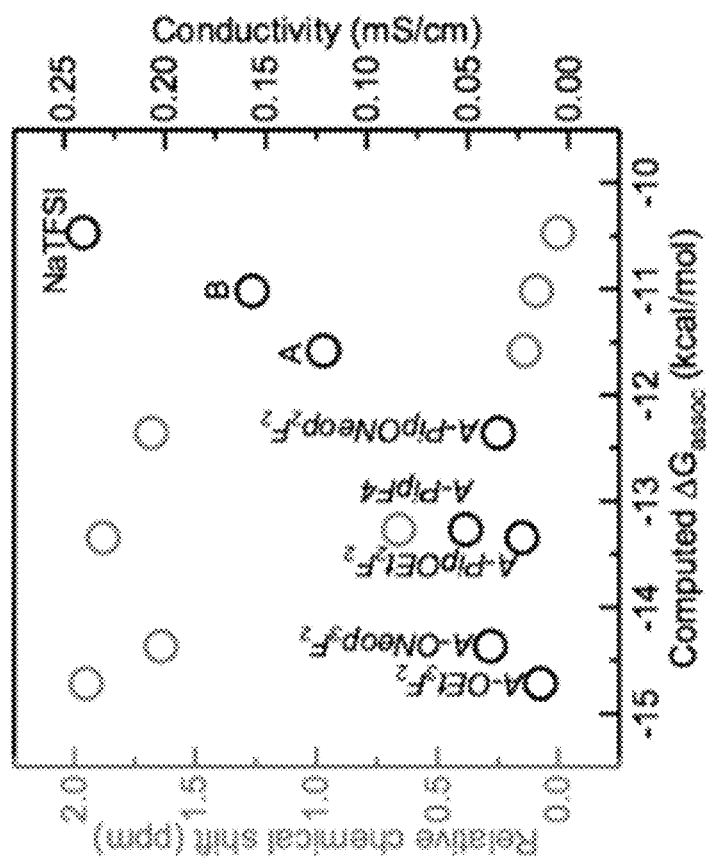
FIG. 8B shows the $^{23}$Na NMR chemical shift (relative to NaTFSI) and ion conductivity of 0.1 M 1,2-dimethoxyethane solution at 25° C. versus the computed anion-Na$^+$ association free energy, $\Delta G_{assoc}$, in implicit diethylether solvent with dielectric constant set at 7.2 for representative FAST salts.
Figure 8A:
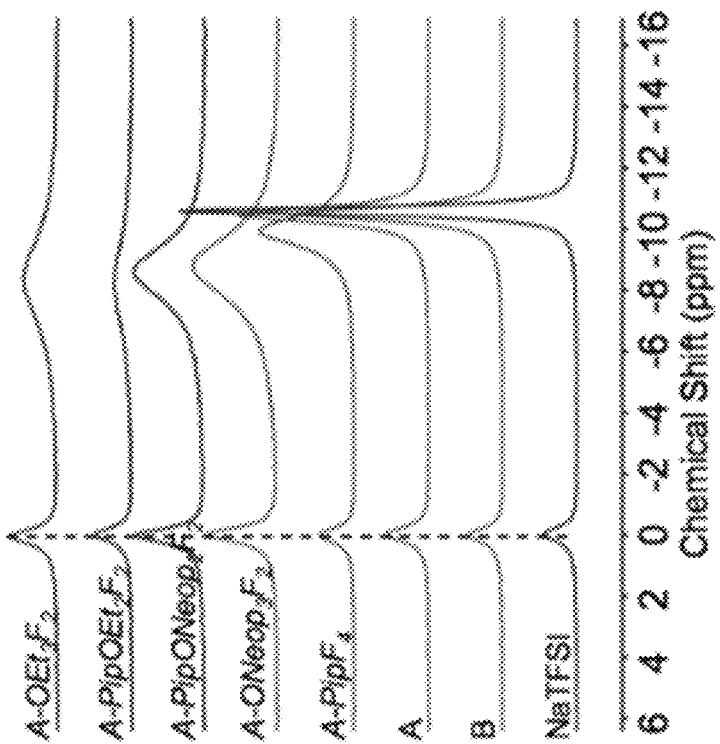
FIG. 8A shows the measured chemical shift of $^{23}$Na NMR signal for representative FAST salts (the $^{23}$Na signal from the inner standard, NaClO$_4$, is set to 0 ppm).

The ion conductivity in liquid electrolyte depends upon two factors: charge carrier concentration and mobility. With the same concentration of salts, the extent to which the salt is dissociated determines the charge carrier concentration. Generally, salt anions with higher Lewis basicity interact more strongly with alkali metal cations, and thus increase the extent of anion-cation association. See S. S. Sekhon, N. Arora and H. P. Singh, *Solid State Ion.*, 2003, 160, 301-307, C. M. Burke, V. Pande, A. Khetan, V. Viswanathan and B. D. McCloskey, *Proc. Natl. Acad. Sci. U.S.A.*, 2015, 112, 9293-9298, and M. Schmeisser, P. Illner, R. Puchta, A. Zahl and R. van Eldik, *Chemistry*, 2012, 18, 10969-10982, each of which is incorporated by reference in its entirety. The TFSI anion is well known for being an "innocent" anion with weak interactions with metal ions. See M. Schmeisser, P. Illner, R. Puchta, A. Zahl and R. van Eldik, *Chemistry*, 2012, 18, 10969-10982, which is incorporated by reference in its entirety. To compare the FAST salts with TFSI and evaluate the extent of ion dissociation, the anion-cation interaction strengths for the FAST salts were determined by $^{23}$Na NMR. See M. Schmeisser, P. Illner, R. Puchta, A. Zahl and R. van Eldik, *Chemistry*, 2012, 18, 10969-10982, and R. H. Erlich and A. I. Popov, *J. Am. Chem. Soc.*, 1971, 93, 5620-5623, each of which is incorporated by reference in its entirety. The sodium salts were prepared as 0.1 M solutions in nitromethane with 0.25 M NaClO$_4$ in DMSO as the internal standard. The $^{23}$Na chemical shifts of FAST salts relative to NaTFSI are shown in FIG. 8A. It is immediately obvious that the nature of the anion plays an important role in the resulting chemical shift. For example, A-OR$_3$F$_2$ and A-PipOR$_2$F$_2$ have $^{23}$Na signals shift toward down field, indicating stronger anion-Na$^+$ interaction than the parent type A and B salts. A considerable amount of line broadening was also observed and can be attributed to the formation of more ion pairs. See R. H. Erlich and A. I. Popov, *J. Am.*

Figures 12A, 12B:
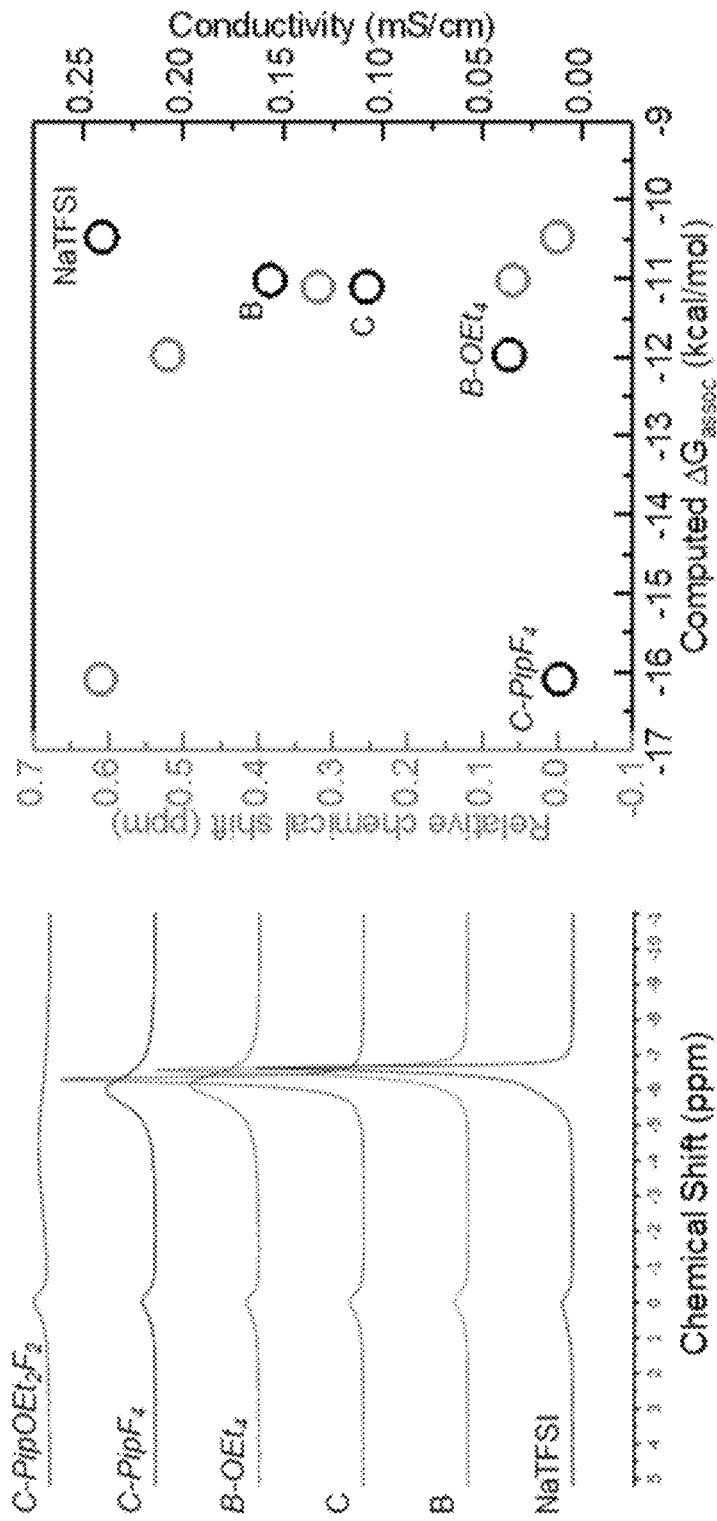
FIG. 12A shows $^{23}$Na chemical shifts of representative B type and C type FAST salts (the $^{23}$Na signal from the inner standard, NaClO$_4$, is set to 0 ppm).
FIG. 12B shows the $^{23}$Na NMR chemical shift (relative to NaTFSI) and ionic conductivities of 0.1 M 1,2-dimethoxyethane solution at 25° C. versus the computed free energy of anion-Na$^+$ association, $\Delta G_{asso}$, for representative B type and C type FAST salts in implicit diethylether solvent with dielectric constant set at 7.2.

*Chem. Soc.*, 1971, 93, 5620-5623, which is incorporated by reference in its entirety. As the FAST salt anions become more electron rich (i.e., as the number of F atoms decreases), they seem to become more Lewis basic, display stronger interactions with $Na^+$ and produce more ion pairs. To validate this hypothesis and study the effect of different substitution groups on anion-$Na^+$ interaction and ion conductivity, the calculated Gibbs free energy of ion pair association, $\Delta G_{assoc}$, versus the relative $^{23}Na$ chemical shifts as well as the ion conductivities of 1,2-dimethoxyethane (DME) solutions containing several FAST salts at 0.1 M experimentally obtained at 25° C. was plotted (FIG. 8B). Implicit diethylether solvent with dielectric constant set at 7.2 was used to mimic the solvent used for conductivity studies (DME). As expected, salts with more negative calculated $\Delta G_{assoc}$ values (more favorable anion-$Na^+$ association) have more down-field shift in $^{23}Na$ NMR spectrum and displayed lower conductivity. More specifically, it was observed that solutions containing type A and B salts have ion conductivities that are a factor of 2 and 1.5, respectively, lower than that of NaTFSI while A-ONeop$_3$F$_2$, A-PipF$_4$ and A-PipONeop$_2$F$_2$ exhibit conductivities that are 4 to 7 times lower. The conductivities of solutions containing these salts are inversely related to the salt anion Lewis basicity and anion-cation interaction strength. Furthermore, $^{23}Na$ NMR chemical shift of other B type and C type salts were also measured shown in FIG. 12A. Here acetonitrile was chosen as solvent due to low solubility of B and C type salts in nitromethane. Acetonitrile solvates $Na^+$ better than nitromethane and thus decreases the anion-$Na^+$ interaction strength difference. See R. H. Erlich and A. I. Popov, *J. Am. Chem. Soc.*, 1971, 93, 5620-5623, which is incorporated by reference in its entirety. Nevertheless, it was observed that salts with more $S_NAr$ substitutions have $^{23}Na$ signal shift toward down field and line broadening comparing with B and C parent salts (FIG. 12A); these salts also exhibit more favorable $\Delta G_{assoc}$ for anion-$Na^+$ association and lower ion conductivity in DME solution (FIG. 12B). Overall, salts with more $S_NAr$ substitutions among all three types have greater Lewis basicity, which leads to stronger interaction with $Na^+$ and more negative $\Delta G_{assoc}$ values. These results highlight the balance of factors that must be considered in the design of functional TFSI derivatives.

Figure 9B:
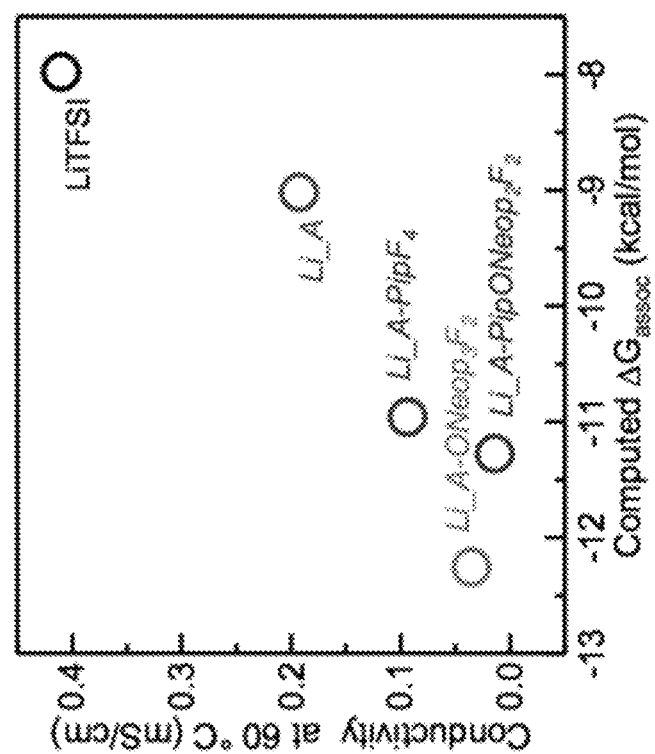
FIG. 9B shows the conductivity of FAST-PEO electrolytes at 60° C. versus computed free energy of anion-Li$^+$ association, $\Delta G_{assoc}$, in implicit diethylether solvent with dielectric constant set at 7.2.
Figure 9A:
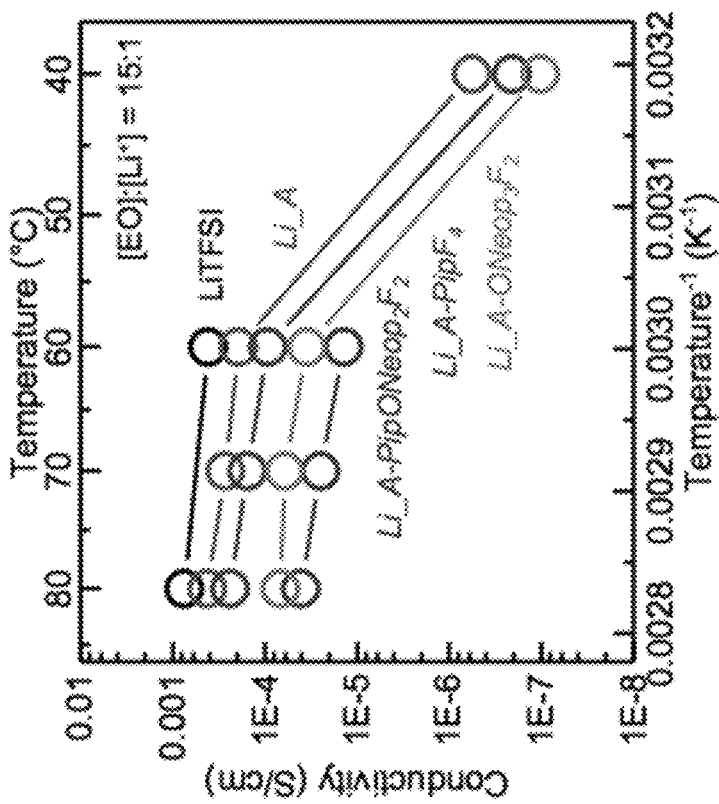
FIG. 9A shows the ion conductivities of solid state FAST-PEO electrolytes prepared via blending representative LiFAST salts and PEO (molar ration of PEO repeat units and lithium ion [EO]:[Li$^+$]=15:1) at various temperatures.
Figure 13:
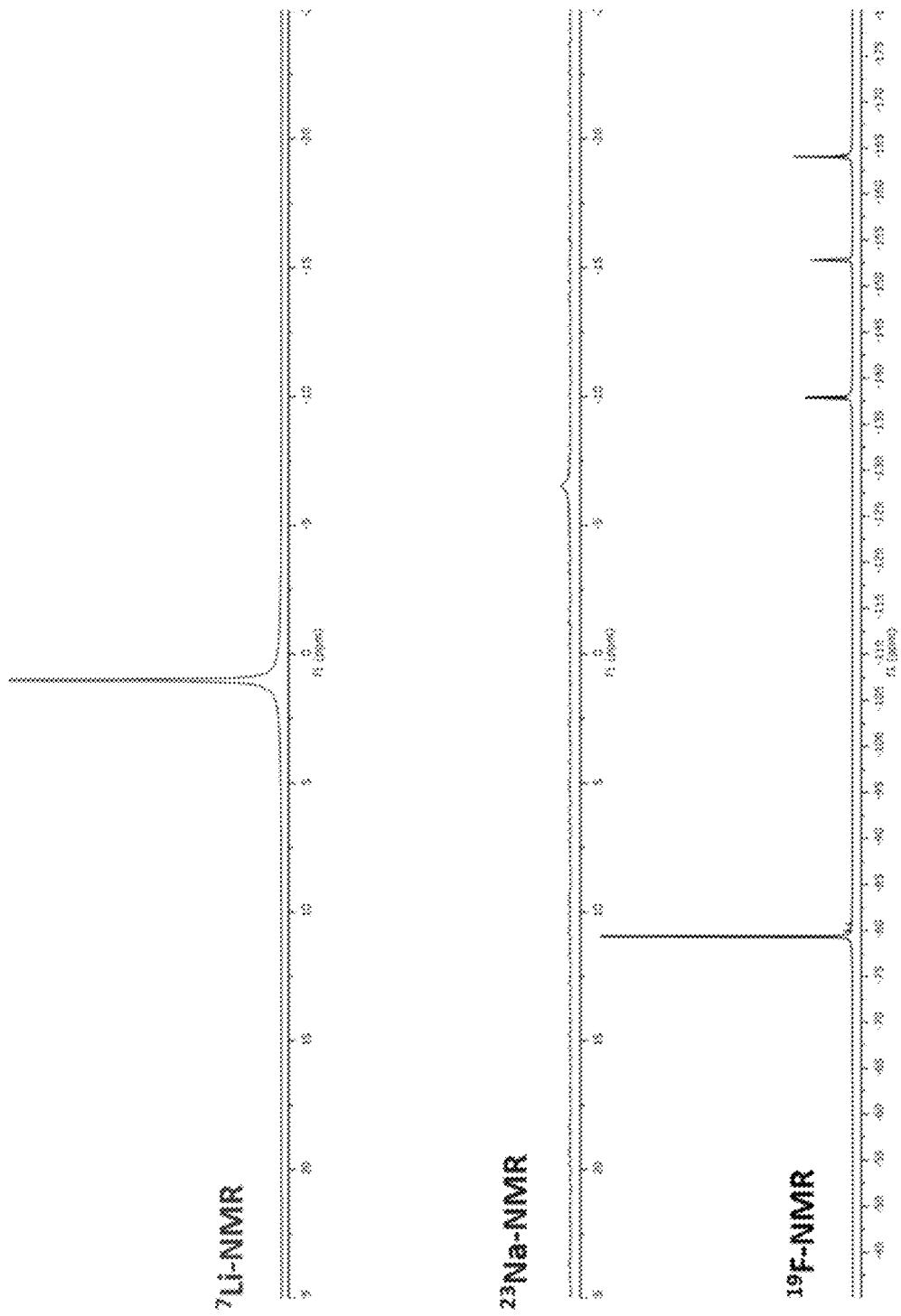
FIG. 13 shows NMR spectrum of A after ion exchange with lithium chloride. The very strong $^7$Li peak and rather weak $^{23}$Na peak indicate nearly complete replacement of Na$^+$ by Li$^+$.
Figure 14:
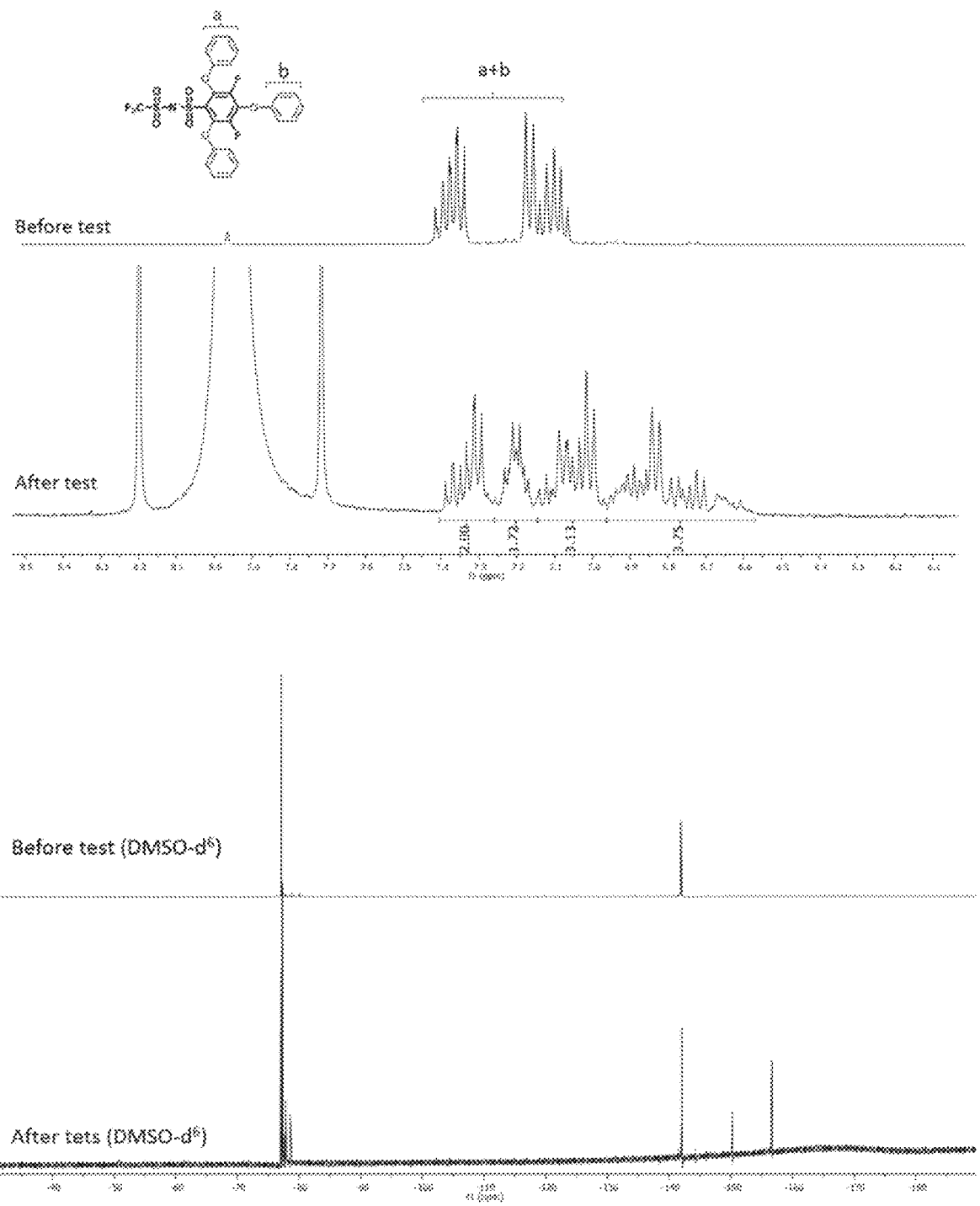
FIG. 14 shows $^1$H and $^{19}$F NMR of A-OPh$_3$F$_2$ before and after stability test in DMF. NMR solvent: d$^6$-DMSO.
Figure 15:
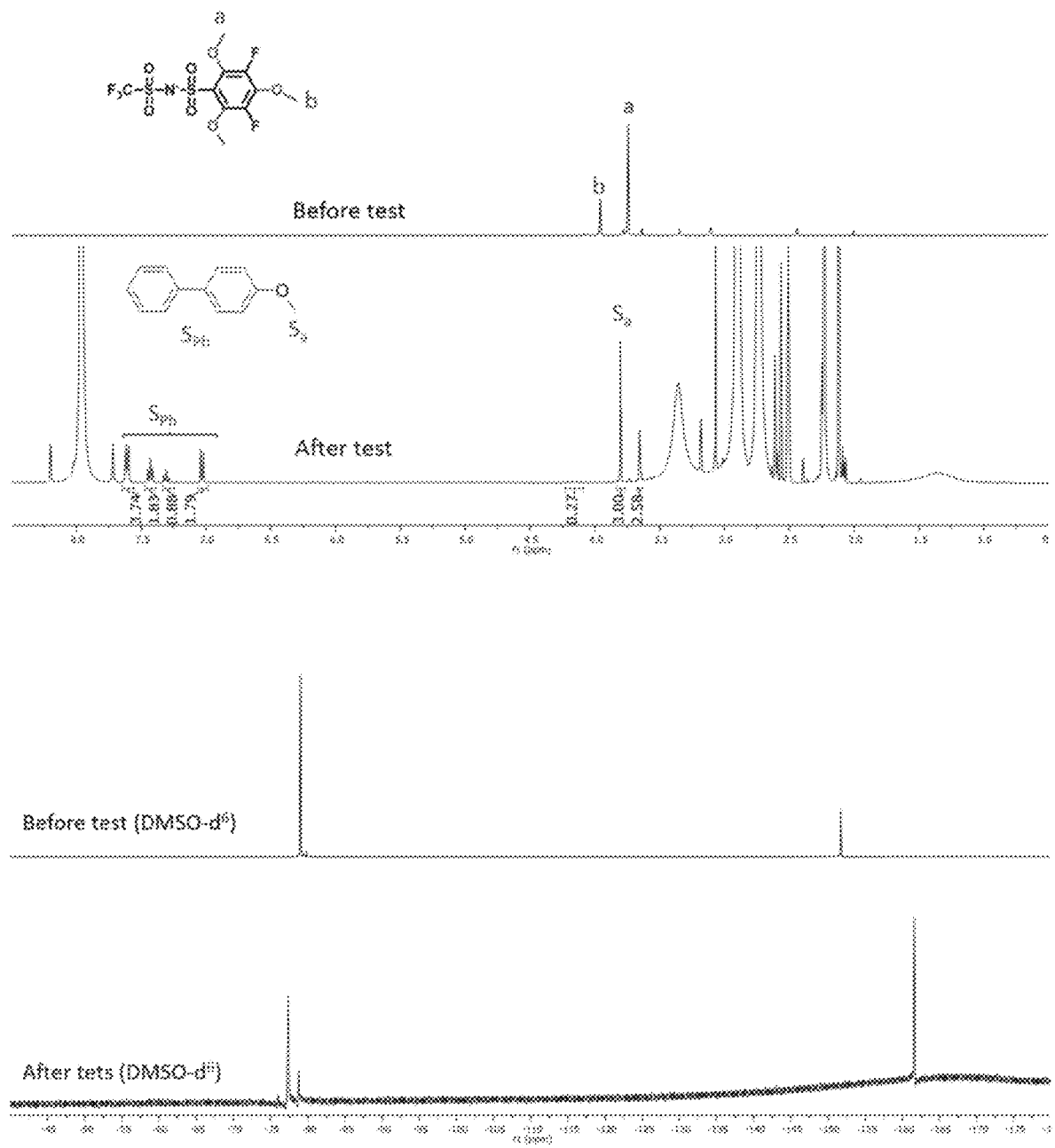
FIG. 15 shows $^1$H and $^{19}$F NMR of A-OMe$_3$F$_2$ before and after stability test in DMF. NMR solvent: d$^6$-DMSO.
Figure 16:
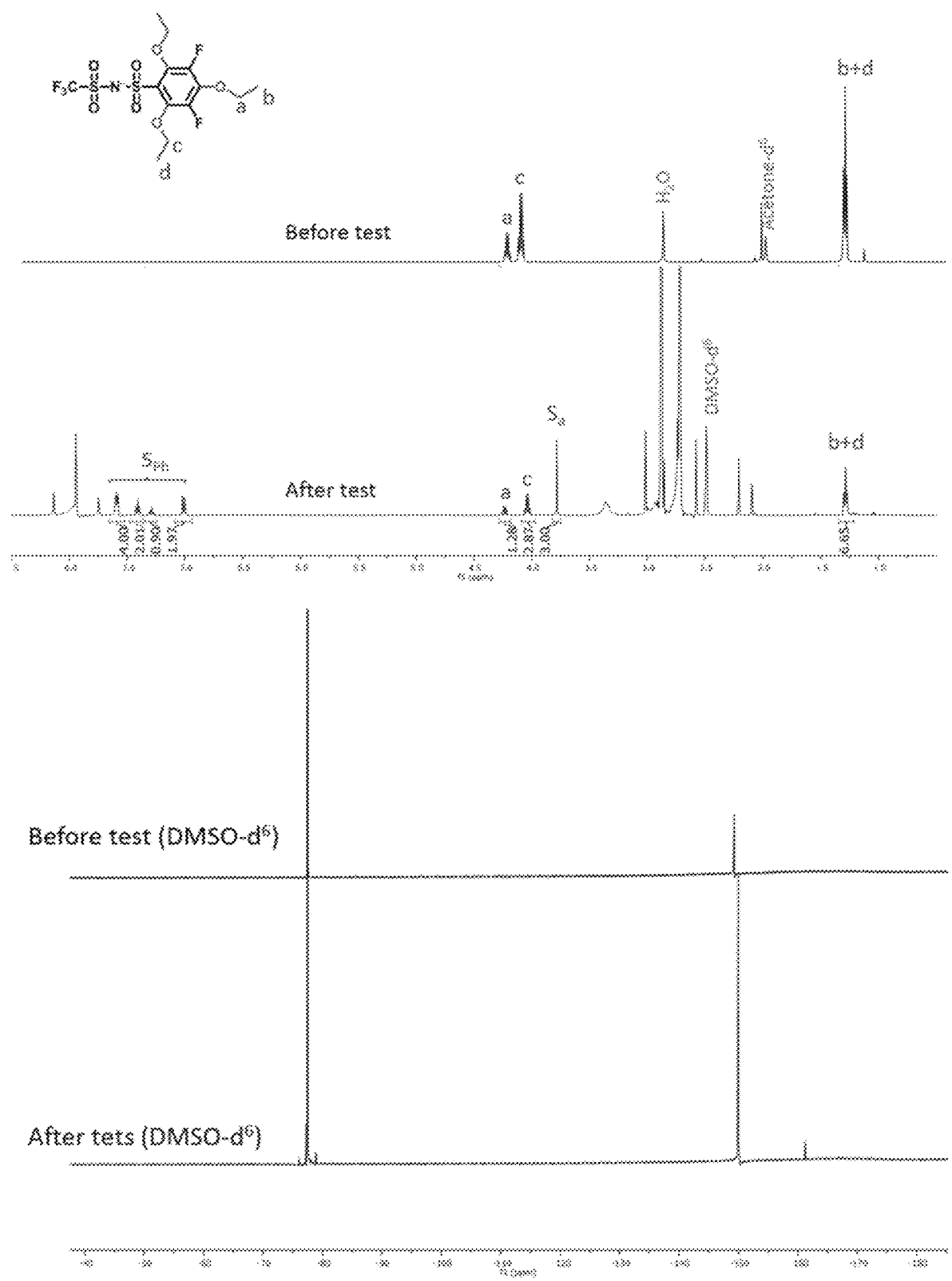
FIG. 16 shows $^1$H and $^{19}$F NMR of A-OEt$_3$F$_2$ before and after stability test in DMF. NMR solvent: d$^6$-DMSO.
Figure 17:
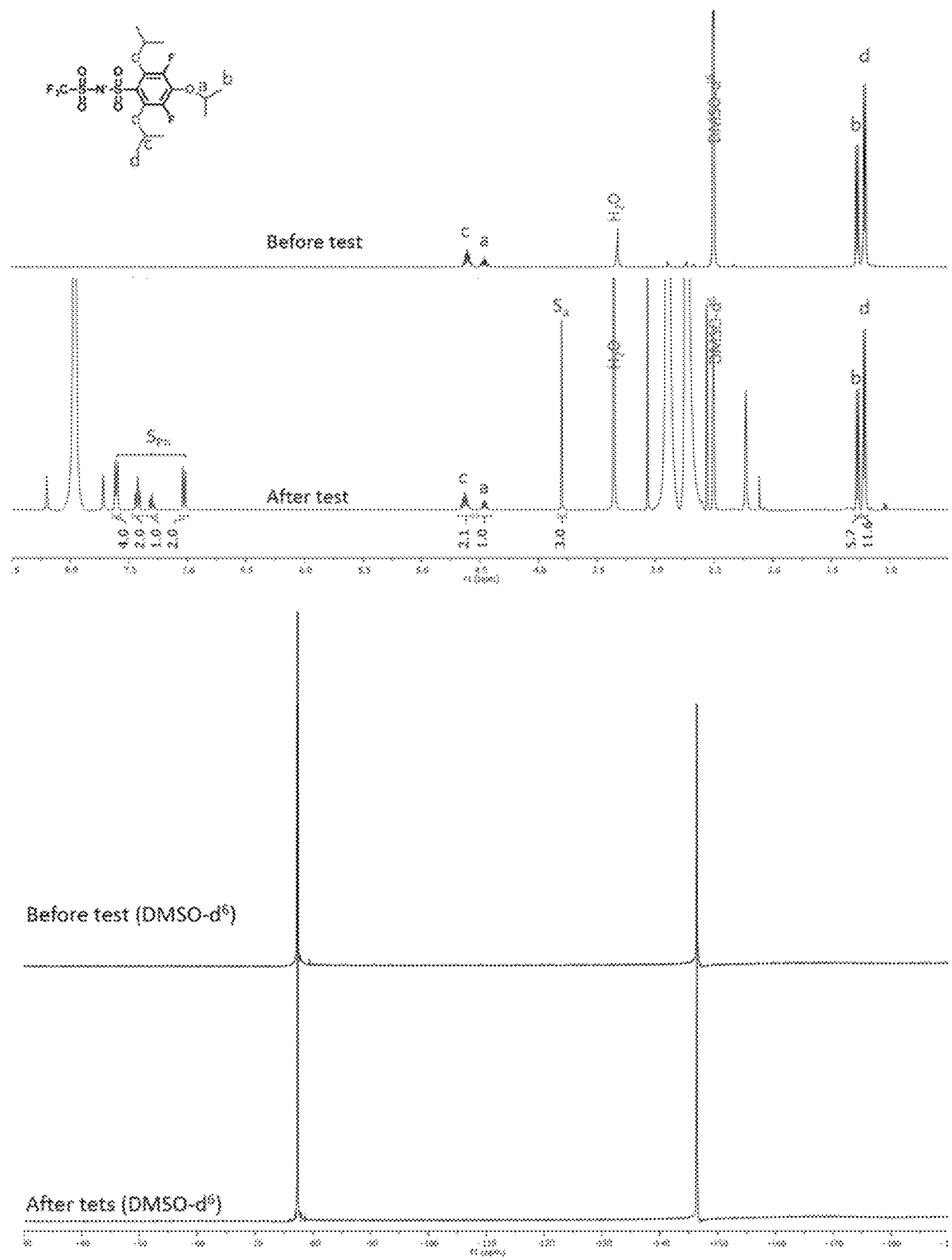
FIG. 17 shows $^1$H and $^{19}$F NMR of A-OiPr$_3$F$_2$ before and after stability test in DMF. NMR solvent: d$^6$-DMSO.
Figure 18:
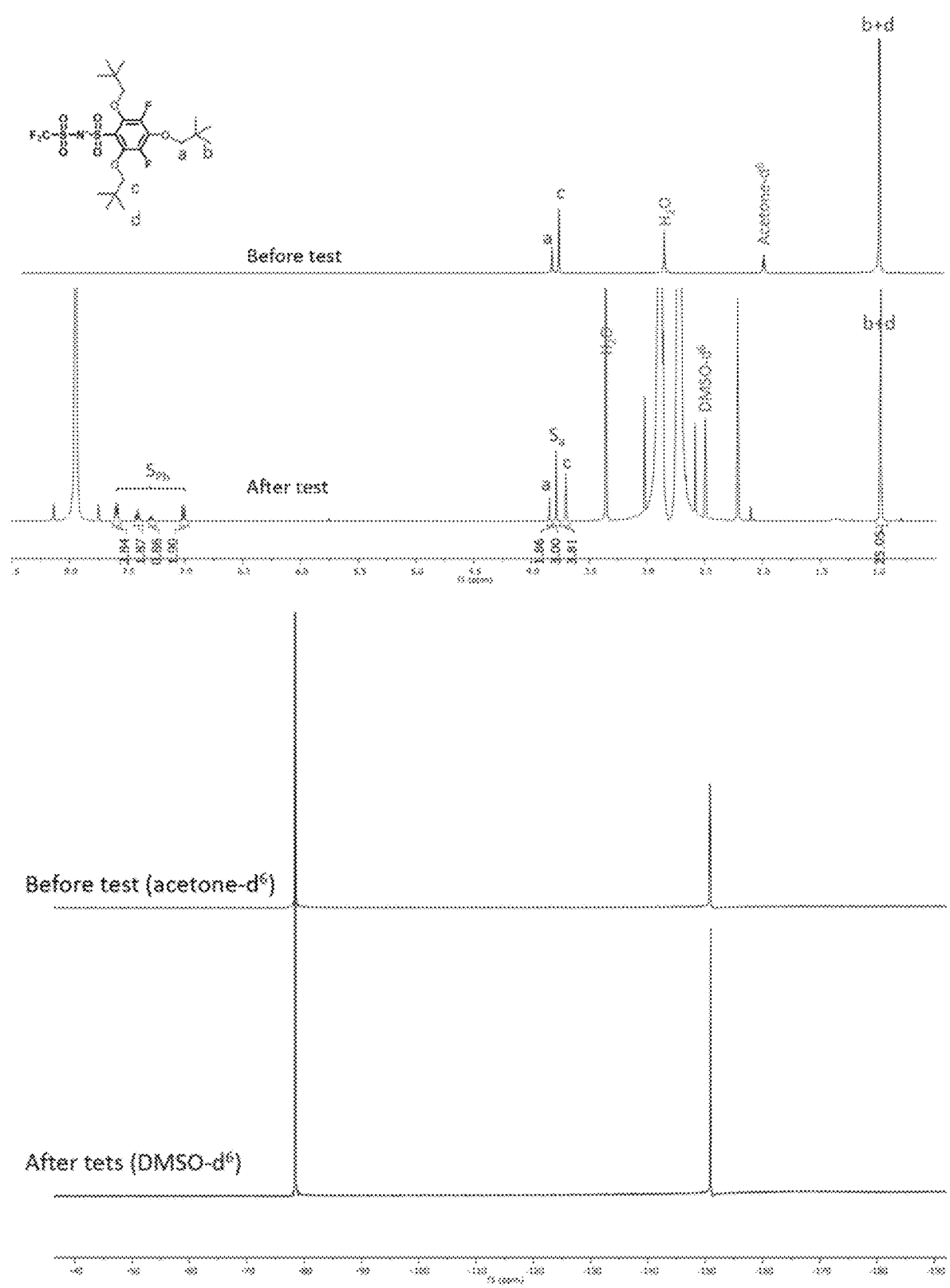
FIG. 18 shows $^1$H and $^{19}$F NMR of A-ONeop$_3$F$_2$ before and after stability test in DMF. NMR solvent: d$^6$-DMSO.
Figure 19:
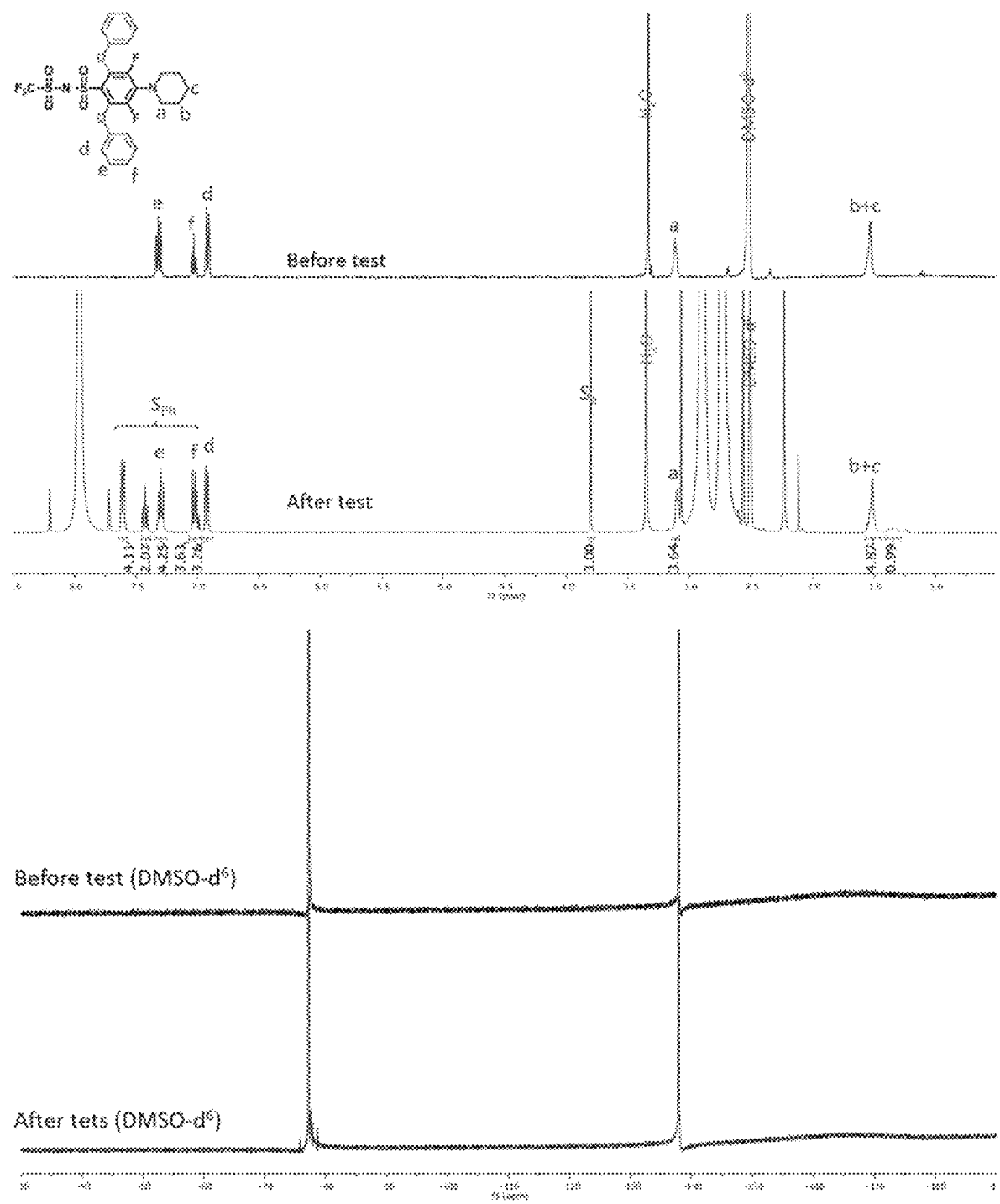
FIG. 19 shows $^1$H and $^{19}$F NMR of A-PipOPh$_2$F$_2$ before and after stability test in DMF. NMR solvent: d$^6$-DMSO.
Figure 20:
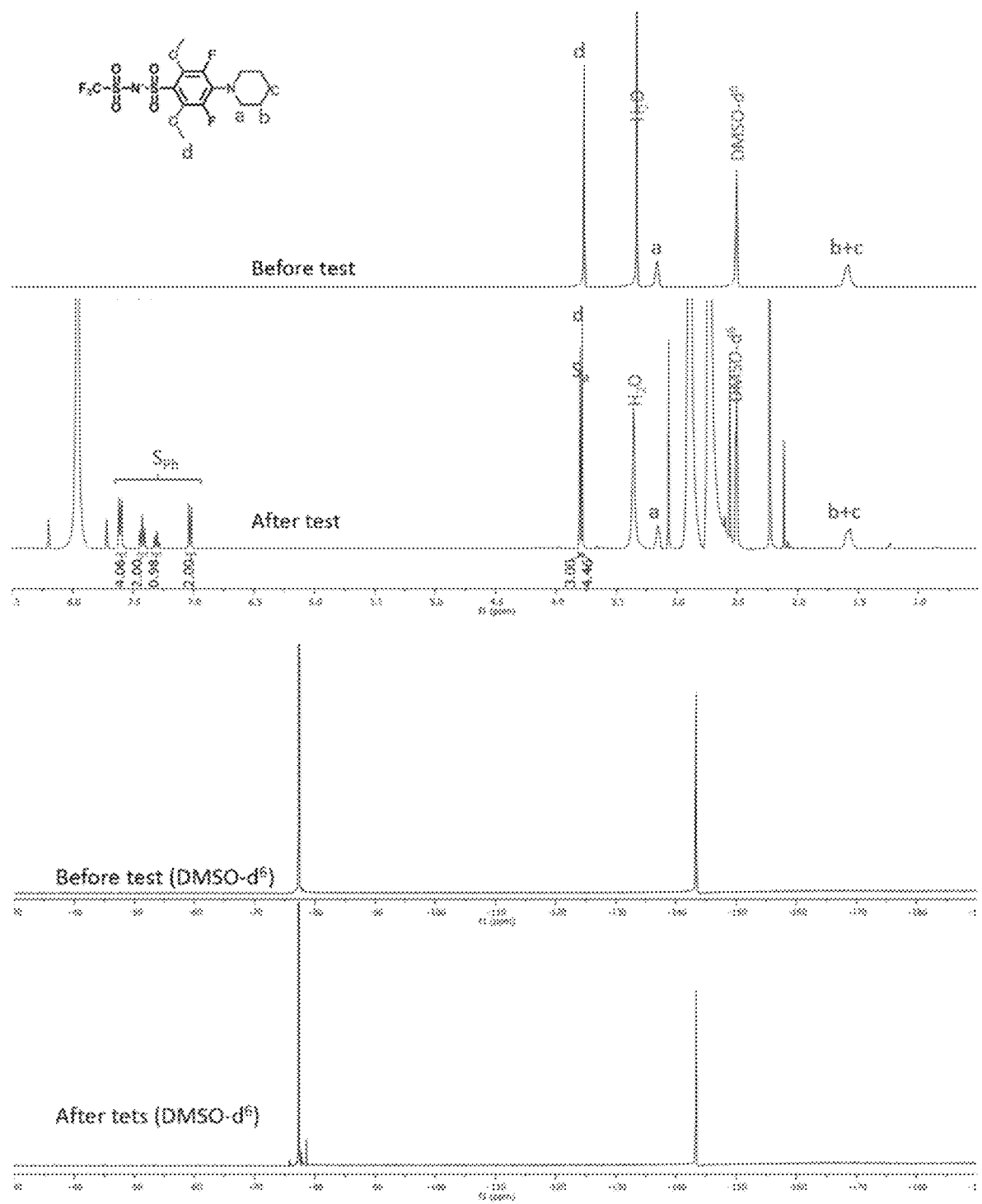
FIG. 20 shows $^1$H and $^{19}$F NMR of A-PipOMe$_2$F$_2$ before and after stability test in DMF. NMR solvent: d$^6$-DMSO.
Figure 21:
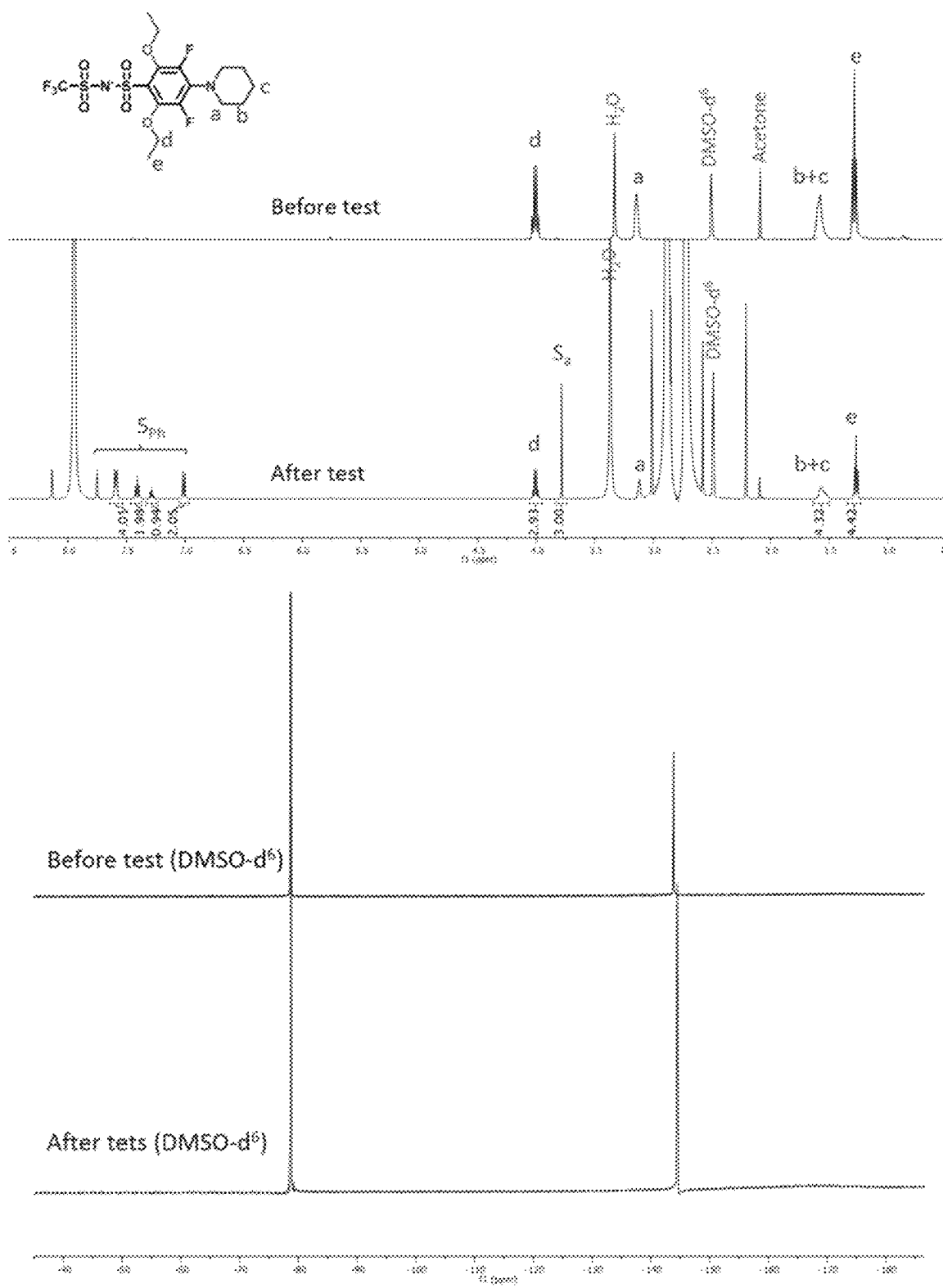
FIG. 21 shows $^1$H and $^{19}$F NMR of A-PipOEt$_2$F$_2$ before and after stability test in DMF. NMR solvent: d$^6$-DMSO.
Figure 22:
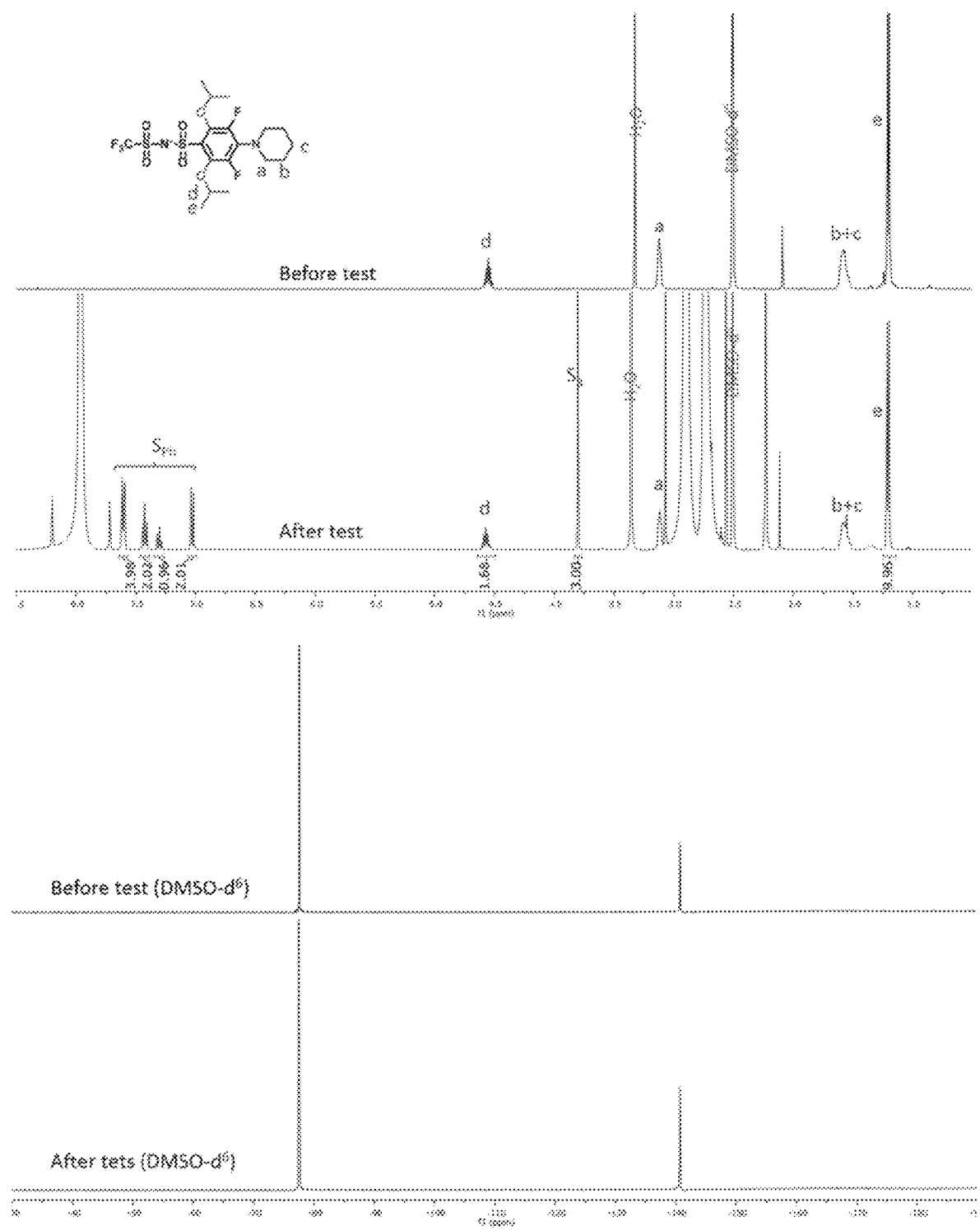
FIG. 22 shows $^1$H and $^{19}$F NMR of A-PipOiPr$_2$F$_2$ before and after stability test in DMF. NMR solvent: d$^6$-DMSO.
Figure 23:
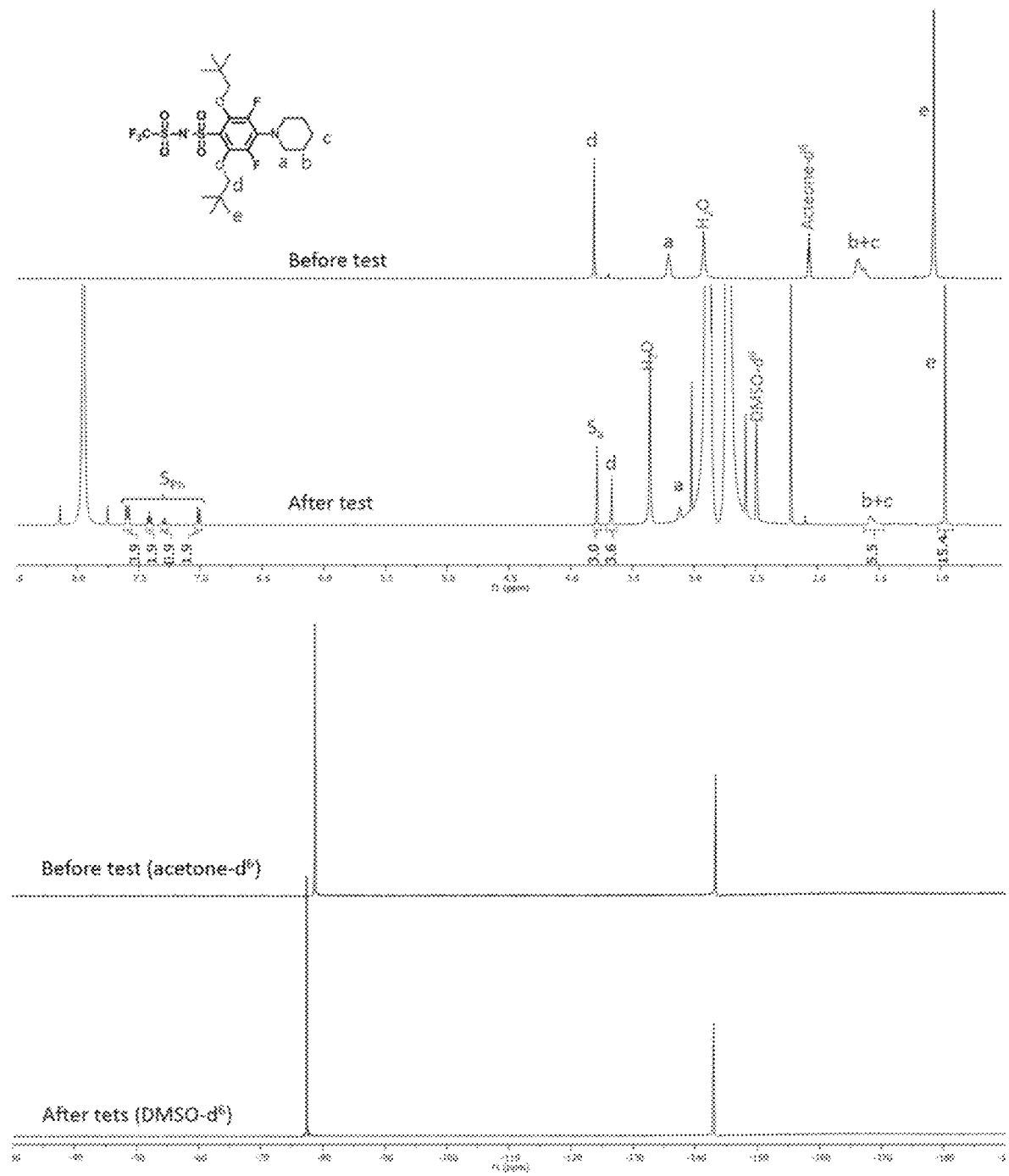
FIG. 23 shows $^1$H and $^{19}$F NMR of A-PipONeop$_2$F$_2$ before and after stability test in DMF. NMR solvent: d$^6$-DMSO.
Figure 24:
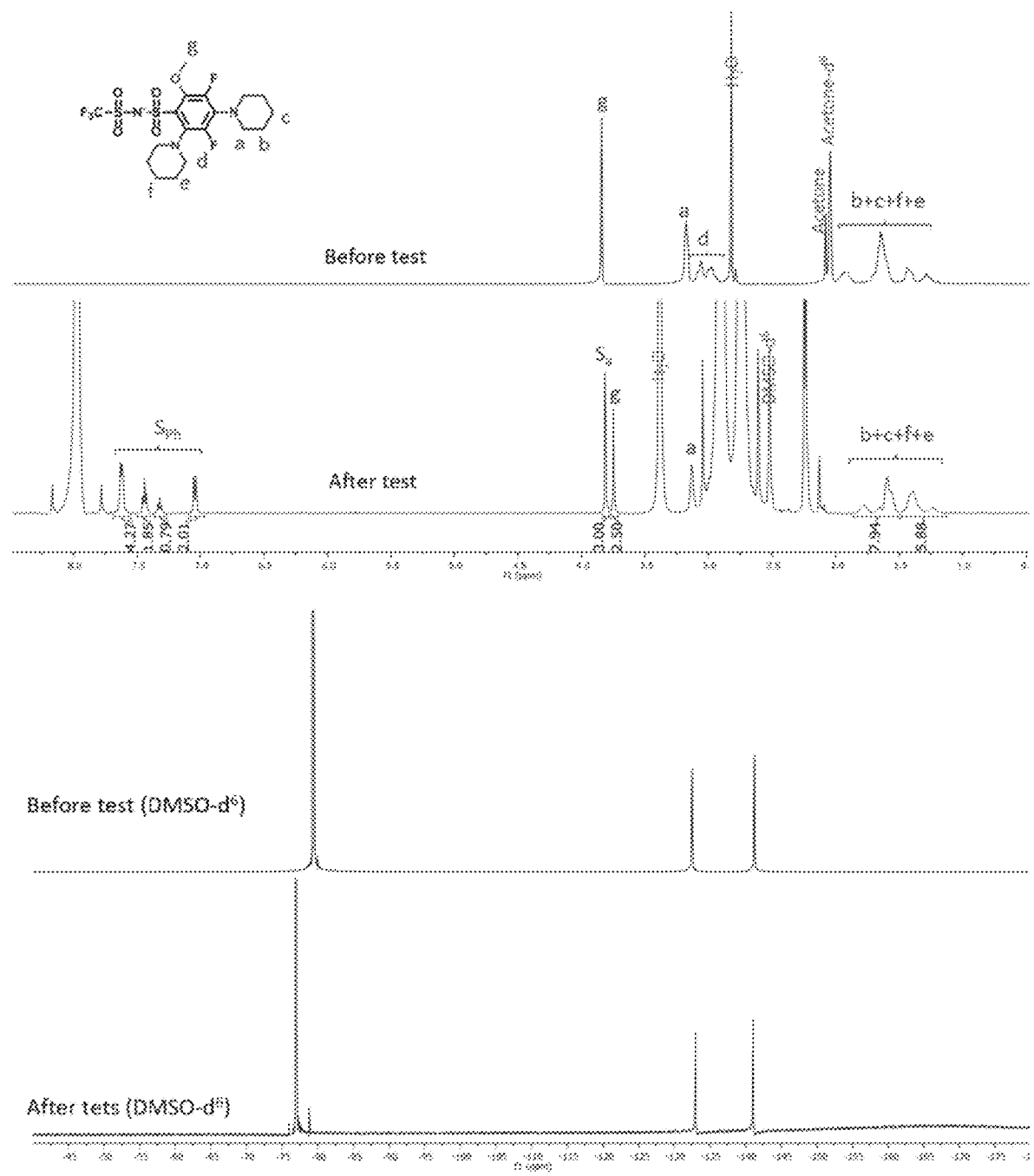
FIG. 24 shows $^1$H and $^{19}$F NMR of A-Pip$_2$OMeF$_2$ before and after stability test in DMF. NMR solvent: d$^6$-DMSO.
Figure 25:
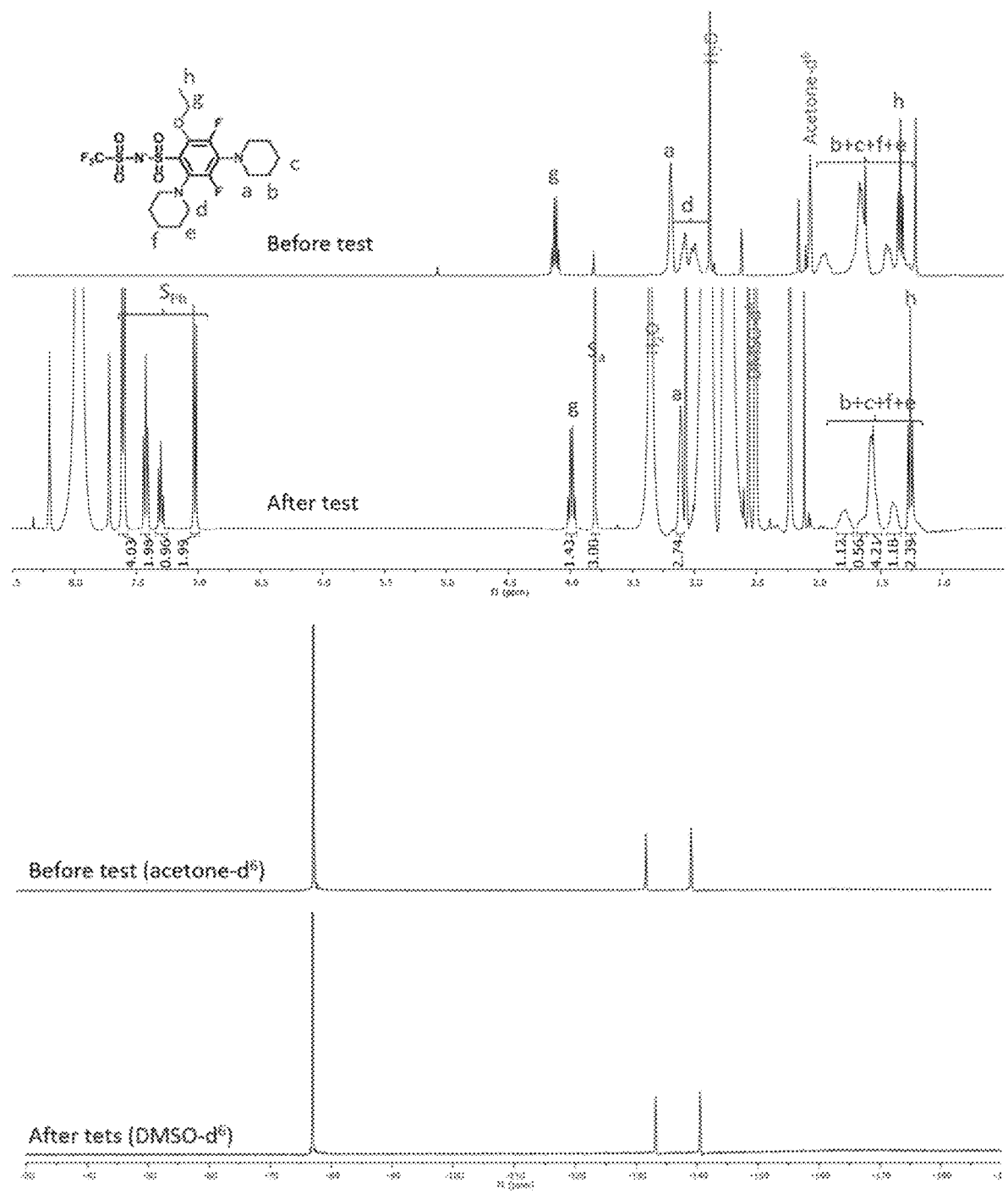
FIG. 25 shows $^1$H and $^{19}$F NMR of A-Pip$_2$OEtF$_2$ before and after stability test in DMF. NMR solvent: d$^6$-DMSO.
Figure 26:
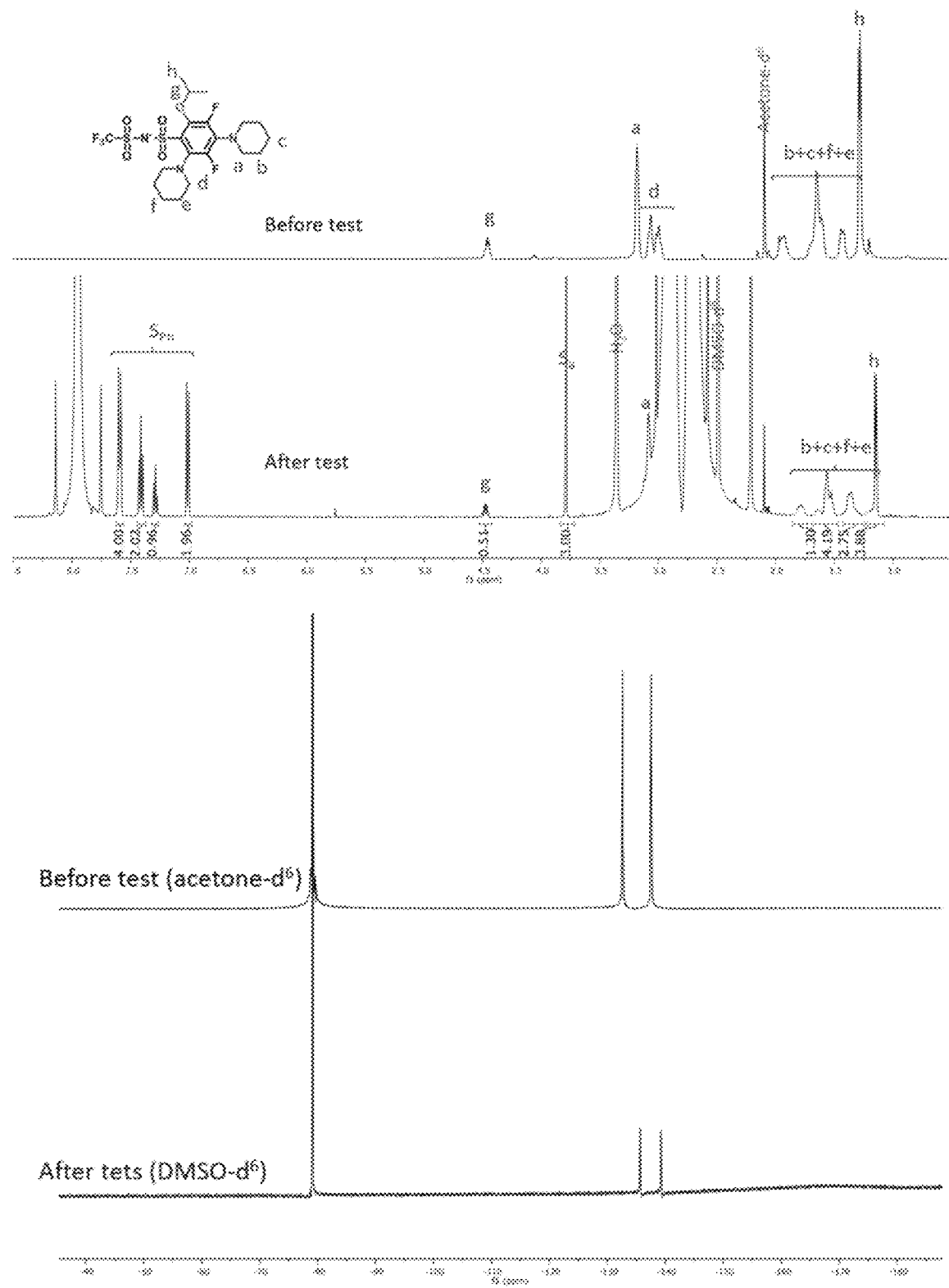
FIG. 26 shows $^1$H and $^{19}$F NMR of A-Pip$_2$OiPrF$_2$ before and after stability test in DMF. NMR solvent: d$^6$-DMSO.
Figure 27:
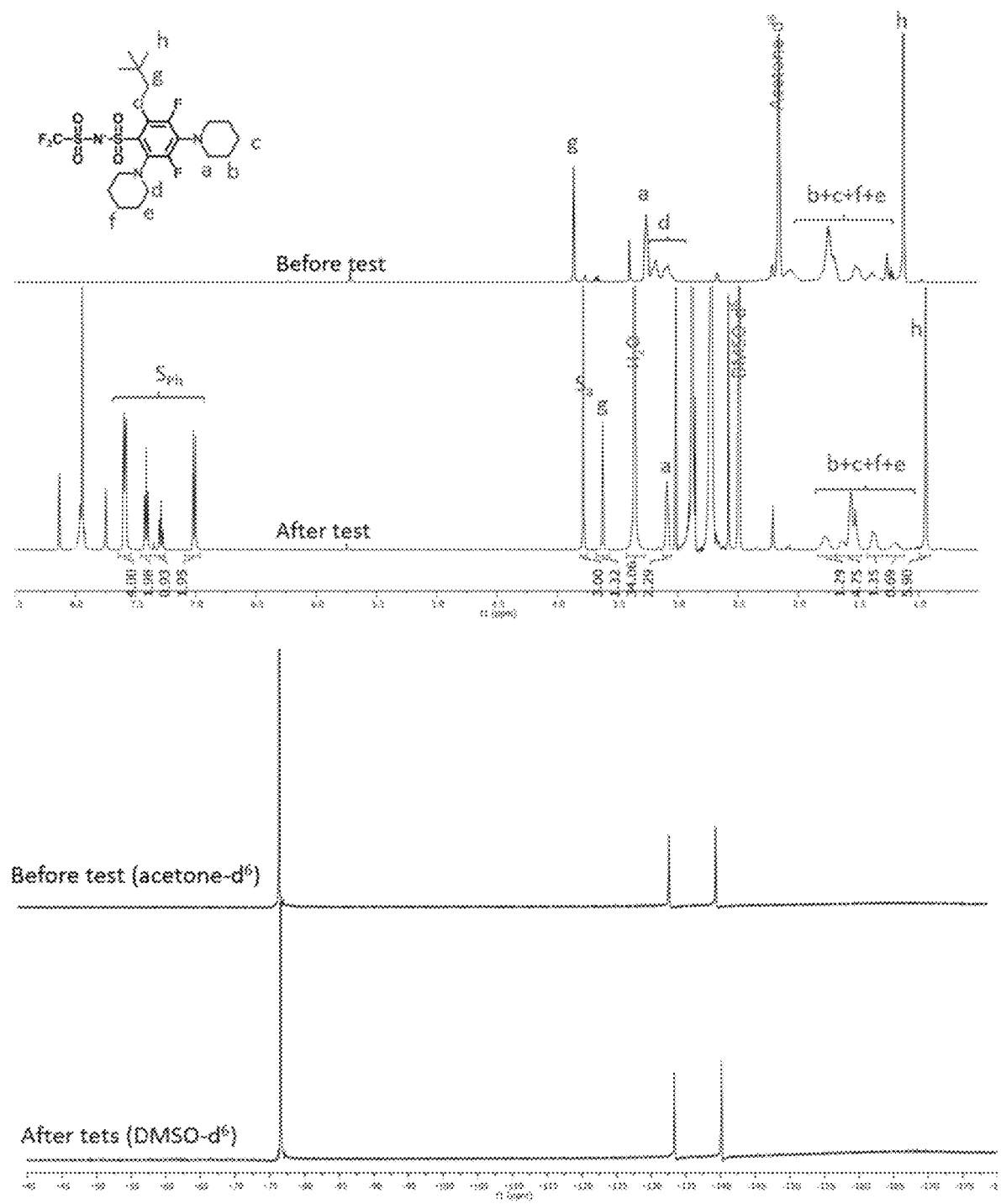
FIG. 27 shows $^1$H and $^{19}$F NMR of A-Pip$_2$ONeopF$_2$ before and after stability test in DMF. NMR solvent: d$^6$-DMSO.
Figure 28:
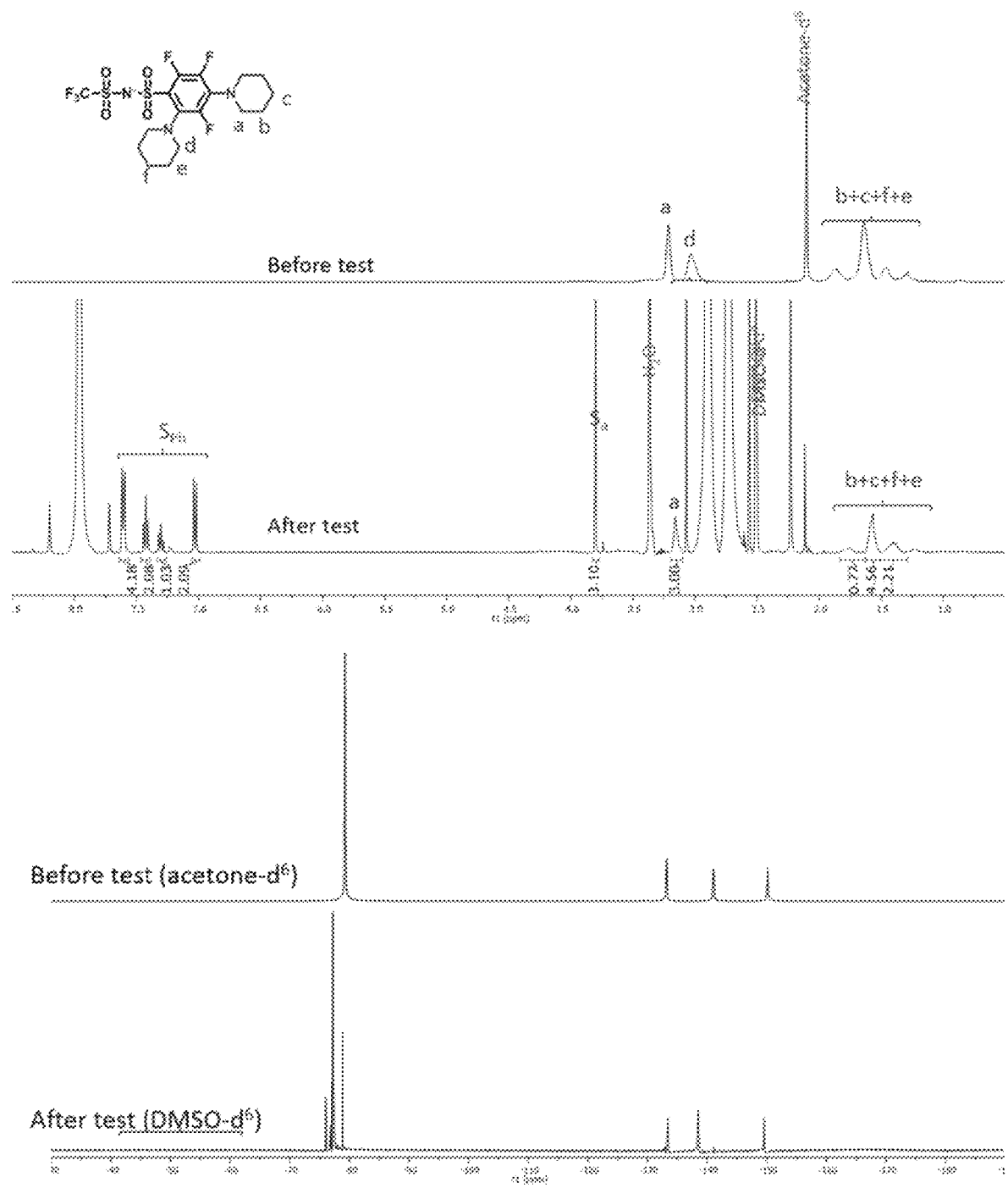
FIG. 28 shows $^1$H and $^{19}$F NMR of A-Pip$_2$F$_3$ before and after stability test in DMF. NMR solvent: d$^6$-Acetone (before stability test) d$^6$-DMSO (after stability test).
Figure 29:
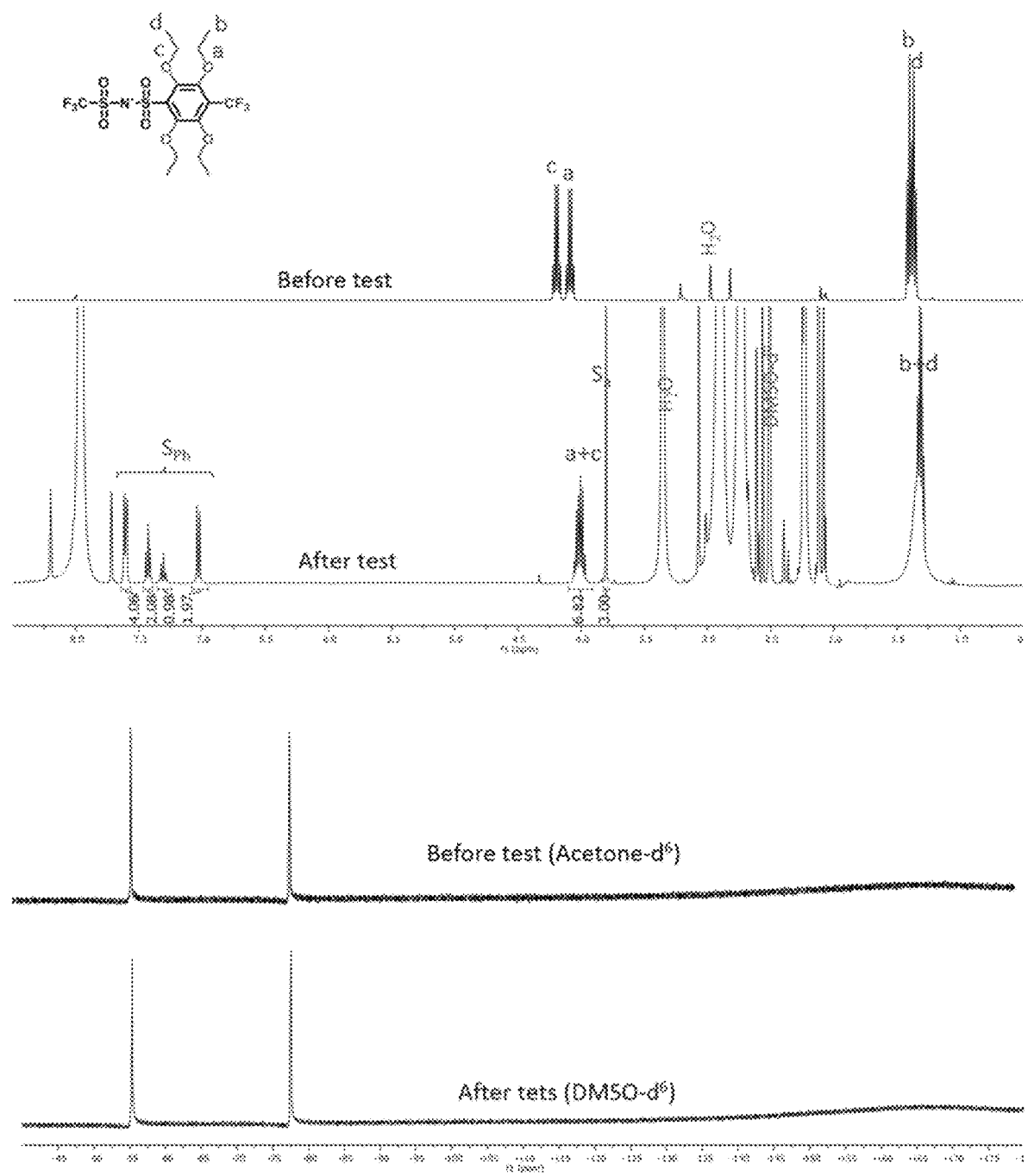
FIG. 29 shows $^1$H and $^{19}$F NMR of B-OEt$_4$ before and after stability test in DMF. NMR solvent: d$^6$-Acetone (before stability test) d$^6$-DMSO (after stability test).
Figure 30:
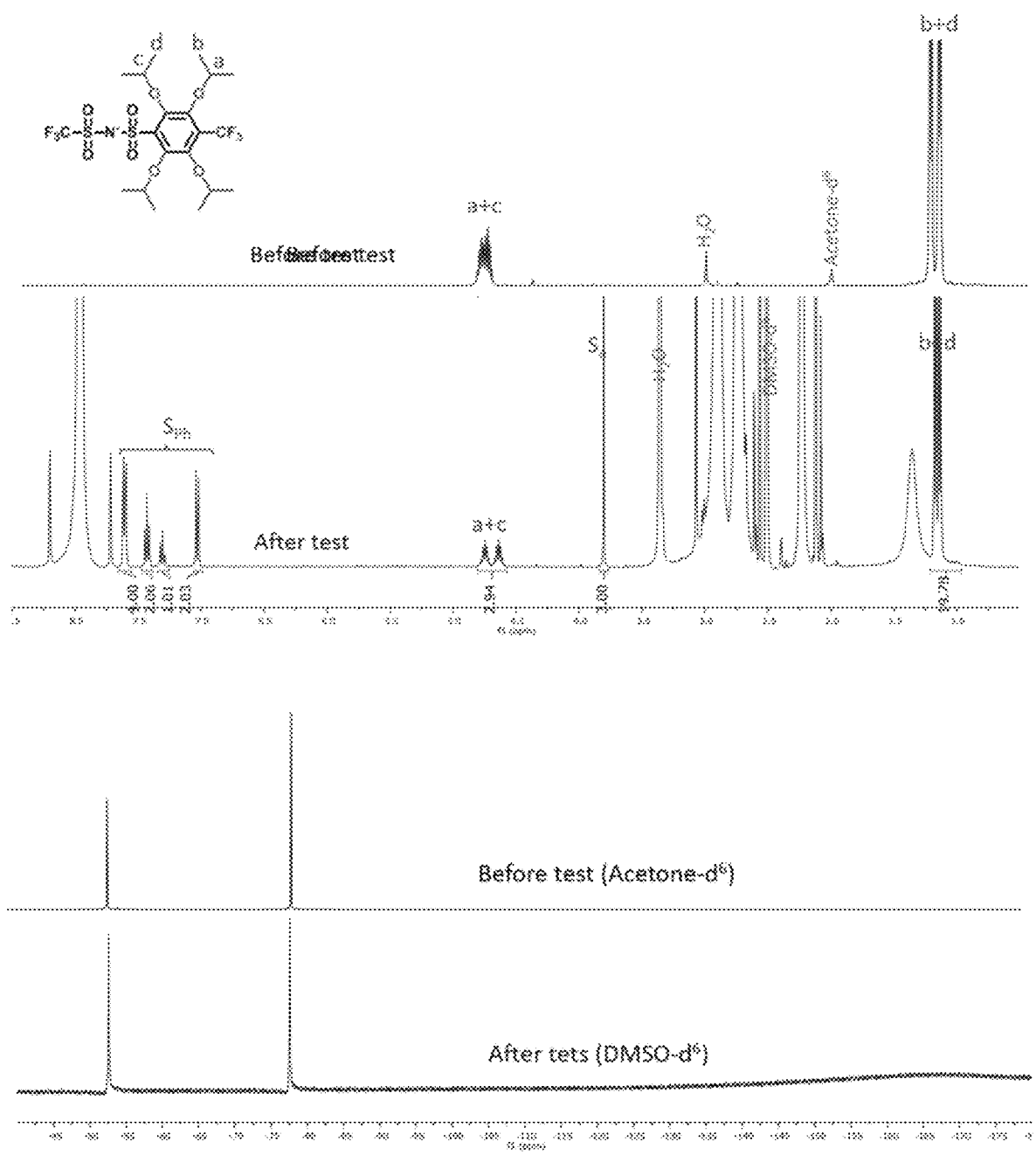
FIG. 30 shows $^1$H and $^{19}$F NMR of B-OiPr$_4$ before and after stability test in DMF. NMR solvent: d$^6$-Acetone (before stability test) d$^6$-DMSO (after stability test).
Figure 31:
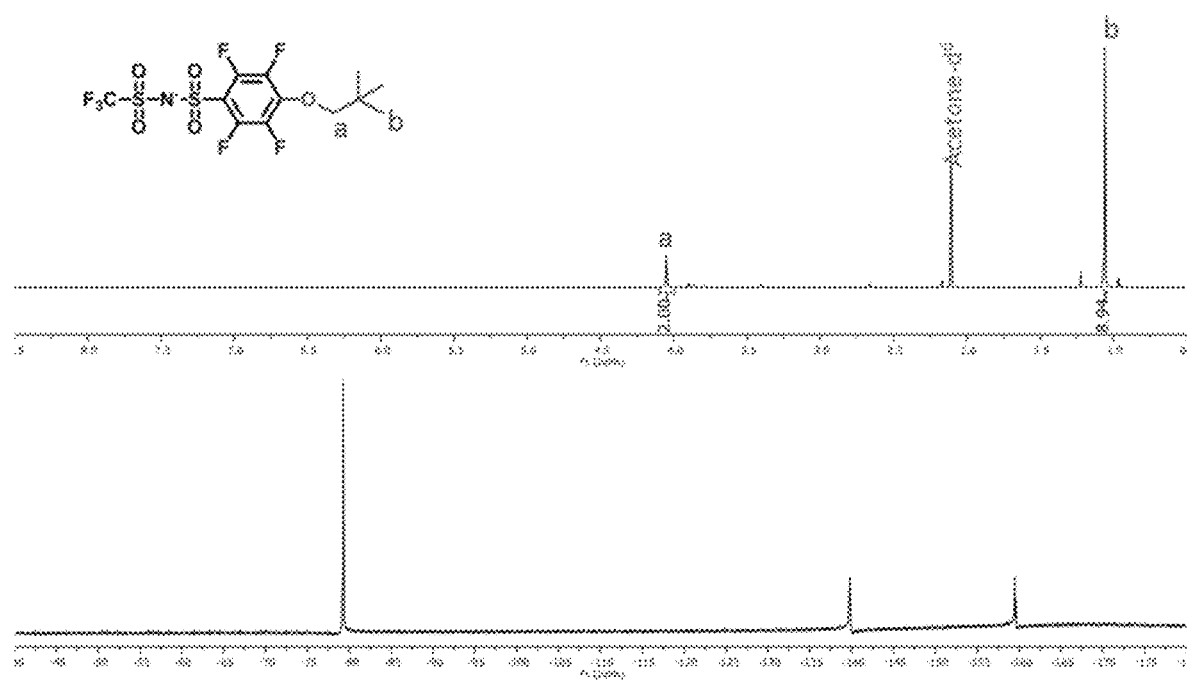
FIG. 31 shows $^1$H and $^{19}$F NMR of A-NeopF$_4$. NMR solvent: d$^6$-Acetone.
Figure 32:
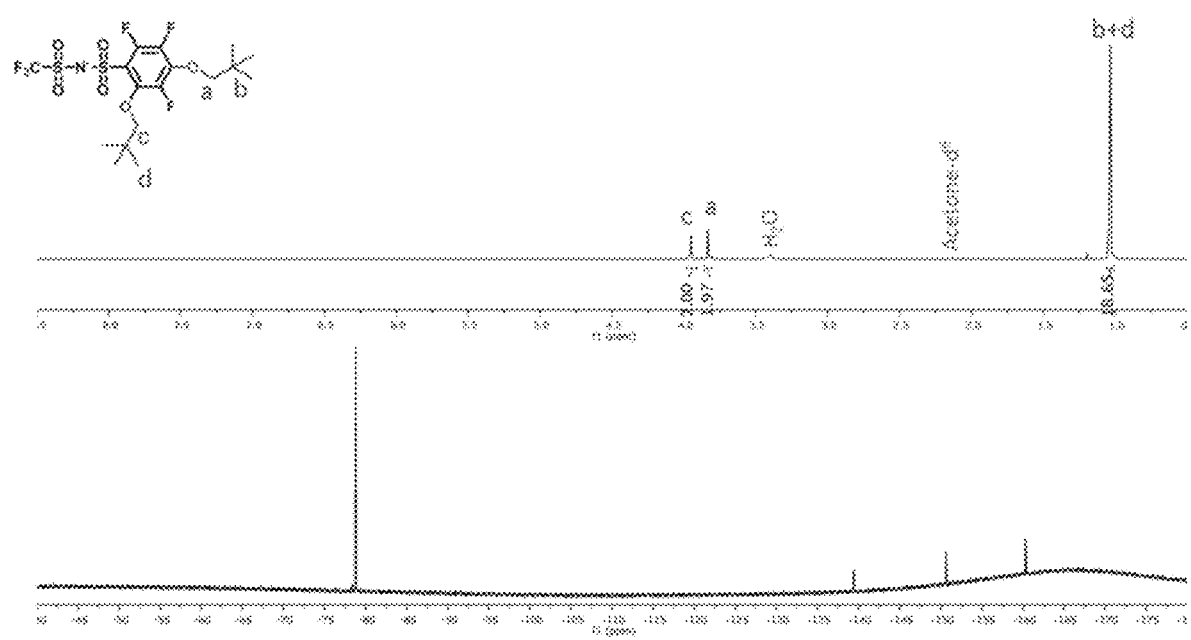
FIG. 32 shows $^1$H and $^{19}$F NMR of A-Neop$_2$F$_3$. NMR solvent: d$^6$-Acetone.
Figure 33:
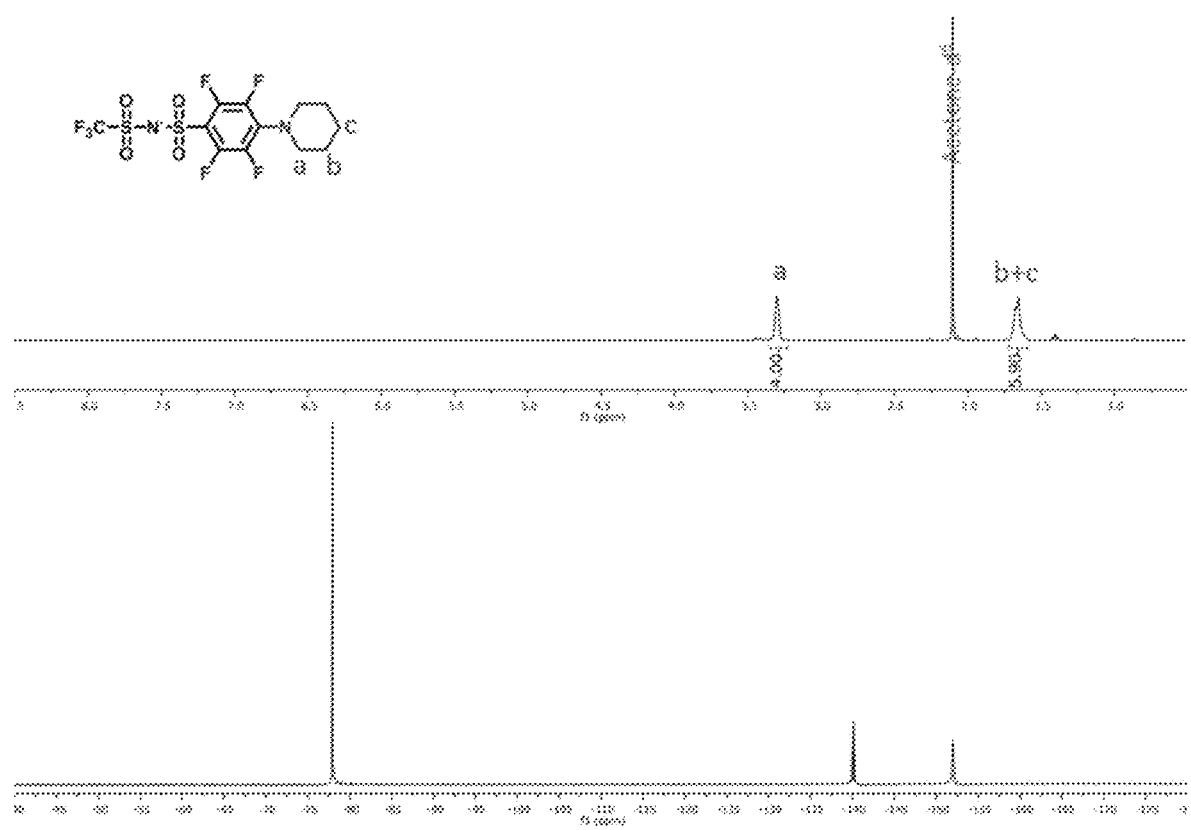
FIG. 33 shows $^1$H and $^{19}$F NMR of A-PipF$_4$. NMR solvent: d$^6$-Acetone.
Figure 34:
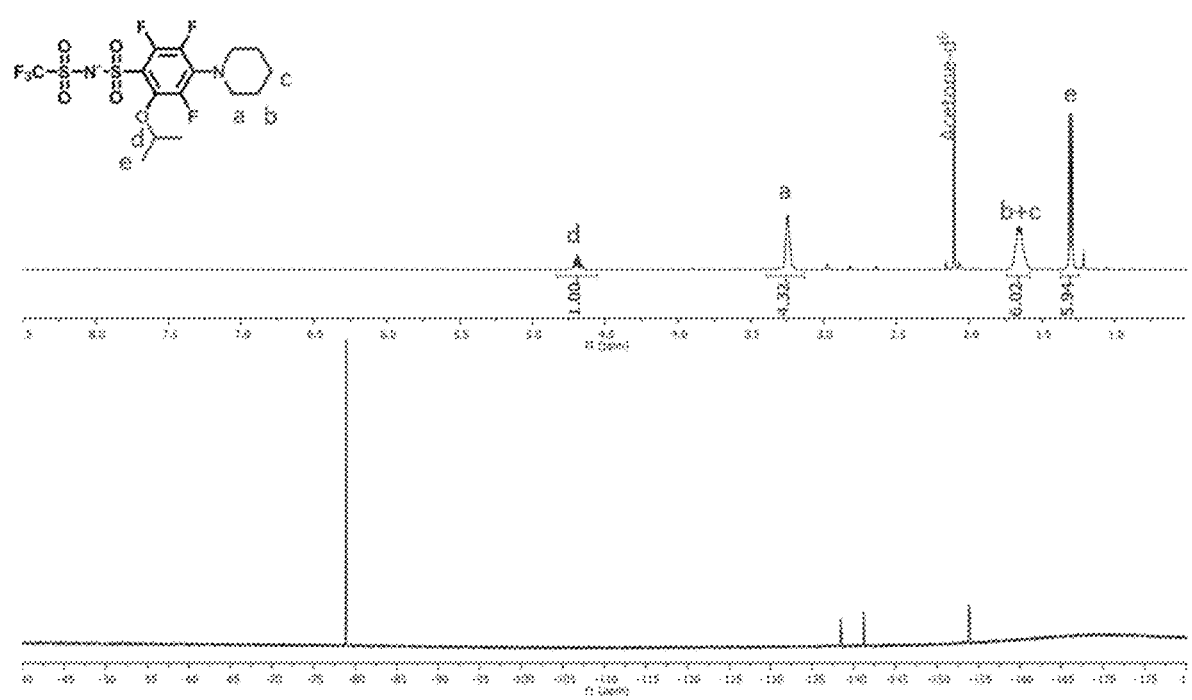
FIG. 34 shows $^1$H and $^{19}$F NMR of A-PipOiPrF$_3$. NMR solvent: d$^6$-Acetone.
Figure 35:
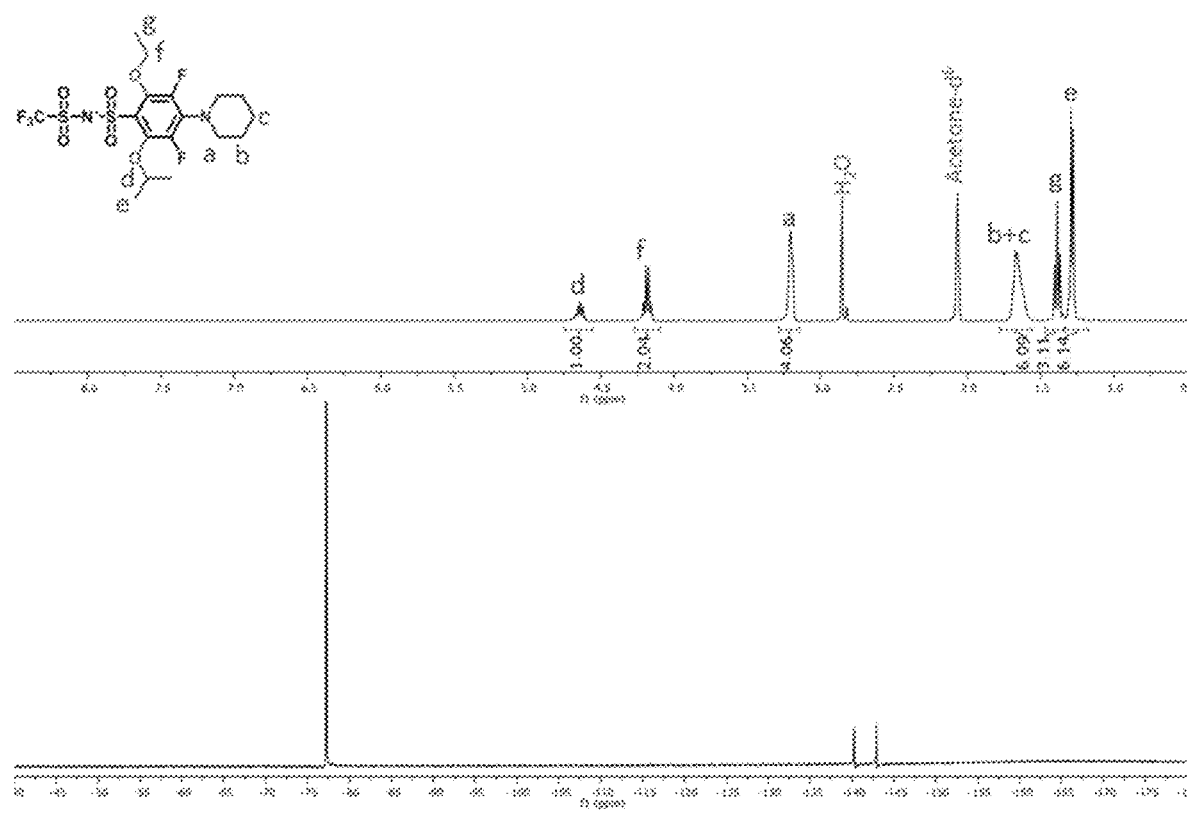
FIG. 35 shows $^1$H and $^{19}$F NMR of A-PipOEtOiPrF$_3$. NMR solvent: d$^6$-Acetone.
Figure 36:
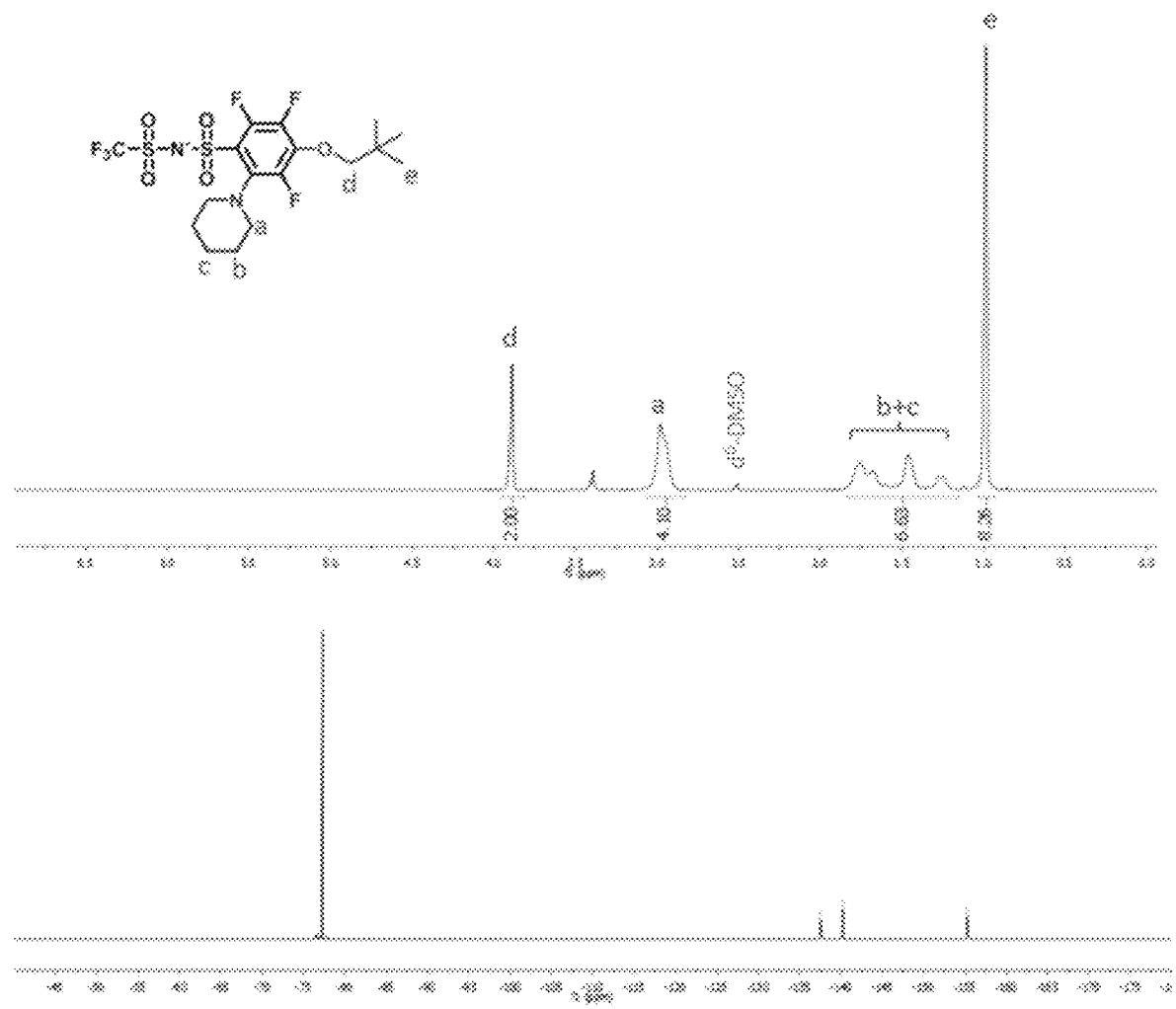
FIG. 36 shows $^1$H and $^{19}$F NMR of A-o-PipONeopF$_3$. NMR solvent: d$^6$-DMSO.
Figure 37:
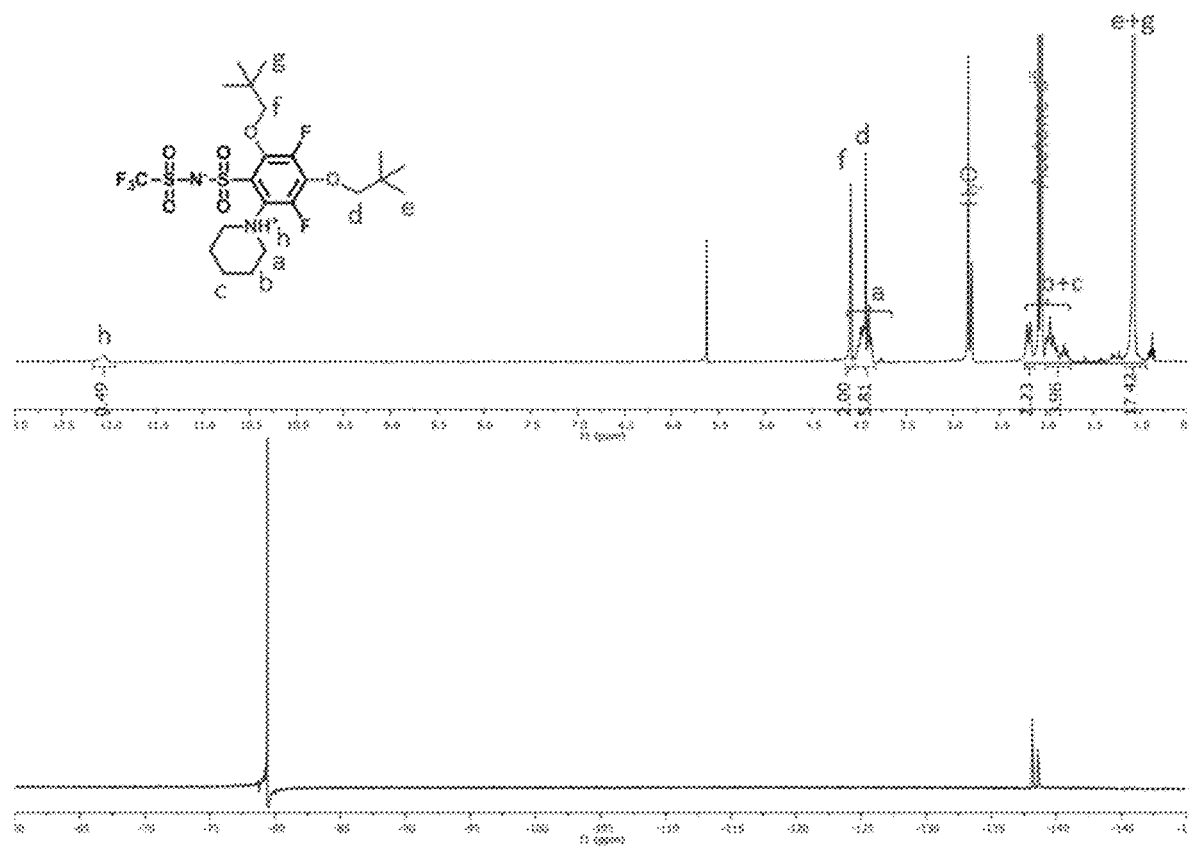
FIG. 37 shows $^1$H and $^{19}$F NMR of A-o-PipONeop$_2$F$_2$●H$^+$. NMR solvent: d$^6$-Acetone.
Figure 38:
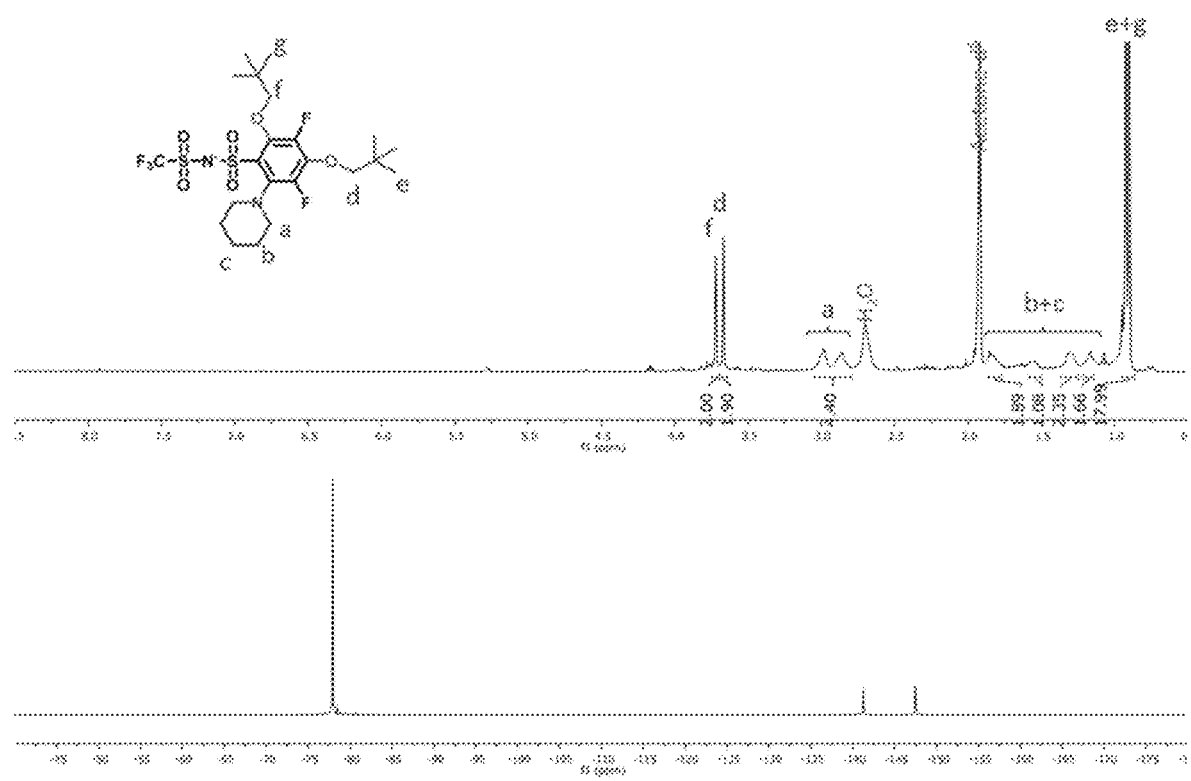
FIG. 38 shows $^1$H and $^{19}$F NMR of A-o-PipONeop$_2$F$_2$. NMR solvent: d$^6$-Acetone.
Figure 39:
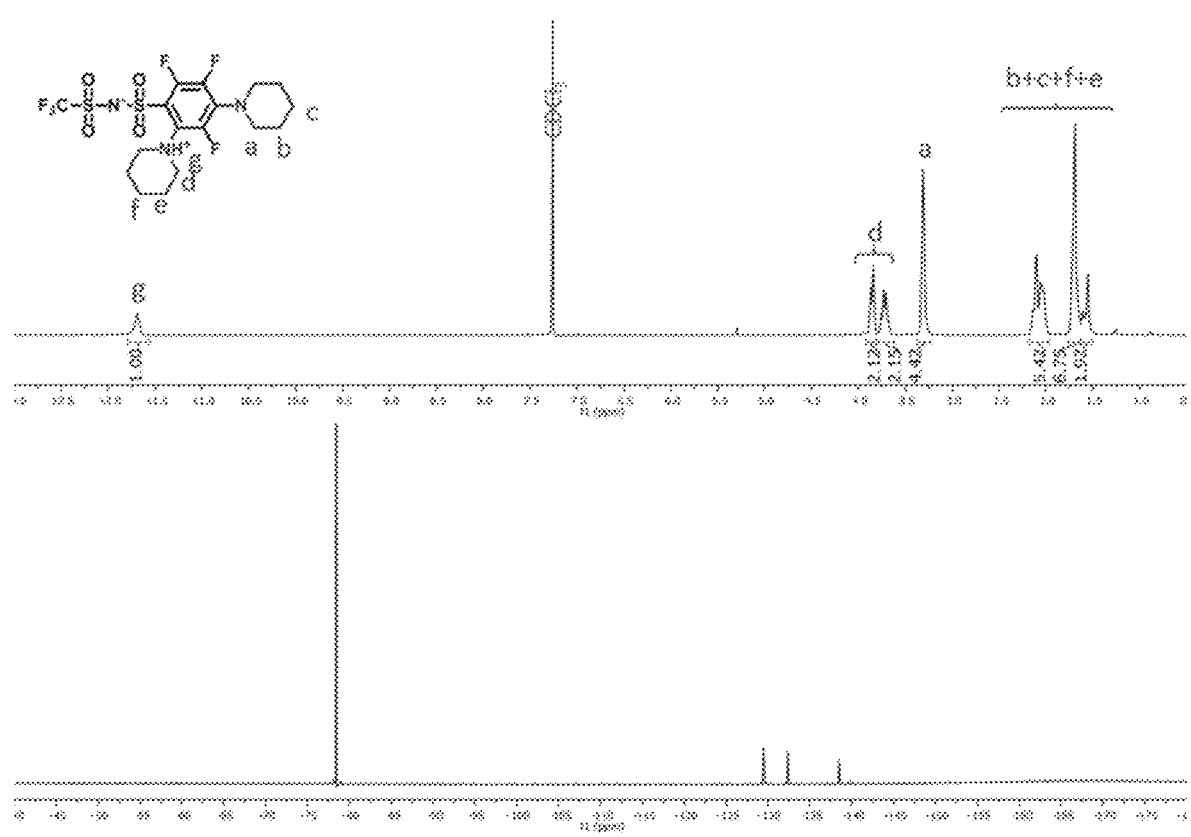
FIG. 39 shows $^1$H and $^{19}$F NMR of A-Pip$_2$F$_3$●H$^+$. NMR solvent: CDCl3.
Figure 40:
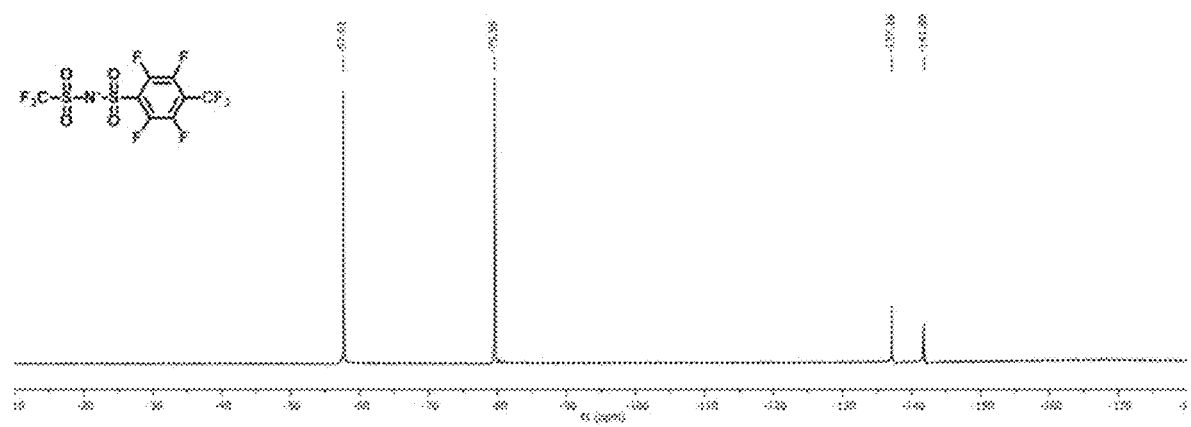
FIG. 40 shows $^{19}$F NMR of B. NMR solvent: d$^6$-Acetone.
Figure 41:
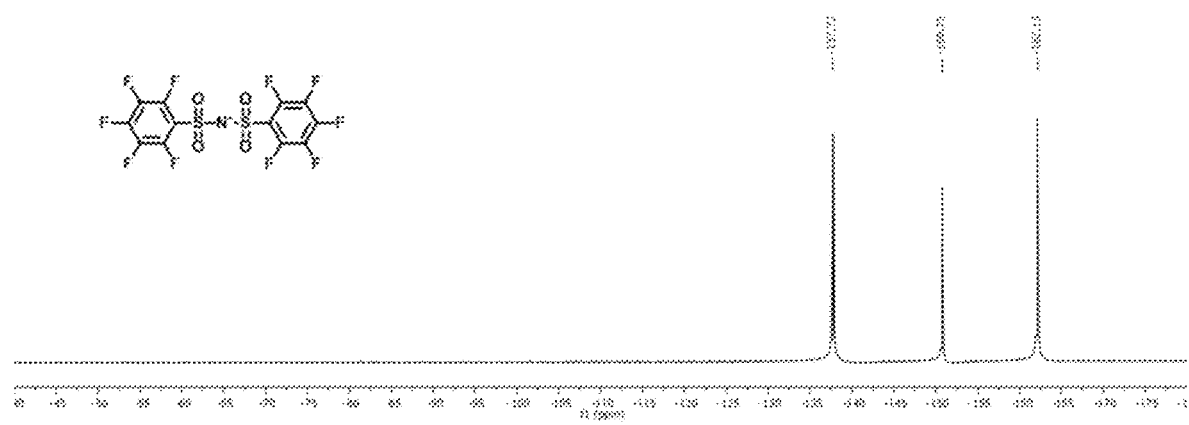
FIG. 41 shows $^{19}$F NMR of C. NMR solvent: d$^6$-Acetone.
Figure 42:
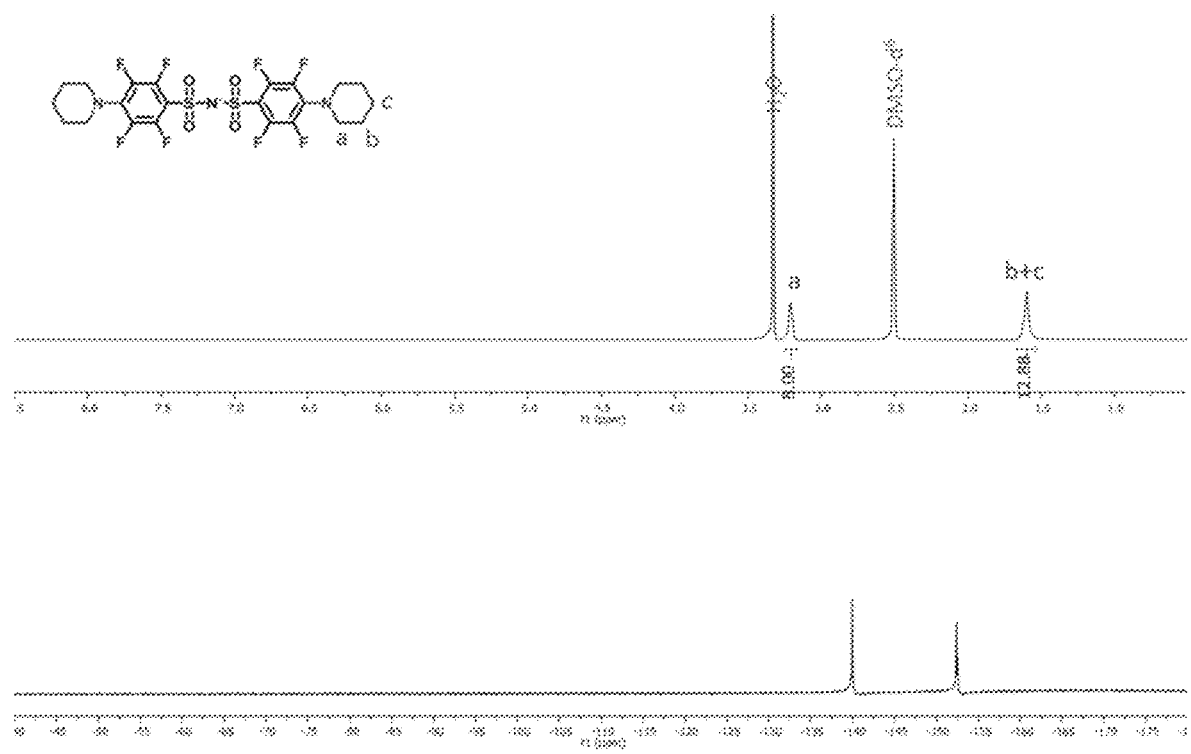
FIG. 42 shows $^1$H and $^{19}$F NMR of C-PipF$_4$. NMR solvent: d$^6$-DMSO.
Figure 43:
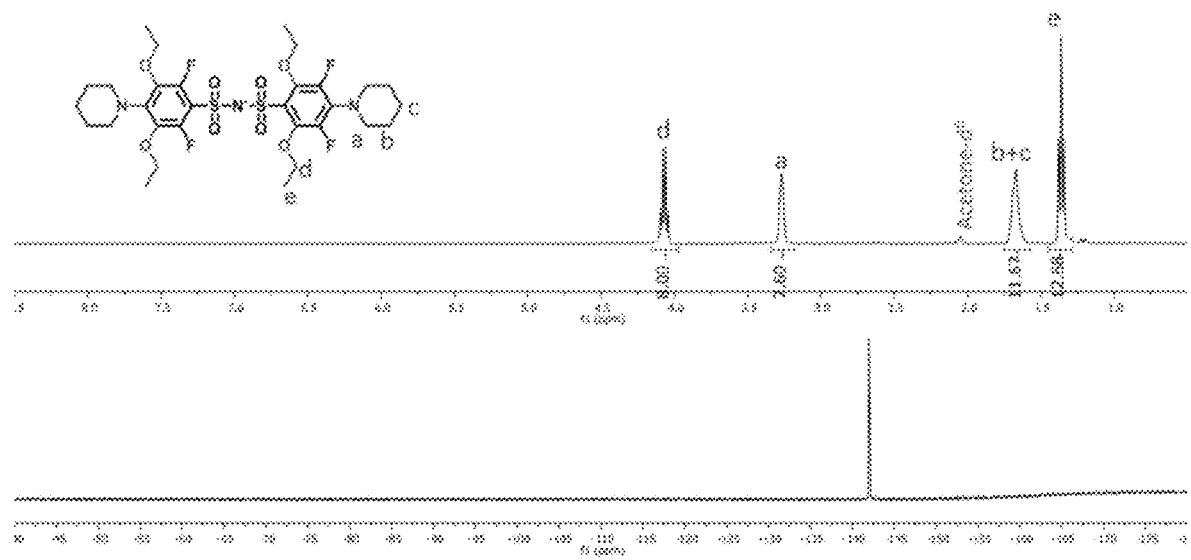
FIG. 43 shows $^1$H and $^{19}$F NMR of C-PipOEt$_2$F$_2$. NMR solvent: d$^6$-Acetone.
Figure 44:
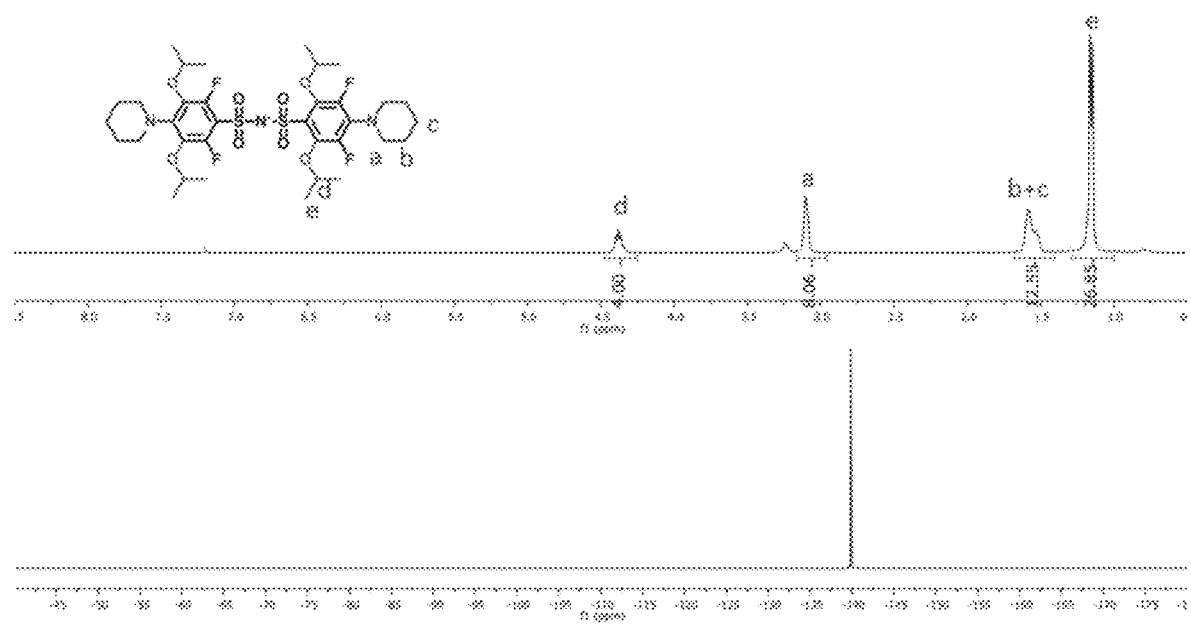
FIG. 44 shows $^1$H and $^{19}$F NMR of C-PipOiPr$_2$F$_2$. NMR solvent: d$^6$-Acetone.

The Li FAST salts could be readily acquired by ion exchange of the Na salts. Four Li salts were prepared from A, A-PipF$_4$, A-ONeop$_3$F$_2$, and A-PipONeop$_2$F$_2$. The $^7Li$ and $^{23}Na$ NMR spectra show nearly complete replacement of $Na^+$ by $Li^+$ in A (FIG. 13). The ionic conductivities of solid-state polymer electrolytes prepared by blending these Li salts with PEO (10 kDa; molar ratio of PEO repeat unit and $Li^+$[EO]:[$Li^+$]=15:1) are shown in FIG. 9A. These FAST-PEO blends exhibited similar ionic conductivities as their corresponding sodium salts in liquid electrolytes: blends with Li salts A and A-PipF$_4$ have ionic conductivities that are 2 and 4 times lower, respectively, than that of LiTFSI. Polymer electrolytes containing Li salts of A-PipONeop$_2$F$_2$ and A-ONeop$_3$F$_2$ showed conductivities in the range from 60° C. to 80° C. that were approximately one order of magnitude lower than that of LiTFSI. As in liquid electrolyte, the lower ion conductivity of FAST-PEO blends can be attributed to higher Lewis basicity of these salts and the formation of more ion pairs (FIG. 9B), leading to lower concentration of charge carriers. Another reason for lower ion conductivity can simply be their larger size, as mobility of the FAST anions with more substitutions would decrease and contribute less to overall ionic conductivity in these polymer electrolytes. Nevertheless, in light of the all of the results discussed above, A-ONeop$_3$F$_2$ shows chemical and oxidative stability on par with TFSI and reasonable conductivity, thus suggesting the potential use of this and other tris-neopentyl substituted FAST salts as functional TFSI replacements.

In summary, a class of sulfonimide salts for solid-state electrolytes can be synthesized based on successive $S_NAr$ reactions of fluorinated phenyl sulfonimides: Fluorinated Aryl Sulfonimide Tags (FAST). Using DFT calculations and experimental measurements, it was demonstrated that the chemical and electrochemical oxidative stability of these FAST salts are inversely correlated with the number of fluorine atoms present on the aromatic ring. FAST salts with strongly electron donating Pip substituents generally showed better chemical stability compared to those with ether substituents; however, the sterically hindered salt A-ONeop$_3$F$_2$ was also highly resistant to chemical degradation. FAST salts with Pip groups were more vulnerable to oxidation than those containing only ether substituents; here again, ONeop$_3$F$_2$ displayed outstanding stability. Other properties like solubility, Lewis basicity, and conductivity can also be tuned by introducing different numbers and types of nucleophilic functional groups to the FAST salt scaffold. FAST salts provide a new anion design strategy, enabling alternatives to TFSI with properties that can be rationally designed in a highly modular fashion. In particular, the ability to readily control the pattern of functionalization on the FAST scaffold and predict the resulting chemical and oxidative stability as well as basicity opens up new opportunities for the design of polymer-FAST conjugates and single-ion conductors, meeting the growing interest of solid-state electrolytes as potentially safe and stable high-energy storage technologies.

Theoretical Calculations

All calculations were performed employing the Gaussian 09 computational package. See M. J. Gaussian, Revision A., Frisch, G. W. Trucks, H. B. Schlegel, G. E. Scuseria, M. A. Robb, J. R. Cheeseman, G. Scalmani, V. Barone, B. Mennucci and G. A. Petersson et al., 2016, which is incorporated by reference in its entirety. Geometries were optimized at the B3LYP/6-31G(d,p) level of theory; ground states were verified by the absence of any imaginary frequency. Natural Population Analysis (NPA) atomic partial charges were obtained using the optimized geometries at B3LYP/6-31G (d,p). See D. Becke, *J. Chem. Phys.*, 1993, 98, 5648, Lee, W. Yang and R. G. Parr, *Phys. Rev. B*, 1988, 37, 785-789, A. E. Reed, R. B. Weinstock, and F. Weinhold, "Natural-population analysis," *J. Chem. Phys.*, 1985, 83, 735-46, and J. P. Foster and F. Weinhold, "Natural hybrid orbitals," *J. Am. Chem. Soc.*, 1980, 102, 7211-18, each of which is incorporated by reference in its entirety. Single point energy calculations were performed at the B3LYP/6-311++G(d,p) level of theory for oxidation energies, nucleophilic substitution free energies, and cation-anion association free energies. The conductor-like polarizable continuum model (CPCM) was employed to capture the solvation effects. See L. Xing, O. Borodin, D. Smith and W. Li, *J. Phys. Chem. C*, 2011, 13896-13905, and S. T. Tti, *Pure Appl. Chem.*, 1986, 58, 955-966, each of which is incorporated by reference in its entirety. Electrochemical oxidative stability is estimated by oxidation energy calculations, which is the Gibbs free energy for the electrochemical oxidation reaction $M \rightarrow M^+ + e^-$ in the solution (Dimethyl sulfoxide (DMSO) was selected as the universal solvent in the electrochemical oxidation energy calculations):

$$G_{Ox} = G(M^+) - G(M)$$

The computed electrochemical oxidation energy, $G_{Ox}$, in eV is converted to the experimentally measured scale versus Li/Li$^+$ by the subtraction of 1.4 V. See M. Cossi, N. Rega, G. Scalmani and V. Barone, *J. Comput. Chem.*, 2003, 24, 669-681, and V. Barone and M. Cossi, *J. Phys. Chem. A*, 1998, 102, 1995-2001, each of which is incorporated by reference in its entirety. The free energies of nucleophilic substitution ($\Delta G_{nuc}$) of select carbon sites in A-OMe$_3$F$_2$, A-PipOMe$_2$F$_2$, and A-Pip$_2$OMeF$_2$ were computed by superoxide in implicit DMSO. To mimic the solvation environment in 1,2-dimethoxyethane (DME) solvent, diethylether was selected as the implicit solvent in the association free energy calculation, and the dielectric constant of the implicit solvent was set to 7.2. The likelihood of cation-anion interaction was estimated by the Gibbs free energy of the reaction M$^+$+A$^-$→MA (M=Na or Li), which is taken to be the association free energy in the solution:

$$\Delta G_{asso} = G(MA) - G(M^+) - G(A^-)$$

G(M$^+$) is approximated according to the reaction M$^+$+2DME→M$^+$(DME)$_2$, where $$G(M^+) = G(M^+(DME)_2) - 2G(DME)$$

Electrochemical Stability Test Details

The sulfonimide compounds were vacuum-dried at 75° C. overnight before being transferred into a glove box (H$_2$O<0.1 ppm, O$_2$<0.1 ppm, MBraun, USA) without exposure to the atmosphere. The oxidative stability of the sulfonimide compounds was studied in electrochemical cells consisting of a Lithium foil (D=15 mm, Chemetall, Germany), 90 μL of 0.02 M sulfonimide sample in propylene carbonate (H$_2$O<20 ppm by Karl Fischer titration, BASF), one piece of glass fiber separator (D=18 mm, Whatman®, Grade GF/A), and a 304 stainless steel mesh as current collector (D=12.7 mm). The assembled electrochemical cells were then transferred to a second glove box (H$_2$O<1 ppm, O$_2$<1%, MBraun, USA) and pressured with dry O$_2$ (99.994% purity, H$_2$O<2 ppm, Airgas, USA) to 30 psi (gauge). In each electrochemical stability test, after holding the cell at open circuit voltage for two hours, a series of potentials were applied sequentially for three hours each: 3.0, 3.2, 3.4, 3.6, 3.8, 4.0, 4.2, 4.4, and 4.5 V; the current response was recorded throughout the test. All electrochemical tests were conducted employing a VMP3 potentiostat (BioLogic Science Instruments).

Conductivity Measurement Details

The impedance measurements were conducted using electrochemical cells consisting of liquid or polymer electrolytes sandwiched between two stainless steel blocking electrodes (D=15.5 mm). The liquid electrolyte contained one piece of Celgard 2340 separator (thickness=38 μm, porosity=0.45) impregnated with 100 μL of 0.1 M sulfonimide sample in 1,2-dimethoxyethane (purchased from Acros, degassed and dried using a glass contour solvent purification system by SG Water USA, LLC), whereas the polymer electrolytes contained 10 k PEO-sulfonimide blends ([EO]:[Li$^+$]=15:1). The conductivity was studied with electrochemical impedance spectroscopy (EIS, VMP3, Bio-Logic *Science* Instruments) over the frequency range of 1 MHz and 0.1 Hz at a voltage amplitude of 10 mV. The bulk electrolyte conductivity, a, is estimated from the bulk electrolyte resistance, R, obtained in the EIS measurement according to the equation $$\sigma = \frac{1}{R}\frac{d}{A}$$

where d is the thickness of the electrolyte (i.e., the thickness of the separator for liquid electrolyte, and the thickness of the PEO-sulfonimide sample for polymer electrolyte) and A is the cross-sectional area of tested sample.

$^{23}$Na NMR Measurement of Interaction Between Anion and Cations Among FAST Salts For A type FAST salts, nitromethane was chosen as the solvent since it has lower value of Gutmann's donor numbers than TFSI anion. See R. H. Erlich, A. I. Popov, *J. Am. Chem. Soc.*, 5620-5623 (1971), and M. Schmeisser, P. Illner, R. Puchta, A. Zahl, R. van Eldik, *Chemistry* 18, 10969-10982 (2012), each of which is incorporated by reference in its entirety. FAST salts were dissolved in nitromethane to prepare 0.1 M solution and loaded into thin wall NMR tube. The inner reference was a 0.25 M DMSO solution of sodium perchlorate. For measurements, the reference solution was placed in a capillary sealed by PTFE cap and inserted coaxially into the sample NMR tube. The $^{23}$Na spectra were collected at Bruker 106 MHz, and the chemical shift of the reference was set to 0 ppm. Since B type and C type salts have low solubility in nitromethane, acetonitrile was chosen as the solvent. The reference and measurement details were the same as in A type salts.

TABLE 1

| | Crystal data | | | |
|---|---|---|---|---|
| | A11 | A12 | A13 | S2 |
| Empirical formula | $C_{24}H_{20}F_3N_2NaO_6S_2$ | $C_{14}H_{18}F_5N_2NaO_7S_2$ | $C_{16}H_{20}F_5N_2NaO_6S_2$ | $C_{17}H_{21}F_6N_3O_4S_2$ |
| a | 43.264 Å | 7.958 Å | 5.399 Å | 8.153 Å |
| b | 5.590 Å | 28.725 Å | 11.412 Å | 11.052 Å |
| c | 24.240 Å | 8.954 Å | 18.037 Å | 12.536 Å |
| α (alpha): | 90.00° | 90.00° | 82.42° | 99.43° |
| β (beta): | 119.48° | 91.06° | 82.10° | 94.08° |
| γ (gamma): | 90.00° | 90.00° | 86.02° | 110.56° |
| Volume: | 5103.33 Å$^3$ | 2046.48 Å$^3$ | 1089.67 Å$^3$ | 1033.16 Å$^3$ |
| Space group: | C2/c | P2$_1$/n | P-1 | P-1 |
| Calculated density: | 1.600 g/cm$^3$ | 1.650 g/cm$^3$ | 1.580 g/cm$^3$ | 1.638 g/cm$^3$ |
| Color: | colourless | colourless | colourless | colourless |
| Z: | 8 | 4 | 2 | 2 |
| Temperature: | −173.0° C. | −173.0° C. | −123.0° C. | −173.0° C. |
| Formula weight: | 614.546 g/mole | 508.420 g/mole | 518.458 g/mole | 509.494 g/mole |

TABLE 1-continued

| | Crystal data | | | |
|---|---|---|---|---|
| | A11 | A12 | A13 | S2 |
| R(F): | 0.0386 | 0.0741 | 0.0321 | 0.0301 |
| $R_w(F^2)$: | 0.0969 | 0.1601 | 0.0891 | 0.0836 |

TABLE 2

Melting points of representative salts

| Samples (sodium salts) | $T_m$ (° C.) |
|---|---|
| A-PipOMe$_2$F$_2$ | 264-265 |
| A-PipOEt$_2$F$_2$ | 252-253 |
| A-PipOiPr$_2$F$_2$ | 235-239 |
| A-PipONeop$_2$F$_2$ | 216-222 |
| A-ONeop$_3$F$_2$ | 206-214 |

Synthesis Part 2,3,4,5,6-pentafluoro-N-[(trifluoromethyl)sulfonyl]benzene sulfonamide (A): To a 100 mL round-bottomed flask equipped with a magnetic stirring bar were added trifluoromethane sulfonamide (10.0 mmol), N-methylmorpholine (20.0 mmol), and 50 mL DCM. The mixture was cooled to 0° C. With stirring, 2,3,4,5,6-pentafluorobenzene sulfonyl chloride (10.5 mmol) in 10 mL DCM was added dropwise via dropping funnel. The solution was further stirred at room temperature for 24 h. After removing DCM solvent under vacuum, the residue was dissolved in 100 mL ethyl acetate, and washed with 1M hydrochloric acid (1×50 mL), water (1×40 mL) and brine solution (2×40 mL). Then organic layer was dried over anhydrous sodium sulfate and concentrated in vacuum. The residue was purified by flash chromatography on silica gel with acetone/hexanes (v/v=1/2) as the eluent to afford the product as a white solid (3.28 g, 82%). $^{13}$C NMR (126 MHz, acetone-d$^6$, ppm, S): 139.53 (dm, J=255.7 Hz), 138.33 (dm, J=257.0 Hz), 132.84 (dm, J=253.2 Hz), 115.14 (q, J=321.7 Hz), 115.27-114.30 (m). $^{19}$F NMR (125 MHz, acetone-d$^6$, ppm, δ): −79.33, −137.86, −152.84, −164.07. MS (m/z): Calc. for C$_7$NF$_9$O$_4$S$_2$Na: 400.9. Found (M-Na)$^-$: 377.9. A-ONeopF$_4$ & A-ONeop$_2$F$_3$: To a 20 mL vial equipped with a magnetic stirring bar were added dry neopentanol (5.7 mmol), sodium hydride (5.7 mmol) and 5 mL dry DMF under nitrogen. After stirred at room temperature for 0.5 h, the mixture was transferred dropwise to another 40 ml vial which has been charged with A (4.0 mmol) and 5 mL DMF first. The solution was quenched by adding 5 ml 1M HCl aqueous solution after further stirred at room temperature for 2 h. Then ethyl acetate (2×50 mL) was added to extract crude product, and washed with water (1×30 mL) and brine solution (2×30 mL). Then organic layer was dried over anhydrous sodium sulfate and concentrated in vacuum. The residue was purified by flash chromatography on silica gel with acetone/hexanes (v/v=1/2) as the eluent to afford the products as white foam solids.

A-ONeopF$_4$:(0.79 g, 42%). $^1$H NMR (400 MHz, acetone-d$_6$, ppm) δ: 4.05 (s, 2H), 1.06 (s, 9H). $^{13}$C NMR (126 MHz, acetone-d$_6$, ppm) δ:145.44 (dm, J=253.3 Hz), 140.61 (dm, J=245.0 Hz), 141.03-140.32 (m), 120.19 (q, J=320.0 Hz), 118.61-117.32 (m), 84.72, 32.40, 25.31. $^{19}$F NMR (376 MHz, acetone-d$_6$, ppm) δ: −79.23, −139.80, −159.45. MS (m/z): Calc. for C$_{12}$H$_{11}$NF$_7$O$_5$S$_2$Na: 468.99. Found (M-Na)$^-$: 446.0.

A-ONeop$_2$F$_3$:(0.77 g, 36%). $^1$H NMR (400 MHz, acetone-d$_6$, ppm) δ: 3.95 (s, 2H), 3.84 (s, 2H), 1.04 (s, 9H), 1.03 (s, 9H). $^{13}$C NMR (126 MHz, acetone-d$_6$, ppm) δ: 146.06 (dm, J=246.9 Hz), 144.65 (dm, J=252.0 Hz), 142.35 (m), 140.37 (dm, J=245.7 Hz), 140.70-140.05 (m), 120.28 (q, J=322.6 Hz), 123.46-122.40 (m), 84.55, 84.13, 32.40, 32.12, 26.06, 25.45. $^{19}$F NMR (376 MHz, acetone-d$_6$, ppm) δ: −78.78, −139.45, −150.64, −160.30. MS (m/z): Calc. for C$_{17}$H$_{22}$NF$_6$O$_6$S$_2$Na: 537.07. Found (M-Na)$^-$: 514.1.

General Procedure for A-OR$_3$F$_2$

A 40 mL vial equipped with a magnetic stirring bar was charged with A (1.2 mmol) and 5 mL dry DMF. Then corresponding sodium phenoxide or alkoxide (6.0 mmol) was added under nitrogen. After stirred at room temperature (90° C. for sodium phenoxide) for 12 h, the solution was quenched by adding 10 ml 1M HCl aqueous solution. Then ethyl acetate (2×30 mL) was added to extract crude product, and washed with water (1×20 mL) and brine solution (2×20 mL). The organic layer was dried over anhydrous sodium sulfate and concentrated in vacuum. The residue was purified by flash chromatography on silica gel with acetone/hexanes (v/v=1/2) as the eluent to afford the products as white solids.

A-OPh$_3$F$_2$:(0.62 g, 83%). $^1$H NMR (400 MHz, acetone-d$_6$, ppm) δ: 7.45-7.30 (m, 4H), 7.17-7.02 (m, 6H). $^{13}$C NMR (101 MHz, acetone-d$_6$, ppm) δ: 158.50, 157.14, 146.88 (dd, J=252.9, 3.4 Hz), 138.48 (dd, J=11.6, 4.3 Hz), 135.68 (t, J=13.0 Hz), 131.25, 130.10, 129.40, 123.88, 122.64, 120.77 (q, J=304.0 Hz), 115.90, 115.26. $^{19}$F NMR (376 MHz, acetone-d$_6$, ppm) δ: −77.26, −142.07. MS (m/z): Calc. for C$_{25}$H$_{15}$NF$_5$O$_7$S$_2$Na: 623.01. Found (M-Na)$^-$: 599.9.

A-OMe$_3$F$_2$:(0.29 g, 55%). $^1$H NMR (400 MHz, acetone-d$_6$, ppm) δ: 4.02 (s, 3H), 3.80 (s, 6H). $^{13}$C NMR (101 MHz, acetone-d$_6$, ppm) δ: 145.90 (dd, J=244.3, 4.7 Hz), 143.02 (dd, J=11.5, 4.2 Hz), 139.92 (t, J=12.9 Hz), 128.17, 120.47 (q, J=324.9 Hz), 62.62, 62.30. $^{19}$F NMR (376 MHz, acetone-d$_6$, ppm) δ: −79.02, −151.70. MS (m/z): Calc. for C$_{10}$H$_9$NF$_5$O$_7$S$_2$Na: 437.28. Found (M-Na)$^-$: 414.2.

A-OEt$_3$F$_2$:(0.40 g, 70%). $^1$H NMR (400 MHz, acetone-d$_6$, ppm) δ: 4.29 (q, J=8.0 Hz, 2H), 4.17 (t, J=8.0 Hz, 4H), 1.40-1.30 (t, 9H). $^{13}$C NMR (101 MHz, acetone-d$_6$, ppm) δ: 146.34 (dd, J=244.5, 4.6 Hz), 142.00 (dd, J=11.8, 4.3 Hz), 139.23 (t, J=13.6 Hz), 127.55, 120.24 (q, J=322.7 Hz), 71.59, 70.47, 14.87, 14.67. $^{19}$F NMR (376 MHz, acetone-d$_6$, ppm) δ: −78.93, −150.74. MS (m/z): Calc. for C$_{13}$H$_{15}$NF$_5$O$_7$S$_2$Na: 479.36. Found (M-Na)$^-$: 456.0.

A-OiPr$_3$F$_2$:(0.49 g, 78%). $^1$H NMR (400 MHz, DMSO-d$_6$, ppm) δ: 4.67-4.55 (m, 2H), 4.53-4.40 (m, 1H), 1.28 (d, J=8.0 Hz, 6H), 1.21 (d, J=8.0 Hz, 12H). $^{13}$C NMR (101 MHz, acetone-d$_6$, ppm) δ: 146.73 (dd, J=242.5, 4.5 Hz), 140.77 (dd, J=11.8, 4.1 Hz), 137.70 (t, J=14.3 Hz), 128.93, 120.37 (q, J=323.2 Hz), 78.19-77.31 (m), 77.44, 21.72, 21.41. $^{19}$F NMR (376 MHz, DMSO-d$_6$, ppm) δ: −77.31, −146.44. MS (m/z): Calc. for C$_{16}$H$_{21}$NF$_5$O$_7$S$_2$Na: 521.06. Found (M-Na)$^-$: 497.9.

A-ONeop$_3$F$_2$:(0.54 g, 75%). $^1$H NMR (400 MHz, acetone-d$_6$, ppm) δ: 3.88 (s, 2H), 3.82 (s, 4H), 1.05 (s, 9H), 1.04 (s, 18H). $^{13}$C NMR (101 MHz, acetone-d$_6$, ppm) δ: 146.07 (dd, J=244.2, 4.6 Hz), 142.61 (dd, J=11.0, 4.2 Hz), 140.04 (t, J=13.3 Hz), 128.39, 120.47 (q, J=323.6 Hz), 84.33, 84.16, 32.39, 32.13, 26.16, 25.55. $^{19}$F NMR (376 MHz, acetone-d$_6$, ppm) δ: −78.19, −145.87. MS (m/z): Calc. for C$_{22}$H$_{33}$NF$_5$O$_7$S$_2$Na: 605.15. Found (M-Na)$^-$: 582.1.

A-PipF$_4$: To a 50 mL round-bottomed flask equipped with a magnetic stirring bar were added A (5.0 mmol), piperidine (7.5 mmol), triethylamine (10.0 mmol), and 20 mL acetonitrile. The mixture was further stirred at room temperature for 12 h. After removing acetonitrile under vacuum, the residue was dissolved in 30 mL ethyl acetate, and washed with 1M hydrochloric acid (1×20 mL), water (1×20 mL) and brine solution (2×20 mL). Then organic layer was dried over anhydrous sodium sulfate and concentrated in vacuum. The residue was purified by flash chromatography on silica gel with acetone/hexanes (v/v=1/2) as the eluent to afford the product as a pale yellow solid (1.86 g, 80%). $^1$H NMR (400 MHz, acetone-d$_6$, ppm) δ: 3.33-3.27 (m, 4H), 1.75-1.60 (m, 6H). $^{13}$C NMR (101 MHz, acetone-d$_6$, ppm) δ: 144.54 (dm, J=253.5 Hz), 141.24 (dm, J=243.4 Hz), 133.53 (m), 120.25 (q, J=323.9 Hz), 115.76 (m), 51.81, 26.27, 23.74. $^{19}$F NMR (376 MHz, acetone-d$_6$, ppm) δ: −77.96, −140.13, −151.99. MS (m/z): Calc. for C$_{12}$H$_{10}$N$_2$F$_7$O$_4$S$_2$Na: 466.0. Found (M-Na)$^-$: 443.0.

A-PipOiPrF$_3$: To a 40 mL vial equipped with a magnetic stirring bar were added A-PipF$_4$ (1.0 mmol) and 5 mL DMF. Sodium isopropoxide (1.0 mmol) was then added under nitrogen and stirred at room temperature for 2 h. The reaction was quenched by adding 2 mL 1M hydrochloric acid, and diluted with 30 mL ethyl acetate. The organic layer was washed with water (1×20 mL) and brine solution (2×20 mL), dried over anhydrous sodium sulfate and concentrated in vacuum. The residue was purified by flash chromatography on silica gel with acetone/hexanes (v/v=1/2) as the eluent to afford the product as pale yellow solid (0.26 g, 52%). $^1$H NMR (400 MHz, acetone-d$_6$, ppm) δ: 4.75-4.63 (m, 1H), 3.32-3.20 (m, 4H), 1.72-1.57 (m, 6H), 7.56 (dd, J=6.2, 1.2 Hz, 6H. $^{13}$C NMR (101 MHz, acetone-d$_6$, ppm) δ: 147.22 (dm, J=243.41), 145.29 (dm, J=251.49 Hz), 142.67 (dd, J=16.5, 6.5 Hz), 141.07-139.28 (m), 133.80-132.50 (m), 121.57 (d, J=11.4 Hz), 120.35 (q, J=281.8 Hz), 77.97, 51.94, 26.36, 23.86, 21.47. $^{19}$F NMR (376 MHz, acetone-d$_6$, ppm) δ: −78.94, −138.46, −141.21, −153.83. MS (m/z): Calc. for C$_{15}$H$_{17}$N$_2$F$_6$O$_5$S$_2$Na: 506.0. Found (M-Na)$^-$: 482.9.

General Procedure for A-PipOR$_2$F$_2$

A 40 mL vial equipped with a magnetic stirring bar was charged with A-PipF$_4$ (1.2 mmol) and 5 mL dry DMF. Then corresponding sodium phenoxide or alkoxide (4.0 mmol) was added under nitrogen. After stirred at room temperature (90° C. for sodium phenoxide) for 12 h, the solution was quenched by adding 10 ml 1M HCl aqueous solution. Then ethyl acetate (2×30 mL) was added to extract crude product, and washed with water (1×20 mL) and brine solution (2×20 mL). The organic layer was dried over anhydrous sodium sulfate and concentrated in vacuum. The residue was purified by flash chromatography on silica gel with acetone/hexanes (v/v=1/2) as the eluent to afford the products as white solids.

A-PipOPh$_2$F$_2$ (0.63 g, 85%). $^1$H NMR (400 MHz, DMSO-d$_6$, ppm) δ: 7.35-7.25 (m, 4H), 7.07-7.00 (m, 2H), 6.95-6.87 (m, 4H), 3.15-3.08 (m, 4H), 1.58-1.50 (m, 6H). $^{13}$C NMR (101 MHz, acetone-d$_6$, ppm) δ: 158.78, 147.40 (dd, J=247.9, 6.7 Hz), 137.79 (dd, J=12.1, 5.7 Hz), 133.71 (t, J=11.7 Hz), 129.15, 126.59, 122.04, 120.51 (q, J=317.2 Hz), 115.80, 51.93, 26.31, 23.80. $^{19}$F NMR (376 MHz, DMSO-d$_6$, ppm) δ: −77.24, −137.96. MS (m/z): Calc. for C$_{24}$H$_{20}$N$_2$F$_5$O$_6$S$_2$Na: 614.06. Found (M-Na)$^-$: 591.1. $^{13}$C NMR (101 MHz, Acetone-d$_6$) δ.

A-PipOMe$_2$F$_2$ (0.40 g, 68%). $^1$H NMR (400 MHz, acetone-d$_6$, ppm) δ: 3.90 (s, 8H), 3.26-3.20 (m, 4H), 1.73-1.57 (m, 6H). $^{13}$C NMR (100 MHz, acetone-d$_6$, ppm) δ: 147.33 (dd, J=250.0, 4.0 Hz), 144.52 (dd, J=13.1, 4.0 Hz), 134.52 (t, J=11.2 Hz), 129.04, 121.24 (q, J=324.5 Hz), 63.44, 57.20, 24.75, 22.17. $^{19}$F NMR (376 MHz, acetone-d$_6$, ppm) δ: −79.56, −144.30. MS (m/z): Calc. for C$_{14}$H$_{16}$N$_2$F$_5$O$_6$S$_2$Na: 490.03. Found (M-Na)$^-$: 466.9.

A-PipOEt$_2$F$_2$ (0.46 g, 74%). $^1$H NMR (400 MHz, acetone-d$_6$, ppm) δ: 4.02 (q, J=8.0 Hz, 4H), 3.11-3.03 (m, 4H), 1.58-1.40 (m, 6H), 1.22 (t, J=8.0 Hz, 6H). $^{13}$C NMR (101 MHz, acetone-d$_6$, ppm) δ: 147.50 (dd, J=242.9, 6.6 Hz), 141.99 (dd, J=12.6, 4.8 Hz), 133.18 (t, J=12.3 Hz), 126.10, 120.33 (q, J=323.0 Hz), 71.20, 52.04, 26.44, 23.95, 14.76. $^{19}$F NMR (376 MHz, acetone-d$_6$, ppm) δ: −78.70, −143.91. MS (m/z): Calc. for C$_{16}$H$_{20}$N$_2$F$_5$O$_6$S$_2$Na: 518.06. Found (M-Na)$^-$: 495.0.

A-PipOiPr$_2$F$_2$:(0.47 g, 72%). $^1$H NMR (400 MHz, DMSO-d$_6$, ppm) δ: 4.62-4.50 (m, 2H), 3.15-3.07 (m, 4H), 1.65-1.50 (m, 6H), 1.20 (d, J=8.0 Hz, 12H). $^{13}$C NMR (101 MHz, acetone-d$_6$, ppm) δ: 147.36 (dd, J=241.6, 6.6 Hz), 140.67 (dd, J=12.4, 4.7 Hz), 132.67 (t, J=12.8 Hz), 127.10, 120.36 (q, J=323.1 Hz), 77.48, 52.08, 26.46, 23.97, 21.45. $^{19}$F NMR (376 MHz, DMSO-d$_6$, ppm) δ: −77.55, −140.70. MS (m/z): Calc. for C$_{18}$H$_{24}$N$_2$F$_5$O$_6$S$_2$Na: 546.09. Found (M-Na)$^-$: 522.9.

A-PipONeop$_2$F$_2$:(0.59 g, 81%). $^1$H NMR (400 MHz, acetonitrile-d$_3$, ppm) δ: 3.77 (s, 4H), 3.24-3.17 (m, 4H), 1.72-1.57 (m, 6H), 1.05 (s, 18H). $^{13}$C NMR (101 MHz, acetone-d$_6$, ppm) δ: 147.64 (dd, J=243.1, 6.5 Hz), 142.43 (dd, J=12.0, 4.6 Hz), 133.08 (t, J=12.3 Hz), 127.22, 120.50 (q, J=323.7 Hz), 83.94, 52.10, 32.10, 26.47, 26.19, 23.99. $^{19}$F NMR (376 MHz, acetonitrile-d$_3$, ppm) δ: −78.70, −143.30. (LC-MS, m/z): Calc. for C$_{22}$H$_{32}$N$_2$F$_5$O$_6$S$_2$Na: 602.15. Found (M-Na)$^-$: 579.0.

A-PipOEtOiPrF$_2$: A 40 mL vial equipped with a magnetic stirring bar was charged with A-PipOiPrF$_3$ (0.5 mmol) and 4 mL dry DMF. Then sodium ethoxide (1.5 mmol) was added under nitrogen and stirred at room temperature for 12 h. The reaction was quenched by adding 5 ml 1M HCl aqueous solution. Then ethyl acetate (30 mL) was added to extract crude product, and washed with water (1×20 mL) and brine solution (2×20 mL). The organic layer was dried over anhydrous sodium sulfate and concentrated in vacuum. The residue was purified by flash chromatography on silica gel with acetone/hexanes (v/v=1/2) as the eluent to afford the product as white solids (0.20 g, 77%). $^1$H NMR (400 MHz, acetone-d$_6$, ppm) δ: 4.75-4.57 (m, 1H), 4.18 (q, J=7.0 Hz, 2H), 3.25-3.15 (m, 4H), 1.72-1.57 (m, 6H), 1.38 (t, J=7.0 Hz, 3H), 1.28 (d, J=6.1 Hz, 6H). $^{13}$C NMR (101 MHz, acetone-d$_6$, ppm) δ: 148.73 (dd, J=12.9, 6.6 Hz), 146.32 (dd, J=13.9, 6.6 Hz), 142.48 (dd, J=13.4, 3.8 Hz), 140.29 (dd, J=13.7, 3.6 Hz), 132.85 (t, J=12.6 Hz), 126.91, 120.41 (q, J=323.2 Hz), 77.86, 70.86, 52.06, 26.45, 23.96, 21.43, 14.76. $^{19}$F NMR (376 MHz, acetone-d$_6$, ppm) δ: −77.26, −140.26, −142.90. MS (m/z): Calc. for C$_{17}$H$_{22}$N$_2$F$_5$O$_6$S$_2$Na: 532.07. Found (M-Na)$^-$: 509.1.

A-o-PipONeop₂F₂: was synthesized by two more steps:

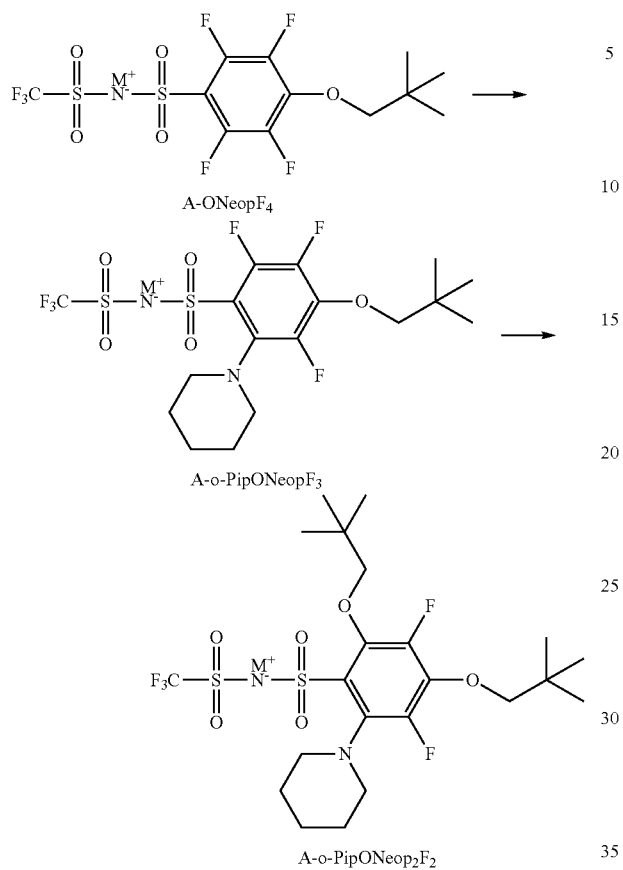

A 40 mL vial equipped with a magnetic stirring bar was charged with A-ONeopF₄ (0.7 mmol), piperidine (2.0 mmol) and 5 mL acetonitrile. The mixture was stirred at 60° C. for 12 h under nitrogen. Then 20 mL 1M HCl was added to the reaction. The white precipitate was filtered, washed with saturate sodium carbonate solution (20 mL), water (2×30 mL), and dried in vacuum to afford the product A-o-PipONeopF₃ as white solids (0.20 g, 77%). $^1$H NMR (500 MHz, DMSO-d₆, ppm) δ: 3.89 (s, 1H), 3.05-2.85 (m, 4H), 1.94-1.13 (m, 6H), 0.98 (s, 9H). $^{13}$C NMR (100 MHz, DMSO-d₆, ppm) δ: 151.95 (d, J=248.7 Hz), 144.97 (dd, J=253.0, 11.3 Hz), 141.95 (ddd, J=246.9, 17.6, 5.1 Hz), 139.63 (t, J=11.3 Hz), 135.92 (d, J=13.1 Hz), 127.48 (d, J=6.6 Hz), 120.46 (q, J=324.9 Hz), 84.53, 52.00, 32.76, 26.08, 25.80, 24.20. $^{19}$F NMR (376 MHz, DMSO-d₆, ppm) δ: −77.33, −137.57, −140.21, −155.25. MS (m/z): Calc. for C₁₇H₂₁N₂F₆O₅S₂Na: 534.07. Found (M-Na)⁻: 511.1.

To a 20 mL vial equipped with a magnetic stirring bar were added dry neopentanol (1.0 mmol), sodium hydride (1.0 mmol) and 3 mL dry DMF under nitrogen. After stirred at room temperature for 0.5 h, the mixture was transferred dropwise to another 40 ml vial which has been charged with A-o-PipONeopF₃ (0.4 mmol) and 3 mL DMF first. The reaction was quenched by adding 20 ml 1M HCl aqueous solution after further stirred at room temperature for 4 h. The white precipitate was filtered and washed by water (3×20 mL). The collected solids were dissolved in 30 mL ethyl acetate, washed with 1M NaOH (1×15 mL), water (1×20 mL) and brine solution (2×20 mL). The organic layer was dried over anhydrous sodium sulfate, concentrated and dried in vacuum to afford the product A-o-PipONeop₂F₂ as white solids (0.20 g, 85%). %). $^1$H NMR (400 MHz, DMSO-d₆, ppm) δ: 3.72 (s, 2H), 3.67 (s, 2H), 3.05-2.80 (m, 4H), 2.80-2.60 (m, 4H), 2.00-1.50 (m, 6H), 1.40-1.00 (m, 6H), 0.91 (d, J=8.7 Hz, 18H). $^{13}$C NMR (100 MHz, acetone-d₆, ppm) δ: 151.43 (dd, J=477.7, 6.1 Hz), 148.98 (dd, J=475.7, 6.1 Hz), 143.05 (dd, J=11.2, 4.1 Hz), 139.55 (t, J=13.8 Hz), 136.12 (dd, J=12.6, 4.1 Hz), 133.04 (d, J=3.4 Hz), 120.66 (q, J=324.7 Hz), 84.20, 51.71, 35.97, 32.37, 32.06, 26.18, 25.66, 25.54, 24.24. $^{19}$F NMR (376 MHz, DMSO-d₆, ppm) δ: −77.92, −141.28, −147.45. MS (m/z): Calc. for C₂₂H₃₂N₂F₅O₆S₂Na: 602.15. Found (M-Na)⁻: 579.1.

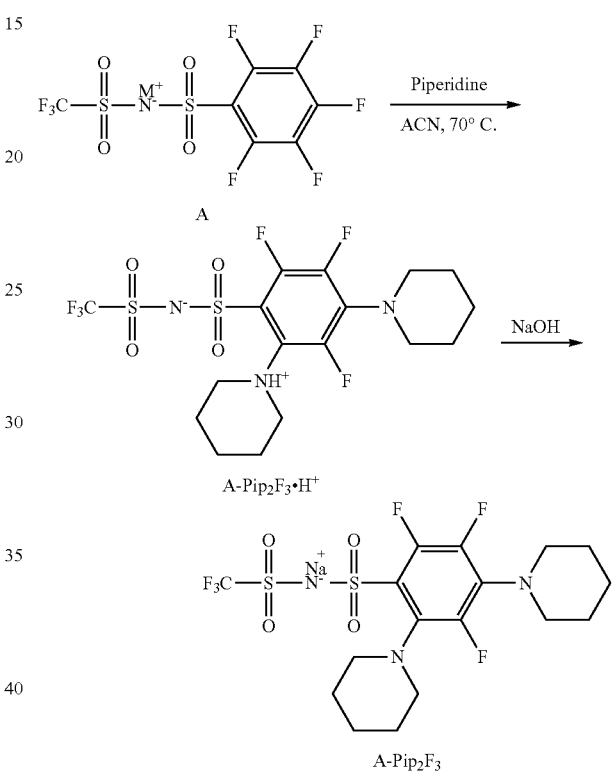

A-Pip₂F₃•H⁺: To a 50 mL round-bottomed flask equipped with a magnetic stirring bar were added A (3.0 mmol), piperidine (10 mmol), triethylamine (10.0 mmol), and 20 mL acetonitrile. The mixture was further stirred at 70° C. for 12 h. After removing acetonitrile under vacuum, the residue was dissolved in 30 mL ethyl acetate, and washed with 1M hydrochloric acid (1×20 mL), water (1×20 mL) and brine solution (2×20 mL). Then organic layer was dried over anhydrous sodium sulfate and concentrated in vacuum. The residue was purified by flash chromatography on silica gel with acetone/hexanes (v/v=1/2) as the eluent to afford the product as white solid (1.86 g, 65%), which is the protonated state of A-Pip₂F₃. $^1$H NMR (400 MHz, CDCl₃, ppm) δ: 11.69 (s, 1H), 3.90-3.65 (m, 4H), 3.35-3.25 (m, 4H), 2.15-1.95 (m, 5H), 1.75-1.65 (m, 6H), 1.65-1.55 (m, 1H). $^{13}$C NMR (101 MHz, CDCl3, ppm) δ: 153.62 (dd, J=244.8, 5.1 Hz), 144.78 (dd, J=250.8, 13.5 Hz), 143.16 (dm, J=245.4 Hz), 135.82 (d, J=15.1 Hz), 133.13 (t, J=11.0 Hz), 125.16, 120.29 (q, J=322.9 Hz), 51.96, 51.75, 26.38, 25.72, 24.18, 23.88 $^{19}$F NMR (376 MHz, CDCl3, ppm) δ: −78.42, −129.52, −132.39, −138.54. MS (m/z): Calc. for C₁₇H₂₁N₃F₆O₄S₂: 466.07. Found (M-H)⁻: 508.1.

A-Pip$_2$F$_3$: A-Pip$_2$F$_3$●H$^+$ was dissolved in 30 mL ethyl acetate, washed with 1M NaOH (1×15 mL), water (1×20 mL) and brine solution (2×20 mL). The organic layer was dried over anhydrous sodium sulfate, concentrated and dried in vacuum to afford the products as white solids. $^1$H NMR (400 MHz, acetone-d$_6$, ppm) δ: 3.26-3.16 (m, 4H), 3.10-2.92 (m, 4H), 1.95-1.77 (m, 2H), 1.75-1.65 (m, 7H), 1.52-1.40 (m, 2H), 1.37-1.20 (m, 1H). $^{13}$C NMR (100 MHz, acetone-d$_6$, ppm) δ: 151.75 (dd, J=258.6, 15.1 Hz), 150.12 (dm, J=250.5 Hz), 149.36 (dm, J=255.5 Hz), 139.60-139.22 (m), 126.27-125.09 (m), 123.48 (q, J=323.2 Hz), 120.02 (d, J=16.7 Hz), 60.30 (d, J=6.3 Hz), 56.00, 30.18, 28.64, 27.62, 24.95. $^{19}$F NMR (376 MHz, acetone-d$_6$, ppm) δ: −79.23, −133.23, −141.02, −150.07. MS (m/z): Calc. for C$_{17}$H$_{20}$N$_3$F$_6$O$_4$S$_2$Na: 531.07. Found (M-H)$^-$: 508.1.

General Procedure for A-Pip$_2$ORF$_2$

A 40 mL vial equipped with a magnetic stirring bar was charged with A-Pip$_2$F$_3$●H$^+$ (0.7 mmol) and 4 mL dry DMF. Then corresponding sodium alkoxide (2.0 mmol) was added under nitrogen and the mixture was stirred at room temperature for 4 h. The reaction was quenched by adding 20 ml 1M HCl aqueous solution. The white precipitate was filtered and washed by water (3×20 mL). The collected solids were dissolved in 30 mL ethyl acetate, washed with 1M NaOH (1×15 mL), water (1×20 mL) and brine solution (2×20 mL). The organic layer was dried over anhydrous sodium sulfate, concentrated and dried in vacuum to afford the products as white solids.

A-Pip$_2$OMeF$_2$ (0.31 g, 81%). $^1$H NMR (400 MHz, acetone-d$_6$, ppm) δ: 3.89 (s, 3H), 3.25-3.18 (m, 4H), 3.14-2.95 (m, 4H), 2.00-1.85 (m, 2H), 1.75-1.57 (m, 7H), 1.50-1.40 (m, 2H), 1.37-1.23 (m, 1H). $^{13}$C NMR (126 MHz, acetone-d$_6$, ppm) δ: 151.81 (dd, J=716.6, 7.0 Hz), 150.83 (dd, J=718.4, 7.0 Hz), 142.57 (dd, J=14.7, 3.8 Hz), 136.09 (dd, J=14.7, 3.8 Hz), 133.43-132.41 (m), 130.88 (d, J=4.4 Hz), 120.30 (q, J=322.9 Hz), 62.83, 52.07, 51.70, 26.48, 25.70, 24.26, 23.99. $^{19}$F NMR (376 MHz, acetone-d$_6$, ppm) δ: −79.38, −132.55, −141.28. MS (m/z): Calc. for C$_{18}$H$_{23}$N$_3$F$_5$O$_5$S$_2$Na: 543.09. Found (M-Na)$^-$: 520.1.

A-Pip$_2$OEtF$_2$ (0.30 g, 78%). $^1$H NMR (400 MHz, acetone-d$_6$, ppm) δ: 4.12 (q, J=8.0 Hz, 2H), 3.23-3.15 (m, 4H), 3.14-2.94 (m, 4H), 2.04-1.87 (m, 2H), 1.75-1.57 (m, 7H), 1.50-1.37 (m, 2H), 1.37-1.23 (m, 1H), 1.33 (t, J=8.0 Hz, 3H). $^{13}$C NMR (101 MHz, CDCl$_3$, ppm) δ: 151.81 (dd, J=254.4, 7.1 Hz), 147.43 (d, J=7.1 Hz), 145.20-144.75 (m), 134.93 (t, J=12.1 Hz), 122.51 (d, J=4.1 Hz), 122.35, 119.70 (q, J=323.2 Hz), 72.20, 55.85, 52.21, 26.40, 24.75, 23.90, 21.33, 15.42. $^{19}$F NMR (376 MHz, acetone-d$_6$, ppm) δ: −78.78, −133.32, −140.70. MS (m/z): Calc. for C$_{19}$H$_{25}$N$_3$F$_5$O$_5$S$_2$Na: 557.11. Found (M-Na)$^-$: 534.1.

A-Pip$_2$OiPrF$_2$ (0.31 g, 78%). $^1$H NMR (400 MHz, acetone-d$_6$, ppm) δ: 4.52-4.40 (m, 1H), 3.24-3.14 (m, 4H), 3.14-2.95 (m, 4H), 2.00-1.85 (m, 2H), 1.75-1.55 (m, 7H), 1.50-1.40 (m, 2H), 1.37-1.23 (m, 1H), 1.28 (d, J=8.0 Hz, 6H). $^{13}$C NMR (126 MHz, acetone-d$_6$, ppm) δ: 152.85 (dd, J=671.6, 6.3 Hz), 150.92 (dd, J=662.1, 6.3 Hz), 140.02 (dd, J=13.0, 6.3 Hz), 136.06 (dd, J=14.0, 6.3 Hz), 132.58 (t, J=12.5 Hz), 132.04, 120.33 (q, J=323.8 Hz), 78.67, 51.97, 51.56, 26.36, 25.51, 24.12, 23.87, 21.19. $^{19}$F NMR (376 MHz, DMSO-d$_6$, ppm) δ: −79.11, −132.63, −137.55. MS (m/z): Calc. for C$_{20}$H$_{27}$N$_3$F$_5$O$_5$S$_2$Na: 571.12. Found (M-Na)$^-$: 548.1.

A-Pip$_2$ONeopF$_2$ (0.32 g, 77%). $^1$H NMR (400 MHz, acetonitrile-d$_3$, ppm) δ: 3.77 (s, 2H), 3.28-3.14 (m, 4H), 3.14-2.95 (m, 4H), 2.05-1.87 (m, 2H), 1.80-1.57 (m, 7H), 1.52-1.40 (m, 2H), 1.37-1.23 (m, 1H), 1.04 (s, 9H). $^{13}$C NMR (126 MHz, acetonitrile-d$_3$, ppm) δ: 152.93 (dd, J=632.5, 6.1 Hz), 150.98 (dd, J=630.0, 6.1 Hz), 142.87 (dd, J=13.0, 4.1 Hz), 135.94 (dd, J=14.0, 4.3 Hz), 132.90-132.45 (m), 131.94 (d, J=5.0 Hz), 120.69 (q, J=324.7 Hz), 84.23, 52.13, 51.60, 32.10, 26.50, 26.19, 25.74, 24.32, 24.03. $^{19}$F NMR (376 MHz, acetonitrile-d$_3$, ppm) δ: −78.31, −133.65, −140.51. (m/z): Calc. for C$_{22}$H$_{31}$N$_3$F$_5$O$_5$S$_2$Na: 599.15. Found (M-Na)$^-$: 576.1.

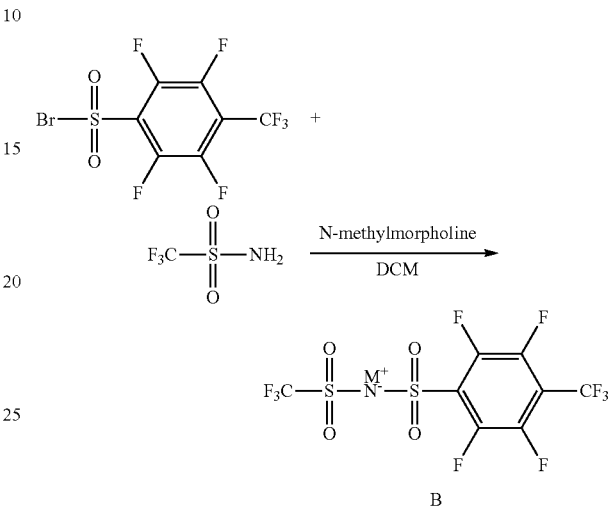

B: To a 100 mL round-bottomed flask equipped with a magnetic stirring bar were added trifluoromethane sulfonamide (8.0 mmol), N-methylmorpholine (16.0 mmol), and 40 mL DCM. The mixture was cooled to 0'° C. With stirring, 4-trifluoromethyl-2,3,5,6-tetrafluorobenzenesulfonyl bromide 12 (8.2 mmol) in 10 mL DCM was added dropwise via dropping funnel. The solution was further stirred at room temperature for 24 h. After removing DCM solvent under vacuum, the residue was dissolved in 100 mL ethyl acetate, and washed with 1M hydrochloric acid (1×30 mL), water (1×40 mL) and brine solution (2×40 mL). Then organic layer was dried over anhydrous sodium sulfate and concentrated in vacuum. The residue was purified by flash chromatography on silica gel with acetone/hexanes (v/v=1/2) as the eluent to afford the product as a white solid (2.60 g, 72%). $^{13}$C NMR (126 MHz, acetone-d$^6$, ppm δ) 142.10-139.55 (m), 138.16 (t, J=20.3 Hz), 122.65 (t, J=15.0 Hz), 115.71 (q, J=275.2 Hz), 114.92 (q, J=321.3 Hz), 108.56-103.96 (m). $^{19}$F NMR (376 MHz, acetone-d$^6$, ppm, δ): −57.61, −79.58, −137.16, −141.80. MS (m/z): Calc. for C$_8$NF$_{10}$O$_4$S$_2$Na: 450.90. Found (M-Na) 427.9.

The synthesis procedure of B—OR$_4$ was similar with A-OR$_3$F$_2$. The product was acquired as white solids by flash chromatography on silica gel with acetone/hexanes (v/v=1/2) as the eluent. B-OEt$_4$ (58%). $^1$H NMR (400 MHz, acetone-d$_6$, ppm) δ: 4.19 (q, J=7.0 Hz, 4H), 4.09 (t, J=7.0 Hz, 4H), 1.46-1.32 (m, 12H). $^{13}$C NMR (101 MHz, acetone-d$_6$, ppm) δ: 148.03, 147.64, 137.53, 123.18 (q, J=276.1 Hz), 120.80 (q, J=28.2 Hz), 120.33 (q, J=323.8 Hz), 70.21, 69.99, 14.85. $^{19}$F NMR (376 MHz, acetone-d$_6$, ppm) δ: −56.49, −78.67. (m/z): Calc. for C$_{16}$H$_{20}$NF$_6$O$_8$S$_2$Na: 555.04. Found (M-Na)$^-$: 532.0.

B-OiPr$_4$ (64%). $^1$H NMR (400 MHz, DMSO-d$_6$, ppm) δ: 4.95-4.70 (m, 4H), 1.45-1.1 (m, 24H). $^{13}$C NMR (101 MHz, acetone-d$_6$, ppm) δ: 145.94, 145.44, 138.11, 123.35 (q, J=276.1 Hz), 121.20 (q, J=27.2 Hz), 120.37 (q, J=324.2 Hz), 76.02, 74.11, 21.33, 21.29. $^{19}$F NMR (376 MHz, DMSO-d$_6$, ppm) δ: −53.74, −78.89. MS (m/z): Calc. for C$_{20}$H$_{28}$NF$_6$O$_8$S$_2$Na: 611.11. Found (M-Na)⁻: 588.1.

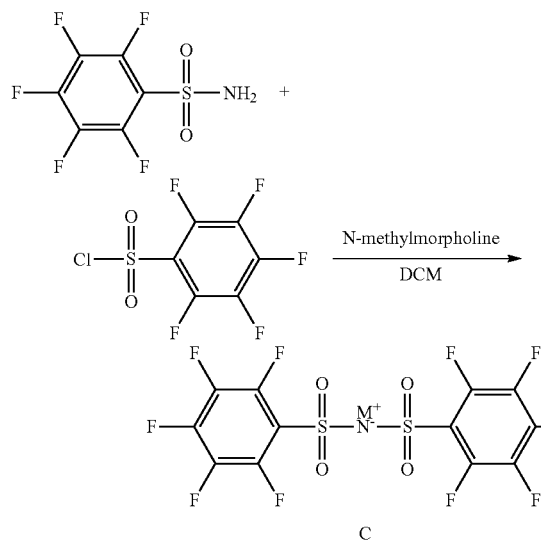

C: To a 100 mL round-bottomed flask equipped with a magnetic stirring bar were added 2,3,4,5,6-pentafluorobenzene sulfonamide (10.0 mmol), N-methylmorpholine (20.0 mmol), and 60 mL DCM. The mixture was cooled to 0° C. With stirring, 2,3,4,5,6-pentafluorobenzene sulfonyl chloride (10.5 mmol) in 15 mL DCM was added dropwise via dropping funnel. The solution was further stirred at room temperature for 24 h. After removing DCM solvent under vacuum, the residue was dissolved in 100 mL ethyl acetate, and washed with 1M HCl (1×30 mL), and brine solution (2×40 mL). Then organic layer was dried over anhydrous sodium sulfate and concentrated in vacuum. The residue was purified by flash chromatography on silica gel with acetone/hexanes (v/v=2/3) as the eluent to afford the product as a white solid (2.60 g, 84%). $^{13}$C NMR (101 MHz, acetone-d$^6$, ppm, δ): 144.39 (ddd, J=255.2, 11.7, 5.8 Hz), 142.43 (dm, J=255.4 Hz), 137.38 (dm, J=250.1 Hz), 120.88 (t, J=15.4 Hz). $^{19}$F NMR (376 MHz, acetone-d$^6$, ppm, δ): −137.72, −150.75, −162.13. MS (m/z): Calc. for C12NF$_{10}$O$_4$S$_2$Na: 498.90. Found (M-Na)⁻: 475.9.

C-PipF$_4$ (75%): The synthesis procedure was similar with A-PipF$_4$. $^1$H NMR (400 MHz, DMSO-d$_6$, ppm) δ: 3.25-3.17 (m, 8H), 1.68-1.54 (m, 12H). $^{13}$C NMR (101 MHz, acetone-d$_6$, ppm) δ: 144.43 (dm, J=259.1 Hz), 140.99 (dm, J=240.9 Hz), 133.21, 114.80-114.0 (m), 51.86, 26.28, 23.75. $^{19}$F NMR (376 MHz, DMSO-d$_6$, ppm) δ: −77.96, −140.13, −151.99. MS (m/z): Calc. for C$_{12}$H$_{10}$N$_2$F$_7$O$_4$S$_2$Na: 466.0. Found (M-Na)⁻: 443.0.

C-PipOEt$_2$F$_2$ (72%): The synthesis procedure was similar with A-PipOEt$_2$F$_2$. $^1$H NMR (400 MHz, CDCl$_3$, ppm) δ: 4.07 (q, J=6.8 Hz, 1H), 3.23-3.10 (m, 8H), 1.72-1.54 (m, 12H), 1.36 (t, J=6.9 Hz, 12H). $^{13}$C NMR (101 MHz, acetone-d$_6$, ppm) δ: 146.91 (dm, J=242.4 Hz), 142.86-142.25 (m), 135.80-134.60 (m), 117.90, 71.70, 52.07, 26.53, 24.05, 14.90. $^{19}$F NMR (376 MHz, acetone-d$_6$, ppm) δ: −142.00. MS (m/z): Calc. for C$_{30}$H$_{40}$N$_3$F$_4$O$_8$S$_2$Na: 733.21. Found (M-Na)⁻: 710.2.

C-PipOiPr$_2$F$_2$ (68%): The synthesis procedure was similar with A-PipOiPr$_2$F$_2$. $^1$H NMR (400 MHz, CDCl$_3$, ppm) δ: 4.46-4.32 (m, 4H), 3.15-3.07 (m, 8H), 1.65-1.46 (m, 12H), 1.20 (d, J=6.1 Hz, 24H). $^{13}$C NMR (101 MHz, CDCl$_3$, ppm) δ: 147.23 (dd, J=242.7, 6.2 Hz), 141.68-138.40 (m), 132.82 (t, J=12.7 Hz), 124.77, 78.19, 52.15, 26.60, 24.32, 22.07. $^{19}$F NMR (376 MHz, CDCl$_3$, ppm) δ: −139.86. MS (m/z): Calc. for C$_{34}$H$_{48}$N$_3$F$_4$O$_8$S$_2$Na: 789.27. Found (M-Na)⁻: 766.2.

General Procedure for Chemical Stability Test

A 10 mL microwave vial was charged with 0.040 mmol sulfonamide salts and a stir bar, and transferred into the glove box. Then 0.5 mmol Li$_2$O$_2$, 0.5 mmol KO$_2$, 0.040 mmol 4-Methoxybiphenyl and 0.8 mL DMF were added into the vial. 4-Methoxybiphenyl has been proved to be stable under test condition (see Feng, S.; Chen, M.; Giordano, L.; Huang, M.; Zhang, W.; Amanchukwu, C. V.; Anandakathir, R.; Shao-Horn, Y.; Johnson, J. A. *J. Mater. Chem. A* 2017, 5, 23987-23998, which is incorporated by reference in its entirety) and is chosen as the inner stand for quantitatively calculation of survived sulfonamide salts via $^1$H-NMR integration. After the vial was sealed, it was moved out of the glove box and heated in an oil bath at 80° C. for 3 days. Then, the reaction mixture was cooled down and treated with d$^6$-DMSO. The mixture was further centrifuged. The liquid layer was analyzed with $^1$H, $^{19}$F-NMR, and LC-MS.

NMR results of chemical stability test are shown in FIGS. 14-44.

Other embodiments are within the scope of the following claims.

What is claimed is:

1. A composition comprising:

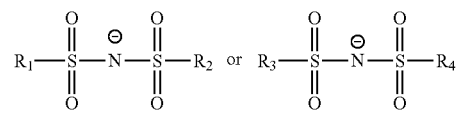

wherein R$_1$ is —CF$_3$ or a fluorinated phenyl and R$_2$ is a fluorinated phenyl or R$_3$ is —CF$_3$ or a fluorinated phenyl and R$_4$ is a fluorinated phenyl, wherein at least one of R$_3$ and R$_4$ is substituted by an alkoxide or an amine
wherein R$_3$ is—CF$_3$ or a fluorinated phenyl and R$_4$ is a fluorinated phenyl, wherein at least one of R$_3$ and R$_4$ is substituted by a nucleophile
wherein the fluorinated phenyl has a formula

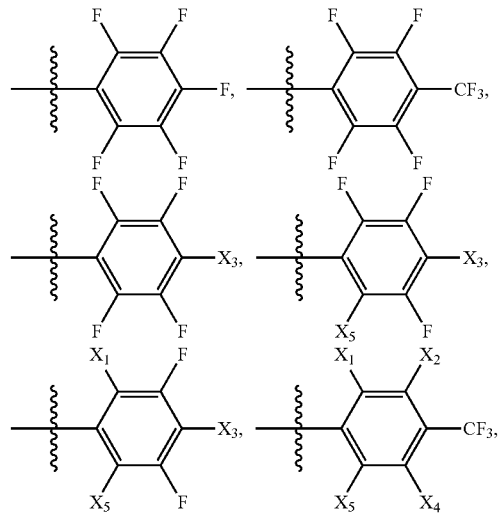

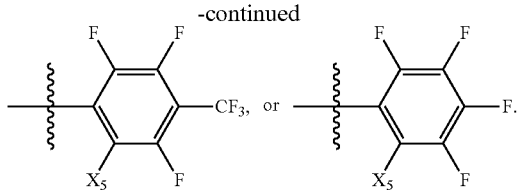 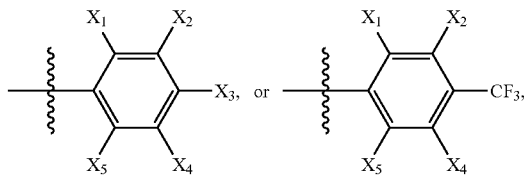

wherein each of $X_1$, $X_3$, and $X_5$, independently, is methoxy, ethoxy, propoxy, butoxy, pentoxy, phenoxy, piperidinyl, or cyclootceneamino.

2. The composition of claim 1, wherein $R_1$ is —$CF_3$.

3. The composition of claim 1, wherein $R_1$ is a fluorinated phenyl.

4. The composition of claim 3, wherein the fluorinated phenyl has at least two fluorine groups.

5. The composition of claim 3, wherein the fluorinated phenyl has a formula

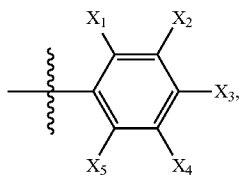

wherein each of $X_1$, $X_2$, $X_3$, $X_4$, and $X_5$, independently, is F or $CF_3$.

6. The composition of claim 3, wherein the fluorinated phenyl has a formula

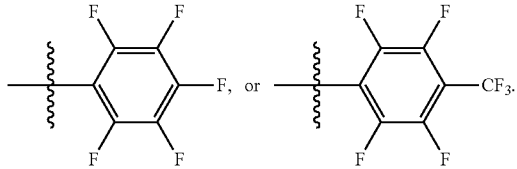

7. The composition of claim 1, wherein the fluorinated phenyl has a formula

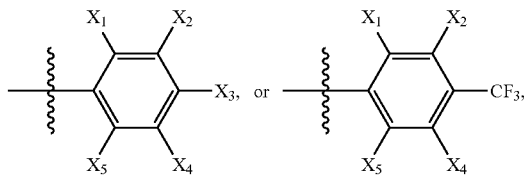

wherein each of $X_1$, $X_2$, $X_3$, $X_4$, and $X_5$, independently, is F, $OR_a$, or $NR_cR_d$, wherein $R_a$ is C1-C6 alkyl, benzalkyl, or substituted or unsubstituted phenyl, $R_b$ is C1-C6 alkyl, benzalkyl, or phenyl, $R_c$ is C1-C6 alkyl, benzalkyl, or phenyl, or $R_b$ and $R_c$ together form a three to eight membered ring.

8. The composition of claim 1, wherein the compound has formula (I) or formula (II)

$$P\text{-Pip}_x OR_y F_z \quad (I)$$

$$P\text{-Pip}_x OPh_w F_z \quad (II)$$

wherein P is a perfluoroarylsulfonimide anion, Pip is a piperidine, OR is an alkoxide, F is a fluorine substituent, OPh is phenoxide, and each of x, y, z and w, independently, is 0, 1, 2 or 3, wherein the sum of x, y, and z or x, z and w is 0, 1, 2 or 3.

9. The composition of claim 8, wherein OR is methoxy, ethoxy, isopropoxy or neopentoxy.

10. An energy storage device comprising an electrolyte including a composition of claim 1.

11. The energy storage device of claim 10, wherein the compound has formula (I) or formula (II)

$$P\text{-Pip}_x OR_y F_z \quad (I)$$

$$P\text{-Pip}_x OPh_w F_z \quad (II)$$

wherein P is a perfluoroarylsulfonimide anion, Pip is a piperidine, OR is methoxy, ethoxy, isopropoxy or neopentoxy, F is a fluorine substituent, OPh is phenoxide, and each of x, y, z and w, independently, is 0, 1, 2 or 3, wherein the sum of x, y, and z or x, z and w is 0, 1, 2 or 3.

12. The energy storage device of claim 11, wherein OR is methoxy, ethoxy, isopropoxy or neopentoxy.

* * * * *